US012807595B2

(12) United States Patent
Sikervar et al.

(10) Patent No.: US 12,807,595 B2
(45) Date of Patent: Nov. 24, 2026

(54) PESTICIDALLY ACTIVE HETEROCYCLIC DERIVATIVES WITH SULFUR CONTAINING SUBSTITUENTS

(71) Applicant: SYNGENTA CROP PROTECTION AG, Basel (CH)

(72) Inventors: Vikas Sikervar, Bracknell (GB); Swarnendu Sasmal, Corlim (IN); Michel Muehlebach, Stein (CH); André Stoller, Stein (CH); Daniel Emery, Stein (CH); André Jeanguenat, Stein (CH); Anke Buchholz, Stein (CH); Benedikt Kurtz, Stein (CH)

(73) Assignee: SYNGENTA CROP PROTECTION AG, Basel (CH)

(*) Notice: Subject to any disclaimer, the term of this patent is extended or adjusted under 35 U.S.C. 154(b) by 699 days.

(21) Appl. No.: 18/043,389

(22) PCT Filed: Aug. 31, 2021

(86) PCT No.: PCT/EP2021/073993
§ 371 (c)(1),
(2) Date: Feb. 28, 2023

(87) PCT Pub. No.: WO2022/043576
PCT Pub. Date: Mar. 3, 2022

(65) Prior Publication Data

US 2024/0018128 A1 Jan. 18, 2024

(30) Foreign Application Priority Data

Aug. 31, 2020 (IN) ............................ 202011037485

(51) Int. Cl.

| | |
|---|---|
| ***C07D 403/14*** | (2006.01) |
| ***A01N 43/56*** | (2006.01) |
| ***A01P 7/04*** | (2006.01) |
| ***C07D 471/04*** | (2006.01) |

(52) U.S. Cl.
CPC ........... *C07D 403/14* (2013.01); *A01N 43/56* (2013.01); *A01P 7/04* (2021.08); *C07D 471/04* (2013.01)

(58) Field of Classification Search
CPC .... C07D 403/14; C07D 471/04; A01N 43/56; A01P 7/04
See application file for complete search history.

(56) References Cited

U.S. PATENT DOCUMENTS

| | | | |
|---|---|---|---|
| 11,058,115 B2 | 7/2021 | Wilcke et al. | |
| 11,083,199 B2 * | 8/2021 | Wilcke | C07D 471/04 |
| 2015/0368249 A1 | 12/2015 | Ochi et al. | |

FOREIGN PATENT DOCUMENTS

| | | | |
|---|---|---|---|
| CN | 110312718 A | 10/2019 | |
| CN | 110382485 A | 10/2019 | |
| WO | 2012031004 A1 | 3/2012 | |
| WO | 2018130437 A1 | 7/2018 | |
| WO | WO-2018130443 A1 * | 7/2018 | A01N 43/90 |
| WO | 2019131575 A1 | 7/2019 | |
| WO | 2020002082 A1 | 1/2020 | |

OTHER PUBLICATIONS

Crop Science US; Bayer. https://www.cropscience.bayer.us/articles/cp/recognizing-corn-rootworm-risks. Recognizing Corn Rootworm Risks. (accessed Nov. 10, 2025). (Year: 2018).*

Zucchi, M. I. et al. Population Genomics of the Neotropical Brown Stink Bug, *Euschistus heros:* The Most Important Emerging Insect Pest to Soybean in Brazil. Frontiers in Genetics 2019, 10, 1035. (Year: 2019).*

Mouden, S. et al. Integrated pest management in western flower thrips: past, present and future. Pest Manag Sci 2017, 73, 813-822. (Year: 2017).*

Cutler, G. C. et al. Green peach aphid, *Myzus persicae* (Hemiptera: Aphididae), reproduction during exposure to sublethal concentrations of imidacloprid and azadirachtin. Pest Manag Sci 2009, 65, 205-209. (Year: 2009).*

Sarfraz, M. et al. Diamondback moth-host plant interactions: implications for pest mangement. Crop Protection 2006, 25, 625-639. (Year: 2006).*

Clapham, W. B. Agricultural system structure and the Egyptian cotton leafworm. 1979. (Year: 1979).*

Pollard, D. G. Feeding habits of the cotton whitefly, *Bemisia Tabaci* Genn. (Homoptera: aleyrodidae) Ann. Appl. Biol. 1955, 43, 664-671. (Year: 1955).*

Jiang, W. et al. Rice striped stem borer, *Chilo suppressalis* (Lepidoptera: Pyralidae), overwintering insuper rice and its control using cultivation techniques. Crop Protection 2011, 30, 130-133. (Year: 2011).*

(Continued)

*Primary Examiner* — Jeffrey H Murray
*Assistant Examiner* — Kristen W Romero
(74) *Attorney, Agent, or Firm* — BakerHostetler; Toni-Junell Herbert

(57) ABSTRACT

(I)

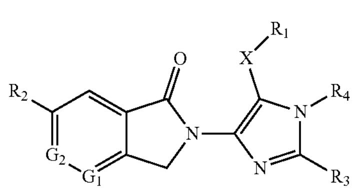

Compounds of the formula (I) wherein $G_1$, $G_2$, X, $R_1$, $R_2$, $R_3$, and $R_4$ are as defined herein. Furthermore, the present invention relates to agrochemical compositions which comprise compounds of formula (I), to preparation of these compositions, and to the use of the compounds or compositions in agriculture or horticulture for combating, preventing or controlling animal pests, including arthropods and in particular insects, molluscs, nematodes or representatives of the order Acarina.

21 Claims, No Drawings

(56) References Cited

OTHER PUBLICATIONS

Di Mauro et al; "Mechanistic Pathways in Amide Activation: Flexible Synthesis of Oxazoles Imidazoles"; Organic Letters; Jul. 21, 2017; vol. 19 (14), pp. 3815-3818, ISSN: 1523-7060.

WIPO; App. No. PCT/EP2021/073993; Partial International Search and Provisional Opinion Accompanying the Partial Search Report malled Dec. 20, 2021; pp. 1-13.

WIPO; App. No. PCT/EP2021/073993; International Search Report and Written Opinion mailed Mar. 21, 2022; pp. 1-20.

* cited by examiner

PESTICIDALLY ACTIVE HETEROCYCLIC DERIVATIVES WITH SULFUR CONTAINING SUBSTITUENTS

CROSS-REFERENCE TO RELATED APPLICATIONS

This application is a U.S. National Stage Application, filed under 35 U.S.C. § 371, of International Application No. PCT/EP2021/073993, filed Aug. 31, 2021, which claims priority to IN 202011037485, filed Aug. 31, 2020, the entire contents of which are incorporated by reference herein.

The present invention relates to pesticidally active, in particular insecticidally active heterocyclic derivatives containing sulfur substituents, to processes for their preparation, to compositions comprising those compounds, and to their use for controlling animal pests, including arthropods and in particular insects or representatives of the order Acarina.

Heterocyclic benzannulated dihydropyrrolone and phthalimide derivatives with sulfur-containing substituents have been described in the literature, for example in *J. Org. Chem.* 2003, 62, 8240 and *Bull. Chem Soc. Chim. Belg.* 1997, 106, 151. However, none of these references have described to have a pesticidal effect. Structurally different pesticidally active heterocyclic derivatives with sulfur-containing substituents have been described, for example in WO2012/012086848, WO2013/018928, WO2019/131575, WO2018/130437, WO2018/130443 and WO2020/002082.

It has now surprisingly been found that certain novel pesticidally active derivatives with sulfur containing substitutents have favorable properties as pesticides.

The present invention therefore provides compounds of formula I, (I)

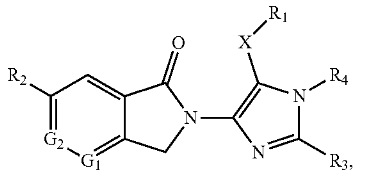

wherein $G_1$ and $G_2$ are, independently from each other, CH or N;

$R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy;

X is S, SO, or $SO_2$;

$R_1$ is $C_1$-$C_4$ alkyl, or $C_3$-$C_6$ cycloalkyl-$C_1$-$C_4$ alkyl;

$R_4$ is $C_1$-$C_4$ alkyl;

$R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —CO($NR_5R_6$), —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl; or $R_3$ is a five- to six-membered saturated, partially saturated, aromatic or heteroaromatic ring system, linked via a ring carbon atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$—$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom; or $R_3$ is a five-membered heteroaromatic ring system linked via a ring nitrogen atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom;

$R_5$ and $R_6$ are independently H, $C_1$-$C_6$ alkyl, $C_1$-$C_6$ haloalkyl or $C_3$-$C_6$ cycloalkyl; and $R_7$ is $C_1$-$C_6$ alkyl, $C_1$-$C_6$ haloalkyl or $C_3$-$C_6$ cycloalkyl.

The present invention also provides agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrous acid, a phosphorus acid or a hydrohalic acid, with strong organic carboxylic acids, such as $C_1$-$C_4$ alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$ alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

In each case, the compounds of formula (I) according to the invention are in free form, in oxidized form as a N-oxide or in salt form, e.g. an agronomically usable salt form.

N-oxides are oxidized forms of tertiary amines or oxidized forms of nitrogen containing heteroaromatic compounds. They are described for instance in the book "Heterocyclic N-oxides" by A. Albini and S. Pietra, CRC Press, Boca Raton 1991.

The compounds of formula I according to the invention also include hydrates which may be formed during the salt formation.

Where substituents are indicated as being itself further substituted, this means that they carry one or more identical or different substituents, e.g. one to four substituents. Normally not more than three such optional substituents are present at the same time. Preferably not more than two such substituents are present at the same time (i.e. the group is substituted by one or two of the substituents indicated). Where the additional substituent group is a larger group, such as cycloalkyl or phenyl, it is most preferred that only one such optional substituent is present. Where a group is indicated as being substituted, e.g. alkyl, this includes those groups that are part of other groups, e.g. the alkyl in alkylthio.

The term "$C_1$-$C_n$ alkyl" as used herein refers to a saturated straight-chain or branched hydrocarbon radical attached via any of the carbon atoms having 1 to n carbon atoms, for example, any one of the radicals methyl, ethyl, n-propyl, 1-methylbutyl, 2-methylbutyl, 3-methylbutyl, 2,2-dimethylpropyl, 1-ethylpropyl, n-hexyl, n-pentyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "$C_1$-$C_n$ haloalkyl" as used herein refers to a straight-chain or branched saturated alkyl radical attached via any of the carbon atoms having 1 to n carbon atoms (as mentioned above), where some or all of the hydrogen atoms in these radicals may be replaced by fluorine, chlorine, bromine and/or iodine, i.e., for example, any one of chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl. According a term "$C_1$-$C_2$-fluoroalkyl" would refer to a $C_1$-$C_2$-alkyl radical which carries 1,2, 3,4, or 5 fluorine atoms, for example, any one of difluoromethyl, trifluoromethyl, 1-fluoroethyl, 2-fluoroethyl, 2,2-difluoroethyl, 2,2,2-trifluoroethyl, 1,1,2,2-tetrafluoroethyl or pentafluoroethyl.

The term "$C_1$-$C_n$ alkoxy" as used herein refers to a straight-chain or branched saturated alkyl radical having 1 to n carbon atoms (as mentioned above) which is attached via an oxygen atom, i.e., for example, any one of methoxy, ethoxy, n-propoxy, 1-methylethoxy, n-butoxy, 1-methylpropoxy, 2-methylpropoxy or 1,1-dimethylethoxy.

The term "$C_1$-$C_n$ haloalkoxy" as used herein refers to a $C_1$-$C_n$ alkoxy radical as mentioned above which is partially or fully substituted by fluorine, chlorine, bromine and/or iodine, i.e., for example, any one of chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, or 4-bromobutoxy.

The term "$C_1$-$C_n$-alkylsulfanyl" as used herein refers to a straight chain or branched saturated alkyl radical having 1 to n carbon atoms (as mentioned above) which is attached via a sulfur atom, i.e., for example, any one of methylthio, ethylthio, n-propylthio, 1-methylethylthio, butylthio, 1-methylpropylthio, 2-methylpropylthio or 1,1-dimethylethylthio.

The term "$C_1$-$C_n$ alkylsulfinyl" as used herein refers to a straight chain or branched saturated alkyl radical having 1 to n carbon atoms (as mentioned above) which is attached via the sulfur atom of the sulfinyl group, i.e., for example, any one of methylsulfinyl, ethylsulfinyl, n-propylsulfinyl, 1-methylethyl-sulfinyl, n-butylsulfinyl, 1-methylpropylsulfinyl, 2-methylpropylsulfinyl, 1,1-dimethyl-ethylsulfinyl, n-pentylsulfinyl, 1-methylbutylsulfinyl, 2-methylbutylsulfinyl, 3-methyl-butylsulfinyl, 1,1-dimethylpropylsulfinyl, 1,2-dimethylpropylsulfinyl, 2,2-dimethylpropylsulfinyl or 1-ethylpropylsulfinyl.

The term "$C_1$-$C_n$ alkylsulfonyl" as used herein refers to a straight chain or branched saturated alkyl radical having 1 to n carbon atoms (as mentioned above) which is attached via the sulfur atom of the sulfonyl group, i.e., for example, any one of methylsulfonyl, ethylsulfonyl, n-propylsulfonyl, isopropylsulfonyl, n-butylsulfonyl, 1-methylpropylsulfonyl, 2-methylpropylsulfonyl ort-butylsulphonyl.

The term "$C_1$-$C_n$ haloalkylsulfanyl" as used herein refers to a $C_1$-$C_n$ alkylsulfanyl radical (as mentioned above) which is partially or fully substituted by fluorine, chlorine, bromine and/or iodine, i.e., for example, any one of fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, or 4-bromobutylthio.

The term "$C_1$-$C_n$ haloalkylsulfinyl" and "$C_1$-$C_n$ haloalkylsulfonyl" refers to the groups above but with the sulfur in oxidations state 1 or 2 respectively.

The term "$C_1$-$C_n$ haloalkylsulfonyloxy" as used herein refers to a $C_1$-$C_n$ haloalkylsulfonyl (as mentioned above) which is attached via an oxygen atom.

The term "$C_1$-$C_n$ cyanoalkyl" as used herein refers to a straight chain or branched saturated alkyl radicals having 1 to n carbon atoms (as mentioned above) which is substituted by a cyano group, for example cyanomethylene, cyanoethylene, 1,1-dimethylcyanomethyl, cyanomethyl, cyanoethyl, and 1-dimethylcyanomethyl.

The term "$C_3$-$C_n$ cycloalkyl" as used herein refers to saturated or partially unsaturated mono-, bi- or tricyclic hydrocarbons having 3 to n carbon atoms, preferably 3 to 8 carbon atoms, for example cyclopropyl, cyclobutyl, cyclopentyl, cyclohexyl, cycloheptyl, cyclooctyl, bicyclo[2.2.1]heptyl and bicyclo[2.2.2]octyl.

The term "$C_3$-$C_n$ cycloalkyl" monosubstituted by cyano as used herein refers to saturated or partially unsaturated mono-, bi- or tricyclic hydrocarbons having 3 to n carbon atoms (as mentioned above) which is substituted by a cyano group.

The suffix "—$C_1$-$C_n$ alkyl" after terms such as "$C_3$-$C_n$ cycloalkyl" as used herein refers to a straight chain or branched saturated alkyl radicals having 1 to n carbon atoms (as mentioned above) which is substituted by $C_3$-$C_n$ cycloalkyl. An example of $C_3$-$C_n$ cycloalkyl-$C_1$-$C_n$ alkyl is for example, cyclopropylmethyl.

Halogen is generally fluorine, chlorine, bromine or iodine. This also applies, correspondingly, to halogen in combination with other meanings, such as haloalkyl.

In the context of this invention "mono- or polysubstituted" in the definition of the $R_3$ substituents, means typically, depending on the chemical structure of the substituents, monosubstituted to five-times substituted, more preferably mono-, double- or triple-substituted.

In the context of the this invention, the phrase "$R_3$ is a five- to six-membered saturated, partially saturated, aromatic or heteroaromatic ring system, linked via a ring carbon atom to the imidazole ring which is connected to the substitutent $R_4$ . . . " and the phrase "$R_3$ is a five-membered aromatic ring system linked via a ring nitrogen atom to the imidazole ring which is connected to the substitutent $R_4$ . . . ", as the case may be, refer to the manner of attachment of particular embodiments of the substituent $R_3$ in the formula I, as the case may be.

In the context of this invention, examples of "$R_3$ is a five- to six-membered saturated, partially saturated, aromatic or heteroaromatic ring system, linked via a ring carbon atom to the imidazole ring which is connected to the substitutent $R_4$, . . . "; and said ring system can contain 1, 2 or 3 ring heteroatoms . . . " are, but not limited to, phenyl, pyrazolyl, imidazolyl, triazolyl, pyridinyl, isoxazolyl, dihydroisoxazolyl, oxazolyl and pyrimidinyl.

In the context of this invention, examples of a "$R_3$ is a five-membered heteroaromatic ring system linked via a ring nitrogen atom to the imidazole ring which is connected to the substituent $R_4$, . . . ; and said ring system contains 1, 2 or 3 ring heteroatoms . . . " are, but not limited to, pyrazolyl, pyrrolyl, imidazolyl and triazolyl.

Certain embodiments according to the invention are provided as set out below.

Embodiment 1 provides compounds of formula I, or an agrochemically acceptable salt, stereoisomer, enantiomer, tautomer or N-oxide thereof, as defined above.

Embodiment 2 provides compounds, or an agrochemically acceptable salt, stereoisomer, enantiomer, tautomer or N-oxide thereof, according to embodiment 1 wherein preferred values of $G_1$, $G_2$, X, $R_1$, $R_2$ $R_3$, $R_4$, $R_5$, $R_6$ and $R_7$ are, in any combination thereof, as set out below:

Preferably $G_1$ and $G_2$ are, independently from each other, CH or N.

Also preferred are when both $G_1$ and $G_2$ are N.

More preferably either $G_1$ is N and $G_2$ is CH, or $G_1$ is CH and $G_2$ is N;

Most preferably both $G_1$ and $G_2$ are CH.

Preferably X is S or $SO_2$.

Most preferably X is $SO_2$.

Preferably $R_1$ is $C_1$-$C_4$ alkyl or cyclopropyl-$C_1$-$C_4$ alkyl.

More preferably $R_1$ is ethyl or cyclopropylmethyl.

Most preferably $R_1$ is ethyl.

Preferably $R_2$ is $C_1$-$C_6$ haloalkyl, $C_1$-$C_4$ haloalkylsulfonyl, $C_1$-$C_6$ haloalkoxy or $C_1$-$C_4$ haloalkylsulfonyloxy. Also preferred is when $R_2$ is $C_1$-$C_6$ fluoroalkyl, $C_1$-$C_4$ fluoroalkylsulfonyl, $C_1$-$C_6$ fluoroalkoxy or $C_1$-$C_4$ fluoroalkylsulfonyloxy.

More preferably $R_2$ is —$CF_3$, —$OCF_3$, —$SO_2CF_3$, or —$CF_2CF_3$.

Even more preferably $R_2$ is —$OCF_3$, —$CF_2CF_3$ or —$CF_3$.

Most preferably $R_2$ is —$CF_3$ or —$OCF_3$.

Preferably $R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —$CO(NR_5R_6)$, —$NR_5COR_7$, ($C_3$-$C_8$)cycloalkyl-($C_1$-$C_6$)alkyl- or ($C_3$-$C_8$)cycloalkyl mono-substituted by cyano-($C_1$-$C_6$)alkyl. Also preferred is when $R_3$ is a five- to six-membered partially saturated, aromatic or heteroaromatic ring system, linked via a ring carbon atom to the imidazole ring which is connected to the substituent $R_4$, said ring system is unsubstituted or is monosubstituted by substituents selected from the group consisting of halogen, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$) alkyl-; and said ring system can contain 1 or 2 ring heteroatoms selected from the group consisting of nitrogen and oxygen, where said ring system may not contain more than one ring oxygen atom. Also preferred is when $R_3$ is a five-membered heteroaromatic ring system linked via a ring nitrogen atom to the imidazole ring which is connected to the substituent $R_4$, said ring system is unsubstituted or is monosubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_4$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system contains 1 or 2 ring nitrogen atoms.

More preferably $R_3$ is $C_3$-$C_6$ cycloalkyl; $C_1$-$C_6$ haloalkoxy; —$CO(NR_5R_6)$; or —$NR_5COR_7$. Also more preferred is when $R_3$ is phenyl which can be monosubstituted by $C_3$-$C_6$ cycloalkyl monosubstituted by cyano; C-linked pyrimidinyl; C-linked pyrazolyl which can be monosubstituted by $C_1$-$C_4$ haloalkyl, $C_3$-$C_6$ cycloalkyl, ($C_3$-$C_8$)cycloalkyl-($C_1$-$C_6$)alkyl- or ($C_3$-$C_8$)cycloalkyl monosubstituted by cyano-($C_1$-$C_6$)alkyl-; or C-linked dihydroisoxazolyl which can be monosubstituted by $C_3$-$C_6$ cycloalkyl.

Also more preferred is when $R_3$ is N-linked pyrazolyl which can be mono-substituted by halogen, $C_1$-$C_4$ haloalkyl or $C_3$-$C_6$ cycloalkyl.

Further preferred is when $R_3$ is hydrogen, halogen, cyclopropyl, cyanocyclopropyl, trifluoroethoxy, —$CONCH_3(CH_2CF_3)$, —$N(CH_3)COCH_2CF_3$.

Also further preferred is when $R_3$ is selected from N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —$(CH_2)$-cyclopropyl, —$(CH_2)$-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

Most preferably $R_3$ is selected from —$OCH_2CF_3$; —$N(CH_3)COCH_2CF_3$; —$CON(CH_3)CH_2CF_3$; 3-chloro-pyrazol-1-yl; 3-cyclopropyl-pyrazol-1-yl; 4-(1-cyanocyclopropyl)phenyl; 3-(1-cyanocyclopropyl)phenyl; pyrimidin-5-yl; pyrimidin-2-yl; 1-cyclopropylpyrazol-4-yl; cyclopropyl; 1-difluoromethylpyrazol-4-yl; 1-(2,2-difluoroethyl)pyrazol-4-yl; 1-(2,2,2-trifluoroethyl)pyrazol-4-yl, 3-cyclopropyl-4,5-dihydro-isoxazol-5-yl; 3-trifluoromethyl-pyrazol-1-yl; 4-trifluoromethyl-pyrazol-1-yl; 1-(cyclopropylmethyl)pyrazol-4-yl and 1-(1-cyanocyclopropylmethyl)pyrazol-4-yl.

Preferably $R_4$ is $C_1$-$C_4$ alkyl.

More preferably $R_4$ is methyl or ethyl; most preferably $R_4$ is methyl.

Preferably $R_5$ and $R_6$ are independently H, $C_1$-$C_6$ alkyl, $C_1$-$C_6$ haloalkyl or $C_3$-$C_6$ cycloalkyl.

More preferably $R_5$ and $R_6$ are independently $C_1$-$C_4$ alkyl or $C_1$-$C_4$ haloalkyl.

Most preferably $R_5$ is $C_1$-$C_2$ alkyl and $R_6$ is $C_1$-$C_2$ fluoroalkyl.

Also preferred is when $R_5$ is methyl and $R_6$ is —$CF_3$ or —$CH_2CF_3$.

Preferably $R_7$ is $C_1$-$C_6$ alkyl, $C_1$-$C_6$ haloalkyl or $C_3$-$C_6$ cycloalkyl.

More preferably $R_7$ is $C_1$-$C_4$ alkyl or $C_1$-$C_4$ haloalkyl Most preferably $R_7$ is $C_1$-$C_2$ fluoroalkyl.

Also preferred is when $R_7$ is —$CF_3$ or —$CH_2CF_3$.

Further embodiments according to the invention are provided as set forth below.

A preferred group of compounds of formula I is represented by the compounds of formula I-A1

I-A1

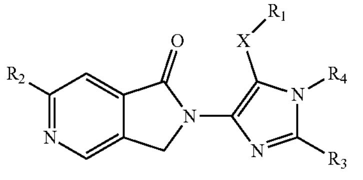

wherein $R_1$, $R_2$, $R_3$, X, $R_4$, $R_5$, $R_6$, and $R_7$ are as defined under formula I above; or an agrochemically acceptable salt, stereoisomer, enantiomer, tautomer or N-oxide of a compound of formula I-A1.

In one preferred group of compounds of formula I-A1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy;

and wherein X is S, SO, or $SO_2$; $R_1$ is $C_1$-$C_4$ alkyl or $C_3$-$C_6$ cycloalkyl-$C_1$-$C_4$ alkyl;

$R_4$ is $C_1$-$C_4$ alkyl; $R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —$CO(NR_5R_6)$, —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl-; $R_5$ and $R_6$ are independently H, $C_1$-$C_6$ alkyl, $C_1$-$C_6$ haloalkyl or $C_3$-$C_6$ cycloalkyl; and $R_7$ is $C_1$-$C_6$ alkyl, $C_1$-$C_6$ haloalkyl or $C_3$-$C_6$ cycloalkyl.

In another preferred group of compounds of formula, I-A1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy;

and wherein; X is S, SO, or $SO_2$; $R_1$ is $C_1$-$C_4$ alkyl, or $C_3$-$C_6$ cycloalkyl-$C_1$-$C_4$ alkyl;

$R_4$ is $C_1$-$C_4$ alkyl; and $R_3$ is a five- to six-membered saturated, partially saturated, aromatic ring or heteroaromatic ring system, linked via a ring carbon atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl-, and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom.

In another further preferred group of compounds of formula I-A1, $R_3$ is a five-membered heteroaromatic ring system linked via a ring nitrogen atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano and $C_1$-$C_6$ cyanoalkyl; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom.

In the compounds of formula I-A1 and all of the preferred embodiments of compounds of formula I-A1 mentioned above, unless otherwise specified, $R_1$, $R_2$, $R_3$, X, $R_4$, $R_5$, $R_6$ and $R_7$ are as defined under formula I above; preferably $R_1$ is ethyl or cyclopropylmethyl; most preferably $R_1$ is ethyl; preferably $R_2$ is —$OSO_2CF_3$, $SO_2CF_3$, —$OCF_3$, $CF_2CF_3$ or $CF_3$; more preferably $R_2$ is —$OCF_3$, —$CF_2CF_3$ or —$CF_3$; most preferably $R_2$ is —$CF_3$ or —$OCF_3$; preferably X is S or $SO_2$; most preferably X is $SO_2$; preferably $R_4$ is methyl or ethyl; most preferably $R_4$ is methyl; preferably $R_3$ is selected from hydrogen; halogen; cyclopropyl; cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —$(CH_2)$—cyclopropyl, —$(CH_2)$-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

Another preferred group of compounds of formula I is represented by the compounds of formula I-B1

I-B1

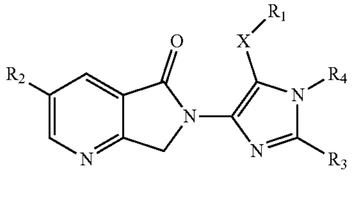

wherein $R_1$, $R_2$, $R_3$, X, $R_4$, $R_5$, $R_6$, and $R_7$ are as defined under formula I above; or an agrochemically acceptable salt, stereoisomer, enantiomer, tautomer or N-oxide of a compound of formula I-B1.

In one preferred group of compounds of formula I-B1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy;

and wherein X is S, SO, or $SO_2$; $R_1$ is $C_1$-$C_4$ alkyl or $C_3$-$C_6$ cycloalkyl-$C_1$-$C_4$ alkyl;

$R_4$ is $C_1$-$C_4$ alkyl; $R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —CO($NR_5R_6$), —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl-; $R_5$ and $R_6$ are independently H, $C_1$-$C_6$ alkyl, $C_1$-$C_6$ haloalkyl, $C_3$-$C_6$ cycloalkyl; and $R_7$ is $C_1$-$C_6$ alkyl, $C_1$-$C_6$ haloalkyl, $C_3$-$C_6$ cycloalkyl.

In another preferred group of compounds of formula, I-B1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy; and wherein; X is S, SO, or $SO_2$; $R_1$ is $C_1$-$C_4$ alkyl, or $C_3$-$C_6$ cycloalkyl-$C_1$-$C_4$ alkyl;

$R_4$ is $C_1$-$C_4$ alkyl; and $R_3$ is a five- to six-membered saturated, partially saturated, aromatic ring or heteroaromatic ring system, linked via a ring carbon atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$) alkyl- or ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom.

In another further preferred group of compounds of formula I-B1, $R_3$ is a five-membered heteroaromatic ring system linked via a ring nitrogen atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$—$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom.

In compounds of formula I-B1 and all of the preferred embodiments of compounds of formula I-B1 mentioned above, unless otherwise specified, $R_1$, $R_2$, $R_3$, X, $R_4$, $R_5$, $R_6$ and $R_7$ are as defined under formula I above; preferably $R_1$ is ethyl or cyclopropylmethyl; most preferably $R_1$ is ethyl; preferably $R_2$ is —$OSO_2CF_3$, $SO_2CF_3$, —$OCF_3$, $CF_2CF_3$ or $CF_3$; more preferably $R_2$ is —$OCF_3$, —$CF_2CF_3$ or —$CF_3$; most preferably $R_2$ is —$CF_3$ or —$OCF_3$; preferably X is S or $SO_2$; most preferably X is $SO_2$; preferably $R_4$ is methyl or ethyl; most preferably $R_4$ is methyl; preferably $R_3$ is selected from hydrogen; halogen; cyclopropyl; cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —($CH_2$)-cyclopropyl, —($CH_2$)-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

Another preferred group of compounds of formula I is represented by the compounds of formula I-C1

I-C1

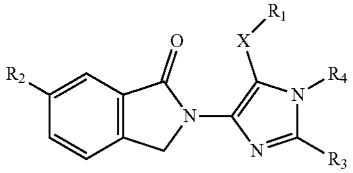

wherein $R_1$, $R_2$, $R_3$, X, $R_4$, $R_5$, $R_6$, and $R_7$ are as defined under formula I above; or an agrochemically acceptable salt, stereoisomer, enantiomer, tautomer or N-oxide of a compound of formula I-C1.

In one preferred group of compounds of formula I-C1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy; and wherein X is S, SO, or $SO_2$; $R_1$ is $C_1$-$C_4$ alkyl, or $C_3$-$C_6$ cycloalkyl-$C_1$-$C_4$ alkyl;

$R_4$ is $C_1$-$C_4$ alkyl; $R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —CO($NR_5R_6$), —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl-; $R_5$ and $R_6$ are independently H, $C_1$-$C_6$ alkyl, $C_1$-$C_6$ haloalkyl, $C_3$-$C_6$ cycloalkyl; and $R_7$ is $C_1$-$C_6$ alkyl, $C_1$-$C_6$ haloalkyl, $C_3$-$C_6$ cycloalkyl.

In another preferred group of compounds of formula I-C1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy;

and wherein; X is S, SO, or $SO_2$; $R_1$ is $C_1$-$C_4$ alkyl or $C_3$-$C_6$ cycloalkyl-$C_1$-$C_4$ alkyl;

$R_4$ is $C_1$-$C_4$ alkyl; $R_3$ is a five- to six-membered saturated, partially saturated, aromatic ring or heteroaromatic ring system, linked via a ring carbon atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom;

In another further preferred group of compounds of formula I-C1, $R_3$ is a five-membered aromatic ring system linked via a ring nitrogen atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- or ($C_3$-$C_8$)cycloalkyl monosubstituted by cyano-($C_1$-$C_6$)alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom.

In the compounds of formula I-C1 and all of the preferred embodiments of compounds of formula I-C1 mentioned above, unless otherwise specified, $R_1$, $R_2$, $R_3$, X, $R_4$, $R_5$, $R_6$ and $R_7$ are as defined under formula I above; preferably $R_1$ is ethyl or cyclopropylmethyl; most preferably $R_1$ is ethyl; preferably $R_2$ is —$OSO_2CF_3$, $SO_2CF_3$, —$OCF_3$, $CF_2CF_3$ or $CF_3$; more preferably $R_2$ is —$OCF_3$, —$CF_2CF_3$ or —$CF_3$; most preferably $R_2$ is —$CF_3$ or —$OCF_3$; preferably X is S or $SO_2$; most preferably X is $SO_2$; preferably $R_4$ is methyl or ethyl; most preferably $R_4$ is methyl; preferably $R_3$ is selected from hydrogen; halogen; cyclopropyl; cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —($CH_2$)-cyclopropyl, —($CH_2$)-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

Another preferred group of compounds of formula I is represented by the compounds of formula I-D1

I-D1

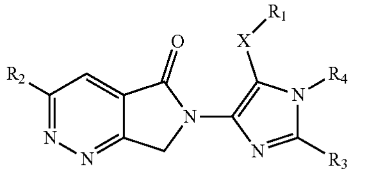

wherein $R_1$, $R_2$, $R_3$, X, $R_4$, $R_5$, $R_6$, and $R_7$ are as defined under formula I above; or an agrochemically acceptable salt, stereoisomer, enantiomer, tautomer or N-oxide of a compound of formula I-D1.

In one preferred group of compounds of formula I-D1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy; and wherein X is S, SO, or $SO_2$; $R_1$ is $C_1$-$C_4$ alkyl or $C_3$-$C_6$ cycloalkyl-$C_1$-$C_4$ alkyl;

$R_4$ is $C_1$-$C_4$ alkyl and $R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —$CO(NR_5R_6)$, —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl-; $R_5$ and RB are independently H, $C_1$-$C_6$ alkyl, $C_1$-$C_6$ haloalkyl, $C_3$-$C_6$ cycloalkyl; and $R_7$ is $C_1$-$C_6$ alkyl, $C_1$-$C_6$ haloalkyl or $C_3$-$C_6$ cycloalkyl.

In another preferred group of compounds of formula I-D1, $R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl, $C_1$-$C_6$ haloalkoxy or $C_1$-$C_4$ haloalkylsulfonyloxy; and wherein; X is S, SO, or $SO_2$; $R_1$ is $C_1$-$C_4$ alkyl or $C_3$-$C_6$ cycloalkyl-$C_1$-$C_4$ alkyl;

$R_4$ is $C_1$-$C_4$ alkyl and $R_3$ is a five- to six-membered saturated, partially saturated, aromatic ring or heteroaromatic ring system, linked via a ring carbon atom to the imidazole ring which is connected to the substitutent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$) alkyl- and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom.

In another further preferred group of compounds of formula I-D1, $R_3$ is a five-membered aromatic ring system linked via a ring nitrogen atom to the imidazole ring which is connected to the substituent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$) alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom.

In the compounds of formula I-D1 and all of the preferred embodiments of compounds of formula I-D1 mentioned above, unless otherwise specified, $R_1$, $R_2$, $R_3$, X, $R_4$, $R_5$, $R_6$ and $R_7$ are as defined under formula I above; preferably $R_1$ is ethyl or cyclopropylmethyl; most preferably $R_1$ is ethyl; preferably $R_2$ is —$OSO_2CF_3$, $SO_2CF_3$, —$OCF_3$, $CF_2CF_3$ or $CF_3$; more preferably $R_2$ is —$OCF_3$, —$CF_2CF_3$ or —$CF_3$; most preferably $R_2$ is —$CF_3$ or —$OCF_3$; preferably X is S or $SO_2$; most preferably X is $SO_2$; preferably $R_4$ is methyl or ethyl; most preferably $R_4$ is methyl; preferably $R_3$ is selected from hydrogen; halogen; cyclopropyl; cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —($CH_2$)-cyclopropyl, —($CH_2$)-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

An outstanding group of compounds according to the invention are those of formula I-E (I-E)

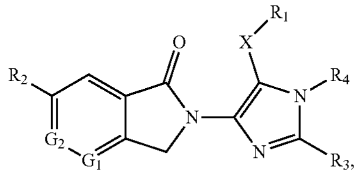

wherein $G_1$ and $G_2$ are, independently from each other, CH or N;

$R_1$ is $C_1$-$C_4$ alkyl or cyclopropyl-$C_1$-$C_4$ alkyl; preferably $R_1$ is ethyl or cyclopropylmethyl; more preferably $R_1$ is ethyl;

$R_2$ is $C_1$-$C_6$ haloalkyl, $C_1$-$C_4$ haloalkylsulfanyl, $C_1$-$C_4$ haloalkylsulfinyl, $C_1$-$C_4$ haloalkylsulfonyl or $C_1$-$C_6$ haloalkoxy, preferably $R_2$ is $CF_3$, $CF_2CF_3$, $SCF_3$, $SOCF_3$, $SO_2CF_3$ or $OCF_3$; more preferably $R_2$ is —$OCF_3$, —$CF_2CF_3$ or —$CF_3$; most preferably $R_2$ is —$CF_3$ or —$OCF_3$;

and wherein

X is S, SO, or $SO_2$, preferably X is S or $SO_2$, even more preferably X is $SO_2$;

$R_4$ is $C_1$-$C_6$ alkyl; preferably $R_4$ is methyl or ethyl;

$R_3$ is hydrogen, halogen, $C_1$-$C_4$ alkyl, $C_1$-$C_6$ haloalkyl, $C_3$-$C_6$ cycloalkyl, $C_3$-$C_6$ cycloalkyl monosubstituted by cyano, $C_1$-$C_6$ cyanoalkyl, $C_1$-$C_6$ alkoxy, $C_1$-$C_6$ haloalkoxy, —$CO(NR_5R_6)$, —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl-; or $R_3$ is a five- to six-membered saturated, partially saturated, aromatic ring or heteroaromatic ring system, linked via a ring carbon atom to the imidazole ring which is connected to the substituent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom; or $R_3$ is a five-membered aromatic ring system linked via a ring nitrogen atom to the imidazole ring which is connected to the substituent $R_4$, said ring system is unsubstituted or is mono- or polysubstituted by substituents selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl, $C_1$-$C_4$ alkylsulfonyl, $C_3$-$C_6$ cycloalkyl, $C_3$-$C_6$ cycloalkyl monosubstituted by cyano, $C_1$-$C_6$ cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom;

$R_5$ and $R_6$ are independently H, $C_1$-$C_6$ alkyl, $C_1$-$C_6$ haloalkyl or $C_3$-$C_6$ cycloalkyl; preferably $R_5$ and $R_6$ are independently $C_1$-$C_4$ alkyl or $C_1$-$C_4$ haloalkyl; more preferably $R_5$ is $C_1$-$C_2$ alkyl and $R_6$ is $C_1$-$C_2$ fluoroalkyl; and $R_7$ is $C_1$-$C_6$ alkyl, $C_1$-$C_6$ haloalkyl or $C_3$-$C_6$ cycloalkyl; preferably $R_7$ is $C_1$-$C_4$ alkyl or $C_1$-$C_4$ haloalkyl; more preferably $R_7$ is $C_1$-$C_2$ fluoroalkyl; or an agrochemically acceptable salt, stereoisomer, enantiomer, tautomer or N-oxide of a compound of formula I-E.

One preferred group of compounds according to this embodiment are compounds of formula (I-E-1) which are compounds of formula (I-E), or any of the preferred embodiments of compounds of formula (I-E), wherein preferably $R_3$ is selected from the group consisting of hydrogen; halogen; cyclopropyl; cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —($CH_2$)-cyclopropyl, —($CH_2$)-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

Another preferred group of compounds according to this embodiment are compounds of formula (I-E-2) which are compounds of formula (I-E), or any of the preferred embodiments of compounds of formula (I-E), wherein preferably $R_3$ is selected from the group consisting of halogen; cyclopropyl; 1-cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —($CH_2$)-cyclopropyl, —($CH_2$)-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

Another preferred group of compounds according to this embodiment are compounds of formula (I-E-3) which are compounds of formula (I-E), or any of the preferred embodiments of compounds of formula (I-E), wherein $R_3$ is selected from the group consisting of —$OCH_2CF_3$; —$N(CH_3)COCH_2CF_3$; —$CON(CH_3)CH_2CF_3$; 3-chloro-pyrazol-1-yl; 3-cyclopropyl-pyrazol-1-yl; 4-(1-cyanocyclopropyl)phenyl; 3-(1-cyanocyclopropyl)phenyl; pyrimidin-5-yl; 1-cyclopropylpyrazol-4-yl; cyclopropyl; 1-difluoromethylpyrazol-4-yl; 1-(2,2-difluoroethyl)pyrazol-4-yl; 3-cyclopropyl-4,5-dihydro-isoxazol-5-yl; 3-trifluoromethyl-pyrazol-1-yl; and 1-(1-cyanocyclopropylmethyl)pyrazol-4-yl.

A further preferred group of compounds according to this embodiment are compounds of formula (I-E-4) which are compounds of formula (I-E), or any of the preferred embodiments of compounds of formula (I-E), wherein preferably $G_1$ and $G_2$ are N.

One further preferred group of compounds according to this embodiment are compounds of formula (I-E-5) which are compounds of formula (I-E), or any of the preferred embodiments of compounds of formula (I-E), wherein preferably $G_1$ is N and $G_2$ is CH.

One further preferred group of compounds according to this embodiment are compounds of formula (I-E-6) which are compounds of formula (I-E), or any of the preferred embodiments of compounds of formula (I-E), wherein preferably $G_1$ is CH and $G_2$ is N.

One further preferred group of compounds according to this embodiment are compounds of formula (I-E-7) which are compounds of formula (I-E), or any of the preferred embodiments of compounds of formula (I-E), wherein preferably both $G_1$ and $G_2$ are CH.

Another outstanding group of compounds according to the invention are those of formula I-F

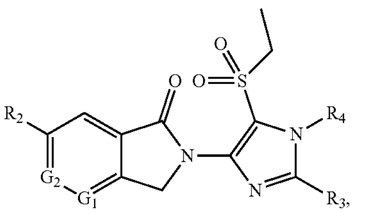

(I-F)

wherein $G_1$ is N and $G_2$ is CH; or both $G_1$ and $G_2$ are CH;

$R_2$ is $C_1$-$C_6$ haloalkyl or $C_1$-$C_6$ haloalkoxy; preferably $R_2$ is $CF_3$, $CF_2CF_3$ or $OCF_3$; even more preferably $R_2$ is $CF_3$ or $OCF_3$;

$R_4$ is $C_1$-$C_6$ alkyl; preferably $R_4$ is methyl or ethyl; even more preferably $R_4$ is methyl; and $R_3$ is selected from the group consisting of cyclopropyl; $C_1$-$C_6$ haloalkoxy, preferably trifluoroethoxy; phenyl which can be mono-substituted by cyanocyclopropyl; C-linked pyrimidinyl; N-linked pyrazolyl which can be mono-substituted by chloro, cyclopropyl or trifluoromethyl; C-linked pyrazolyl which is N-substituted by cyclopropyl, $—CHF_2$, $—CH_2CHF_2$, $—CH_2CF_3$, $—(CH_2)$-cyclopropyl, or $—(CH_2)$-cyanocyclopropyl; and C-linked dihydroisoxazole which can be mono-substituted by cyclopropyl.

One preferred group of compounds according to this embodiment are compounds of formula (I-F-1) which are compounds of formula (I-F), or any of the preferred embodiments of compounds of formula (I-F), wherein $R_3$ is selected from the group consisting of cyclopropyl; $—OCH_2CF_3$; 4-(1-cyanocyclopropyl)phenyl; 3-(1-cyanocyclopropyl)phenyl; pyrimidin-5-yl; pyrimidin-2-yl; 3-chloro-pyrazol-1-yl; 4-chloro-pyrazol-1-yl; 3-cyclopropyl-pyrazol-1-yl; 4-cyclopropyl-pyrazol-1-yl; 3-trifluoromethyl-pyrazol-1-yl; 4-trifluoromethyl-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)pyrazol-4-yl; and 3-cyclopropyl-4,5-dihydro-isoxazol-5-yl.

Another preferred group of compounds according to this embodiment are compounds of formula (I-F-2) which are compounds of formula (I-F), or any of the preferred embodiments of compounds of formula (I-F), wherein $R_3$ is selected from the group consisting of cyclopropyl; $—OCH_2CF_3$; 4-(1-cyanocyclopropyl)phenyl; pyrimidin-5-yl; pyrimidin-2-yl; 3-chloro-pyrazol-1-yl; 3-cyclopropyl-pyrazol-1-yl; 4-trifluoromethyl-pyrazol-1-yl; 1-cyclopropylpyrazol-4-yl; 1-difluoromethylpyrazol-4-yl; 1-(2,2-difluoroethyl)pyrazol-4-yl; 1-(2,2,2-trifluoroethyl)pyrazol-4-yl; 1-cyclopropylmethylpyrazol-4-yl; 1-(1-cyanocyclopropylmethyl)pyrazol-4-yl; and 3-cyclopropyl-4,5-dihydro-isoxazol-5-yl.

One further preferred group of compounds according to this embodiment are compounds of formula (I-F-3) which are compounds of formula (I-F), or any of the preferred embodiments of compounds of formula (I-F), wherein preferably $G_1$ is N and $G_2$ is CH.

One further preferred group of compounds according to this embodiment are compounds of formula (I-F-4) which are compounds of formula (I-F), or any of the preferred embodiments of compounds of formula (I-F), wherein preferably both $G_1$ and $G_2$ are CH.

Compounds according to the invention may possess any number of benefits including, inter alia, advantageous levels of biological activity for protecting plants against insects or superior properties for use as agrochemical active ingredients (for example, greater biological activity, an advantageous spectrum of activity, an increased safety profile, improved physico-chemical properties, or increased biodegradability or environmental profile). In particular, it has been surprisingly found that certain compounds of formula (I) may show an advantageous safety profile with respect to non-target arthropods, in particular pollinators such as honey bees, solitary bees, and bumble bees. Most particularly, *Apis mellifera.*

In another aspect the present invention provides a composition comprising an insecticidally, acaricidally, nematicidally or molluscicidally effective amount of a compound of formula (I), or an agrochemically acceptable salt, stereoisomer, enantiomer, tautomer or N-oxide thereof, as defined in any of the embodiments under compounds of formula (I-A1), (I-B1), (I-C1), (I-D1), (I-E), and (I-F) (above), and, optionally, an auxiliary or diluent.

In a further aspect the present invention provides a method of combating and controlling insects, acarines, nematodes or molluscs which comprises applying to a pest, to a locus of a pest, or to a plant susceptible to attack by a pest an insecticidally, acaricidally, nematicidally or molluscicidally effective amount of a compound of formula (I), or an agrochemically acceptable salt, stereoisomer, enantiomer, tautomer or N-oxide thereof, as defined in any of the embodiments under compounds of formula (I-A1), (I-B1), (I-C1), (I-D1), (I-E), and (I-F) (above) or a composition as defined above.

In a yet further aspect, the present invention provides a method for the protection of plant propagation material from the attack by insects, acarines, nematodes or molluscs, which comprises treating the propagation material or the site, where the propagation material is planted, with a composition as defined above.

The process according to the invention for preparing compounds of formula I is carried out by methods known to those skilled in the art. Compounds of formula I-a3, wherein X is $SO_2$ and $G_1$, $G_2$, $R_1$, $R_2$, $R_3$, $R_4$, $R_5$, $R_6$, and $R_7$ are defined as under formula I above, may be prepared by oxidation of compounds of formula I-a2, wherein X is SO and $G_1$, $G_2$, $R_1$, $R_2$, $R_3$, $R_4$, $R_5$, $R_6$, and $R_7$ are defined as under formula I above. The reaction can be performed with reagents such as a peracid, for example peracetic acid or m-chloroperbenzoic acid, or a hydroperoxide, as for example, hydrogen peroxide or tert-butylhydroperoxide, or an inorganic oxidant, such as a monoperoxo-disulfate salt or potassium permanganate. In a similar way, compounds of formula I-a2, wherein X is SO and $G_1$, $G_2$, $R_1$, $R_2$, $R_3$, $R_4$, $R_5$, $R_6$, and $R_7$ are defined as under formula I above, may be prepared by oxidation of compounds of formula I-a1, wherein X is S and $G_1$, $G_2$, $R_1$, $R_2$, $R_3$, $R_4$, $R_5$, $R_6$, and $R_7$ are defined as under formula I above, under analogous conditions described above. These reactions can be performed in various organic or aqueous solvents compatible to these conditions, by temperatures from below 0° C. up to the boiling point of the solvent system. The transformation of compounds of the formula I-a1 into compounds of the formula I-a2 and I-a3 is represented in Scheme 1.

Scheme 1
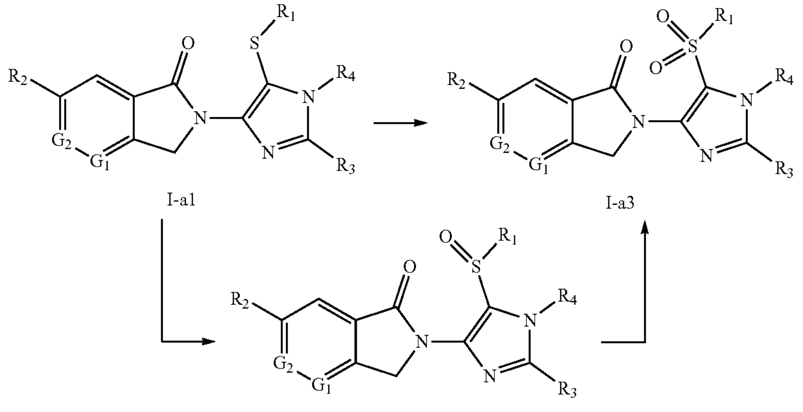
Compounds of formula I wherein X, $G_1$, $G_2$, $R_1$, $R_2$, $R_3$, $R_4$, $R_5$, $R_6$, and $R_7$ are defined as under formula I above,
Scheme 2
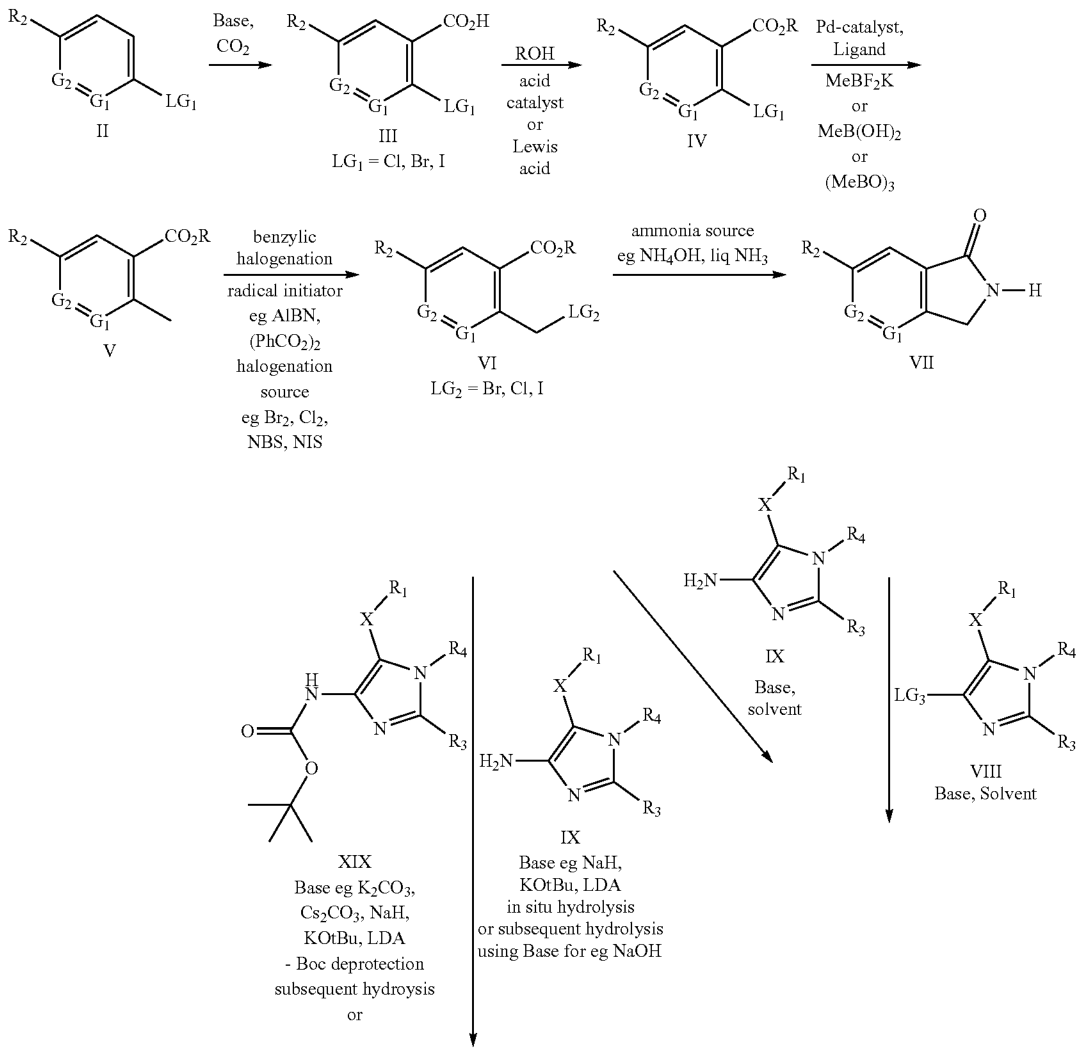

-continued

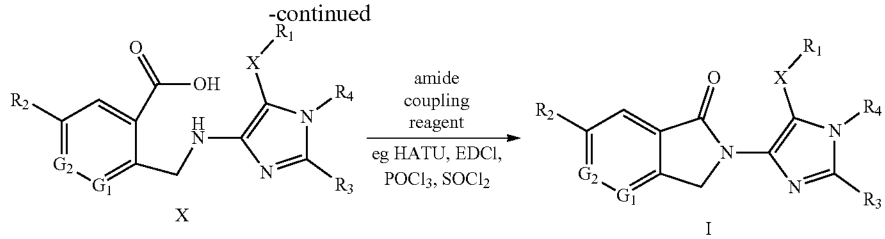

X I may be prepared by reacting compounds of formula VII, wherein $R_2$, $G_1$, and $G_2$ are defined in formula I above and compounds of formula VIII, wherein $R_1$, X, $R_3$, $R_4$, $R_5$, $R_6$, and $R_7$ is as defined in formula I above and in which $LG_3$ is a halogen (or a pseudo-halogen leaving group, such as a triflate), in the presence of a base, such as sodium carbonate, potassium carbonate or cesium carbonate, or sodium hydride, in an appropriate solvent such as for example tetrahydrofuran, dioxane, N,N-dimethylformamide, N,N-dimethylacetamide or acetonitrile, at temperatures between 0 and 150° C., optionally under microwave irradiation (scheme 2).

Alternatively compounds of formula I wherein $G_1$, $G_2$, $R_1$, X, $R_2$, $R_3$, $R_4$, $R_5$, $R_6$, and $R_7$ are defined as under formula I above may be prepared by reacting compounds of formula VII, wherein $R_2$, $G_1$, and $G_2$ are defined as formula I above and compounds of formula VIII, wherein $R_1$, X, $R_3$, $R_4$, $R_5$, $R_6$, and $R_7$ is as defined in formula I above and in which $LG_3$ is a halogen (or a pseudo-halogen leaving group, such as a triflate), preferably bromo or iodo in the presence of a base, such as sodium carbonate, potassium carbonate or cesium carbonate, or potassium tert-butoxide in the presence of a metal catalyst either copper catalyst for example copper (I) iodide, optionally in the presence of a ligand for example diamine ligands (e.g. N,N'-dimethylethylenediamine or trans-cyclohexyldiamine) or dibenzylideneacetone (dba), or 1,10-phenanthroline, at temperatures between 30-180° C., optionally under microwave irradiation or palladium catalyst for example palladium(II)acetate, bis(dibenzylideneacetone)palladium(0) ($Pd(dba)_2$) or tris(dibenzylideneacetone) dipalladium(0) ($Pd_2(dba)_3$, optionally in form of a chloroform adduct), or a palladium pre-catalyst such as for example tert-BuBrettPhos Pd G3 [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd $G_3$ [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation. The above reaction may be carried out in the presence of solvent such as toluene, dimethylformamide DMF, N-methyl pyrrolidine NMP, dimethyl sulfoxide DMSO, dioxane, tetrahydrofuran THE and are described in literature for example in WO2012031004, WO2009042907 and Synthetic Communications, 41: 67-72, 2011.

Alternatively compounds of formula I wherein $G_1$, $G_2$, $R_1$, X, $R_2$, $R_3$, $R_4$, $R_5$, $R_6$, and $R_7$ are defined as under formula I above may be prepared by reacting compounds of formula VI, wherein $R_2$, $G_1$ and $G_2$ are as defined in formula I above and $LG_2$ is a leaving group for example Br, Cl or I, preferably bromo and R is $C_1$-$C_6$ alkyl, benzyl or a phenyl group and compounds of formula IX, wherein $R_1$, X, $R_3$, $R_4$, $R_5$, $R_6$, and $R_7$ are as defined in formula I above in the presence of base such as such as sodium carbonate, potassium carbonate or cesium carbonate, or sodium hydride, N,N-diisopropylethylamine or KOtBu and in the presence of solvent such as ethanol, methanol, dioxane, toluene, acetonitrile, DMF, DMA, DMSO, THE at temperatures between 0 and 150° C., optionally under microwave irradiation. Such reactions proceed via nucleophilic substitution and subsequent cyclization and are also reported in literature for example in WO2009042907.

Alternatively compounds of formula I wherein X, $R_2$, $G_1$, $G_2$, $R_1$, $R_3$, $R_4$, $R_5$, $R_6$, and $R_7$ are as defined in formula I above can be prepared (scheme 2) by cyclizing compounds of formula X, wherein X, $R_2$, $G_1$, $G_2$, $R_1$, $R_3$, $R_4$, $R_5$, $R_6$, and $R_7$ are as defined in formula I, for example in the presence of phosphorus oxychloride oxychloride (other amide coupling reagent may also be used, such as thionyl chloride $SOCl_2$, HATU or EDCl), optionally in the presence of a base, such as triethylamine, pyridine or Hunig's base, optionally in the presence of a solvent or diluent, such as toluene or xylene, at temperatures between 0 and 180° C., preferably between 20 and 120° C.

Compounds of formula I, wherein X, $R_2$, $G_1$, $G_2$, $R_1$, $R_3$, $R_4$, $R_5$, $R_6$, and $R_7$ are as under formula I above, Scheme 3

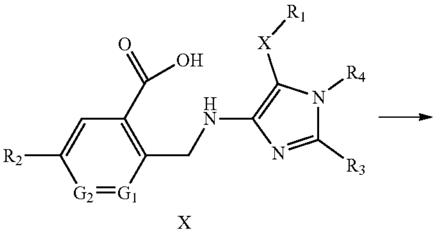

X

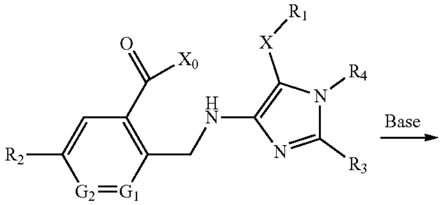

Xa

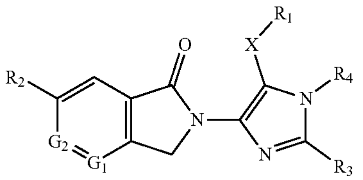

I

-continued

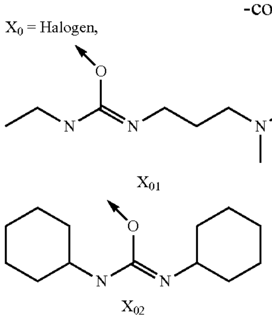

can also be prepared (scheme 3) by cyclization of the formula Xa wherein X, $R_2$, $G_1$, $G_2$, $R_1$, $R_3$, $R_4$, $R_5$, $R_6$, and $R_7$ are as under formula I above and in which $X_0$ is halogen, preferably chlorine, or $X_0$ is either $X_{01}$ or $X_{02}$, in the presence of a base, such as triethylamine, N,N-diisopropylethylamine or pyridine, optionally in the presence of a catalyst (such as 4-dimethylaminopyridine DMAP), in an inert solvents such as dichloromethane, tetrahydrofuran, dioxane, N,N-dimethylformamide, N,N-dimethylacetamide, acetonitrile, ethyl acetate or toluene, at temperatures between 0 and 50° C. Certain bases, such as pyridine and triethylamine, may be employed successfully as both base and solvent.

Compounds of formula Xa, wherein X, $R_2$, $G_1$, $G_2$, $R_1$, $R_3$, $R_4$, $R_5$, $R_6$, and $R_7$ are as under formula I above and in which $X_0$ is halogen, preferably chlorine, or $X_0$ is either $X_{01}$ or $X_{02}$, can be prepared by activation of compound of formula X, wherein $R_2$, $G_1$, $G_2$, X, $R_1$, $R_3$, $R_4$, $R_5$, $R_6$ and $R_7$ are defined as under formula I above, by methods known to those skilled in the art and described in, for example, Tetrahedron, 2005, 61 (46), 10827-10852. Preferred is the formation of an activated species Xa, wherein $R_2$, $G_1$, $G_2$, X, $R_1$, $R_3$, $R_4$, $R_5$, $R_6$ and $R_7$ are defined as under formula I above and in which $X_0$ is halogen, preferably chlorine. For example, compounds Xa where $X_0$ is halogen, preferably chlorine, are formed by treatment of X with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula X with, for example, 1-ethyl-3-(3-dimethylamino-propyl)carbo-diimide EDC or dicyclohexyl carbodiimide DCC will generate an activated species Xa, wherein $X_0$ is $X_{01}$ or $X_{02}$ respectively, in an inert solvent, such as pyridine or tetrahydrofuran THF, optionally in the presence of a base, such as triethylamine, at temperatures between 50-180° C.

Compounds of formula VII, wherein $R_2$, $G_1$ and $G_2$ are as defined in formula I above can be prepared by reacting compounds of formula VI, wherein $R_2$, $G_1$ and $G_2$ are as defined in formula I above and $LG_2$ is a leaving group for example Br, Cl or I, preferably bromo and R is $C_1$-$C_6$ alkyl, benzyl or a phenyl group with ammonia or surrogates of ammonia for example $NH_4OH$ in the presence of solvent such as ethanol, methanol, dioxane, toluene, DMF, DMA, DMSO, THE at temperatures between 0 and 150° C., optionally under microwave irradiation.

Compounds of formula X, wherein X, $R_2$, $G_1$, $G_2$, $R_1$, $R_3$, $R_4$, $R_5$, $R_6$, and $R_7$ are as under formula I above, can be prepared by nucleophilic substitution reaction of compound of formula VI, wherein $R_2$, $G_1$ and $G_2$ are as defined in formula I above and $LG_2$ is a leaving group for example Br, Cl or I, preferably bromo and R is $C_1$-$C_6$ alkyl, benzyl or a phenyl group, with amino compound of formula IX, wherein $R_1$, X, $R_3$, $R_4$, $R_5$, $R_6$ and $R_7$ are as defined in formula I above, under conditions described above, followed by in situ hydrolysis of the formed intermediate ester of formula XVII, wherein $R_2$, $G_1$, $G_2$, X, $R_1$, $R_3$, $R_4$, $R_5$, $R_6$ and $R_7$ are defined as under formula I above, and in which R is $C_1$-$C_6$ alkyl, benzyl or a phenyl group.

(XVII)

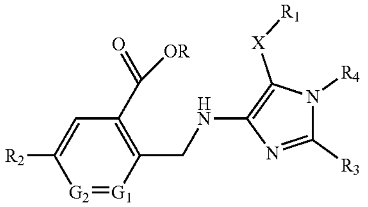

The in situ generated unhydrolyzed ester compound of formula XVII may be isolated and can also be converted via saponification reaction, in the presence of suitable base for example sodium hydroxide NaOH, lithium hydroxide LiOH, or barium hydroxide $Ba(OH)_2$, in the presence of a solvent such as ethanol, methanol, dioxane, tetrahydrofuran or water (or mixtures thereof), to form the carboxylic acid of formula X. Alternatively, Krapcho-type conditions (e.g. heating the substrate XVII in the presence of sodium or lithium chloride in N-methyl pyrrolidone or aqueous dimethylsulfoxide DMSO, optionally under microwave irradiation) can also be used to convert compounds of formula XVII into compounds of formula X. The direct conversion of compound of formula VI to compound of formula X can be carried out in the presence of base such as sodium hydride, KOtBu, butyllithium, lithium diisopropylamide amongst others and in the presence of solvent such as dioxane, DMF, DMA, DMSO, THE at temperatures between −30 and 150° C.

The above reaction for the preparation of compounds of formula X can also be carried out by reacting compounds of formula VI, with compounds of formula IXa, wherein $R_1$, X, $R_3$, $R_4$, $R_5$, $R_6$ and $R_7$ are as defined in formula I above, and PG is an amino protecting group, for example tert-butyloxycarbonyl (BOC) under similar conditions as described above (as for the preparation of compounds of formula X by reacting compounds of formula VI and compounds of formula IX), followed by deprotection of the amino protecting group PG.

(IXa)

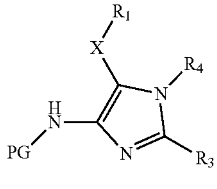

The deprotection of the amino protecting groups is well known to those skilled in the art, for example BOC protecting groups can be removed in the presence of acids such as hydrochloric acid, or trifluoroacetic acid, optionally in the presence of an inert solvent, such as dichloromethane, tetrahydrofuran, dioxane or benzotrifluoride, at temperatures between 0 and 70° C. This process of forming compounds of formula X (and I) from compounds of formula VI and IXa is detailed in scheme 2a and reflecting the particular situation wherein the group PG of IXa is tert-butyloxycarbonyl (BOC), defining compounds of formula XIX, wherein $R_1$, X, $R_3$, $R_4$, $R_5$, $R_6$ and $R_7$ are as defined in formula I above.

cyclization of compounds of formula XVII into compounds of formula I may be achieved under conditions mentioned below in scheme 7.

Scheme 2a (substituent definitions mentioned previously remain valid)

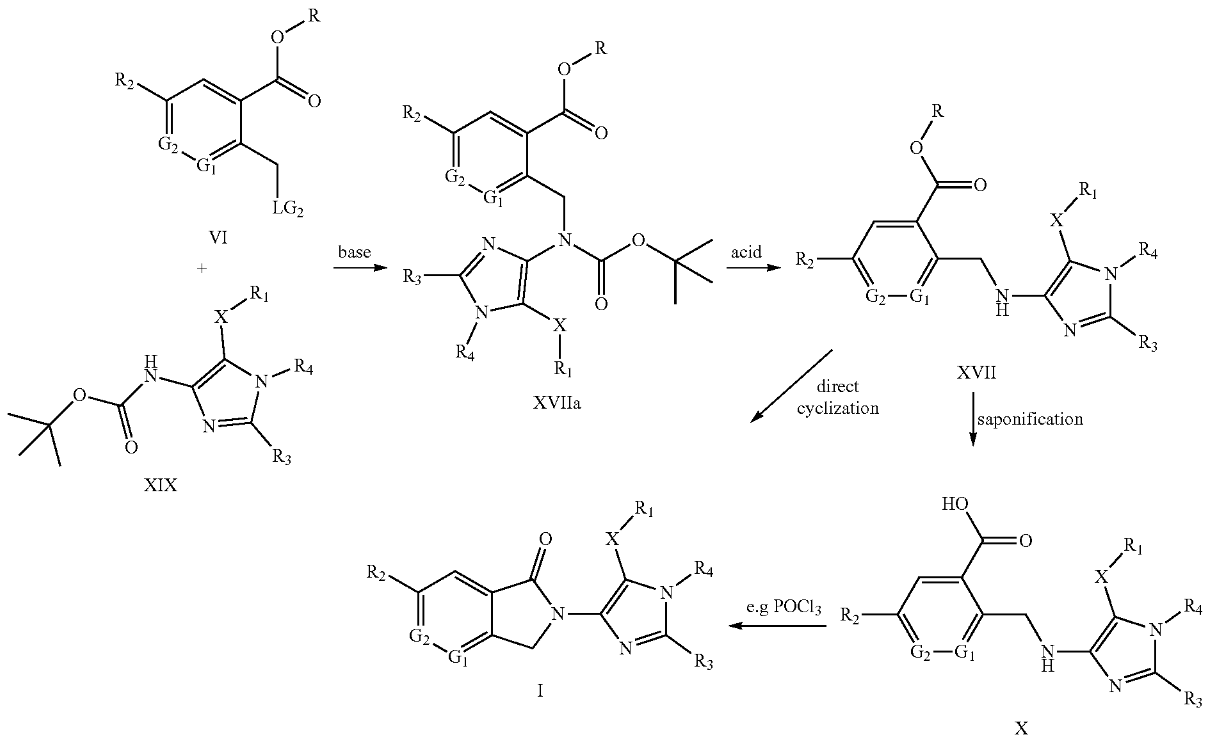

Compounds of formula VI and compounds of formula XIX react to compounds of formula XVIIa, in the presence of a base, such as sodium carbonate, potassium carbonate or cesium carbonate, or sodium hydride, or N,N-diisopropylethylamine or potassium tert-butoxide KOtBu, in the presence of a solvent such as ethanol, methanol, dioxane, toluene, acetonitrile, DMF, N,N-dimethylacetamide DMA, DMSO, or THF, at temperatures between 0 and 150° C., optionally under microwave irradiation. tert-Butyloxycarbonyl (BOC) group removal in compounds of formula XVIIa, mediated by acids, such as hydrochloric acid, or trifluoroacetic acid, optionally in the presence of an inert solvent, such as dichloromethane, tetrahydrofuran, dioxane or benzotrifluoride, at temperatures between 0 and 70° C., generates compounds of formula XVII. Saponification of compounds of formula XVII in the presence of a suitable base, for example sodium hydroxide NaOH, lithium hydroxide LiOH or barium hydroxide $Ba(OH)_2$, in the presence of a solvent such as ethanol, methanol, dioxane, tetrahydrofuran or water (or mixtures thereof), forms the carboxylic acids of formula X (alternatively, Krapcho-type conditions as described above may be used). Cyclization of compounds of formula X to compounds of formula I is achieved, for example, in the presence of phosphorus oxychloride (other amide coupling reagent may also be used, such as thionyl chloride $SOCl_2$, HATU or EDCl), optionally in the presence of a base, such as triethylamine, pyridine or Hunig's base, optionally in the presence of a solvent or diluent, such as toluene or xylene, at temperatures between 0 and 180° C., preferably between 20 and 120° C. Alternatively, a direct Compounds of formula VI, wherein $R_2$, $G_1$ and $G_2$ are as defined in formula I above, and $LG_2$ is a halogen leaving group, for example bromo Br, chloro Cl or iodo I (preferably bromo), and R is $C_1$-$C_6$ alkyl, benzyl or a phenyl group, are either known (see preparation descriptions disclosed in WO20/174094) or may be prepared by methods known to a person skilled in the art.

For example, compounds of formula VI, wherein $R_2$, $G_1$ and $G_2$ are as defined in formula I above and $LG_2$ is a leaving group for example Br, Cl or I, preferably bromo and R is $C_1$-$C_6$ alkyl, benzyl or a phenyl group can be prepared by radical induced benzylic halogenation of compounds of formula V, wherein $R_2$, $G_1$ and $G_2$ are as defined in formula I above, and R is $C_1$-$C_6$ alkyl, benzyl or a phenyl group. Such reaction are well known to those skilled in the art and may be carried out in the presence of electrophilic halogenating reagents such as $Br_2$, NBS, $Cl_2$, NIS amongst others and in the presence of radical initiator for example AIBN (Azobisisobutyronitrile), benzoyl peroxide or under photochemical conditions and at temperatures ranging from 20° C. to the boiling point of the reaction mixture and in the presence of solvent such as toluene, xylene, acetonitrile, hexane, dichloroethane, or carbon tetrachloride. Such reactions are known by the name of Wohl-Ziegler bromination and are reported in literature for example in *Synthesis*, 2015, 47, 1280-1290 and *J. Am. Chem. Soc.*, 1963, 85 (3), pp 354-355.

Compounds of formula V, wherein $R_2$, $G_1$ and $G_2$ are as defined in formula I above and R is $C_1$-$C_6$ alkyl, benzyl or phenyl group, may be prepared (scheme 2) by a Suzuki reaction, which involves for example, reacting compounds of formula IV, wherein $R_2$, $G_1$ and $G_2$ are as defined in formula I above, and $LG_1$ is a halogen Br, Cl, I (preferably Cl) and R is $C_1$-$C_6$ alkyl, benzyl or a phenyl group with trimethylboroxine or potassium methyltrifluoroborate amongst other methyl boronic acid equivalent. The reaction may be catalyzed by a palladium based catalyst, for example tetrakis(triphenyl-phosphine)palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)] palladium(II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Organomet. Chem. 576, 1999, 147-168.

Compounds of formula IV, wherein $R_2$, $G_1$ and $G_2$ are as defined in formula I above, and $LG_1$ is a halogen Br, Cl, I (preferably Cl) and R is $C_1$-$C_6$ alkyl, benzyl or a phenyl group can be prepared by reacting compounds of formula III, wherein $R_2$, $G_1$ and $G_2$ are as defined in formula I above, and $LG_1$ is a halogen Br, Cl, I (preferably Cl) and ROH, wherein R is $C_1$-$C_6$ alkyl, benzyl or a phenyl group, in the presence of acid catalyst for example sulfuric acid or Lewis acid for example $Sc(OTf)_3$ or $FeCl_3$. Such reactions are well known to those skilled in the state of art and known by the name of Fischer Esterification reaction and are reported in literature for example in *J. Org. Chem.,* 2006, 71, 3332-3334, *Chem. Commun.,* 1997, 351-352 and *Synthesis,* 2008, 3407-3410. Such esterification reaction can also be carried out by reacting compounds of formula III with $TMSCHN_2$ to form compounds of formula IV, wherein $R_2$, $G_1$ and $G_2$ are as defined in formula I above, and $LG_1$ is halogen Br, Cl, I (preferably Cl) and R is methyl, and are reported in *Angew. Chem. Int. Ed.* 2007, 46, 7075.

Compounds of formula III, wherein $R_2$, $G_1$ and $G_2$ are as defined in formula I above, and $LG_1$ is a halogen Br, Cl, I (preferably Cl) can be prepared by metalation reaction of compounds of formula II, wherein $R_2$, $G_1$ and $G_2$ are as defined in formula I above, and $LG_1$ is halogen Br, Cl, I (preferably Cl) with suitable base and subsequent reaction with carbon dioxide. Such metalation reaction can be performed using bases such as, for example, organolithium compounds, such as lithium tetramethylpiperidide, lithium diisopropylamide, or sec-BuLi amongst others, at temperatures ranging from −78 to 40° C., in the presence of solvent such as THF, DMPU, dioxane, or 2-Me-THF. Such reactions are reported in literature for example in Tetrahedron, 2004, 60(51), 11869-11874.

Alternatively, compounds of formula IV, wherein $R_2$, $G_1$ and $G_2$ are as defined in formula I above, and $LG_1$ is a halogen, for example Br, Cl or I (preferably Cl), and R is $C_1$-$C_6$ alkyl, benzyl or phenyl Scheme 2b

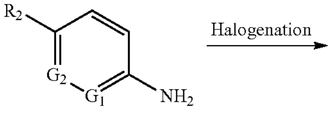

IV-c

-continued

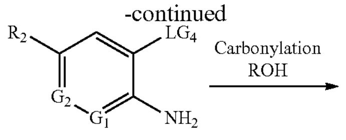

IV-b

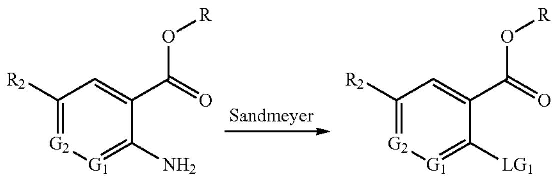

IV-a IV can be prepared (scheme 2b) by reacting compounds of formula IV-a, wherein $R_2$, $G_1$ and $G_2$ are as defined in formula I above, and R is $C_1$-$C_6$ alkyl, benzyl or phenyl, with a nitrite, such as tert-butyl nitrite t-BuONO, isoamyl nitrite, or sodium nitrite in the presence of a hydrohalic acid H-$LG_1$ and a copper salt Cu-$LG_1$, wherein $LG_1$ is halogen, for example Br, Cl or I (preferably Cl), under Sandmeyer-type reaction conditions. This transformation is preferably performed in an inert solvent, such as acetonitrile or a halogenated solvent like 1,2-dichloroethane, or water at temperatures between 0-150° C., preferably at temperatures ranging from room temperature to the boiling point of the reaction mixture.

Compounds of formula IV-a, wherein $R_2$, $G_1$ and $G_2$ are as defined in formula I above, and R is $C_1$-$C_6$ alkyl, benzyl or phenyl, can be prepared from compounds of formula IV-b, wherein $R_2$, $G_1$ and $G_2$ are as defined in formula I above, and $LG_4$ is a halogen, preferably Br, Cl or I, by methods found in, for example, WO 2016/020286 involving a carbonylation reaction, in which compounds of formula (IV-b) are reacted with carbon monoxide CO (usually under pressure), in presence of metal catalyst such as a palladium catalyst (for example: palladium(II) acetate), in an alcohol ROH solvent (optionally in presence of a co-solvent), wherein R is $C_1$-$C_6$ alkyl, benzyl or phenyl, and optionally in presence of a phosphine ligand, and optionally in presence of a base, at temperatures between 0-180° C.

Compounds of formula IV-b, wherein $R_2$, $G_1$ and $G_2$ are as defined in formula I above, and $LG_4$ is halogen, preferably Br, Cl or I, can be prepared by a halogenation reaction, which involves for example, reacting compounds of formula IV-c, wherein $R_2$, $G_1$ and $G_2$ are as defined in formula I above, with halogenating reagents, such as N-chlorosuccinimide (NCS), N-bromo-succinimide (NBS) or N-iodosuccinimide (NIS), or alternatively chlorine, bromine or iodine. Such halogenation reactions are carried out in an inert solvent, such as chloroform, carbon tetrachloride, 1,2-dichloroethane, acetic acid, ethers, acetonitrile or N,N-dimethylformamide, at temperatures between 20-200° C., preferably room temperature to 100° C.

Alternatively compounds of formula I, wherein X, $R_2$, $G_1$, $G_2$, $R_1$, $R_3$, $R_4$, $R_5$, $R_6$, and $R_7$ are as under formula I above, can be prepared by performing an amidation reaction on compounds of formula X, wherein X, $R_2$, $G_1$, $G_2$, $R_1$, $R_3$, $R_4$, $R_5$, $R_6$, and $R_7$ are as under formula I above, following scheme 4.

Scheme 4
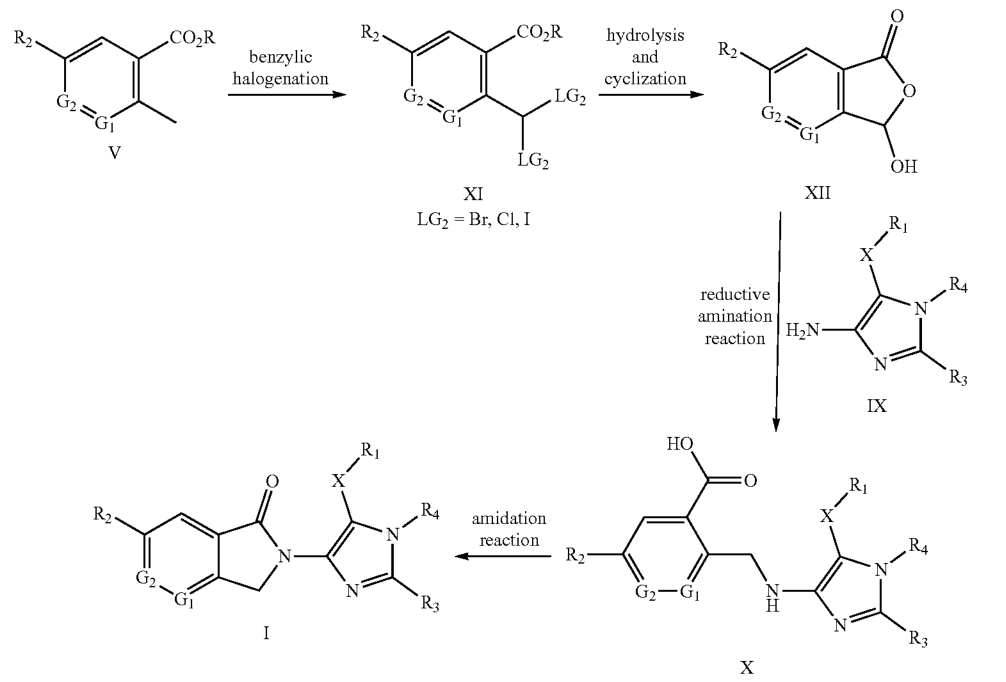
V
XI
$LG_2$ = Br, Cl, I
XII
IX
I
X
The reaction details for the transformation of compounds of formula X into compounds of formula I (amidation reaction) are illustrated in scheme 5, and follow methods and conditions already described in schemes 2 and 3 above.
Scheme 5
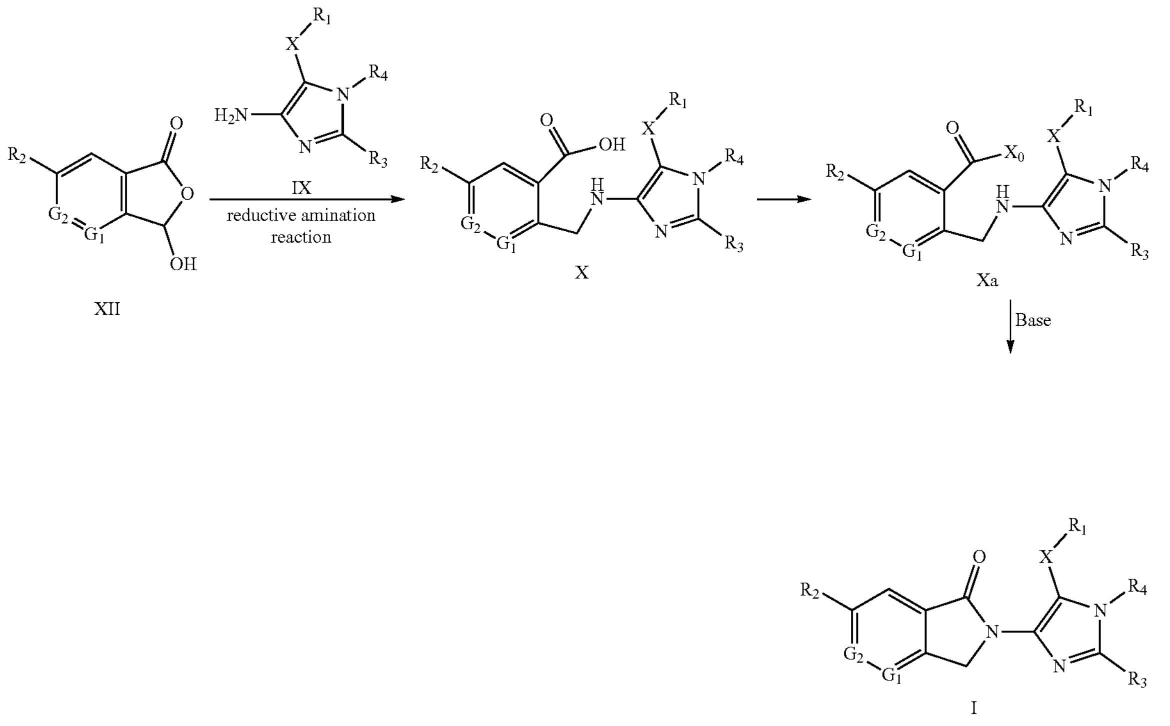
XII
X
Xa
I -continued $X_0$ = Halogen,

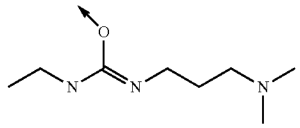

$X_{01}$

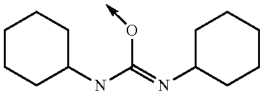

$X_{02}$

Compounds of formula X can be prepared by reacting compounds of formula XII, wherein $G_1$, $G_2$ and $R_2$ are as defined in formula I above, with compounds of formula IX, wherein $R_1$, X, $R_3$, $R_4$, $R_5$, $R_6$ and $R_7$ are as defined in formula I above, under reductive amination conditions (scheme 5). The reaction can be carried out in the presence of reducing agent, for example sodium cyanoborohydride or sodium triacetoxyborohydride, amongst others and optionally in the presence of an acid, such as trifluoroacetic acid, formic acid or acetic acid amongst others, and at temperatures ranging from 0° C. to the boiling point of the reaction mixture. The reaction can be carried out in the presence of inert solvents such as ethanol, methanol, dioxane or tetrahydrofuran. Such reactions involving two step conversion from compounds of formula XII to compounds of formula I have been described in literature for example in Bioorganic & Medicinal Chemistry Letters 26 (2016) 5947-5950.

Compounds of formula XII, wherein $G_1$, $G_2$, and $R_2$ are as defined in formula I above, can be prepared from compounds of formula XI, wherein $G_1$, $G_2$, and $R_2$ are as defined in formula I above, and $LG_2$ is chloro, bromo or iodo (preferably bromo), and R is $C_1$-$C_6$ alkyl, benzyl or a phenyl group, by a hydrolysis and subsequent cyclization reaction. The reaction can be carried out either under basic conditions, using metal hydroxide, for example using aqueous sodium hydroxide, in the presence of a solvent such as dioxane, tetrahydrofuran or water, and at temperature ranging from 20 to 150° C., as reported in Synlett 1992, (6), 531-533, or under aqueous acidic conditions, for example using acetic acid, hydrochloric acid or sulfuric acid, in the presence of solvent such as water, dioxane, or halogenated solvents, such as dichloroethane, as reported in Tetrahedron 62 (2006) 9589-9602.

Compounds of formula XI, wherein $G_1$, $G_2$, and $R_2$ are as defined in formula I above, and $LG_2$ is chloro, bromo or iodo (preferably bromo), and R is $C_1$-$C_6$ alkyl, benzyl or a phenyl group, can be prepared from compounds of formula V, wherein $G_1$, $G_2$, and $R_2$ are as defined in formula I above, and R is $C_1$-$C_6$ alkyl, benzyl or a phenyl group, by methods and conditions similar to those described in scheme 2, for the conversion of compound of formula V to compound of formula VI.

Alternatively compounds of formula I, wherein X, $R_2$, $G_1$, $G_2$, $R_1$, $R_3$, $R_4$, $R_5$, $R_6$, and $R_7$ are as under formula I above may be prepared Scheme 6

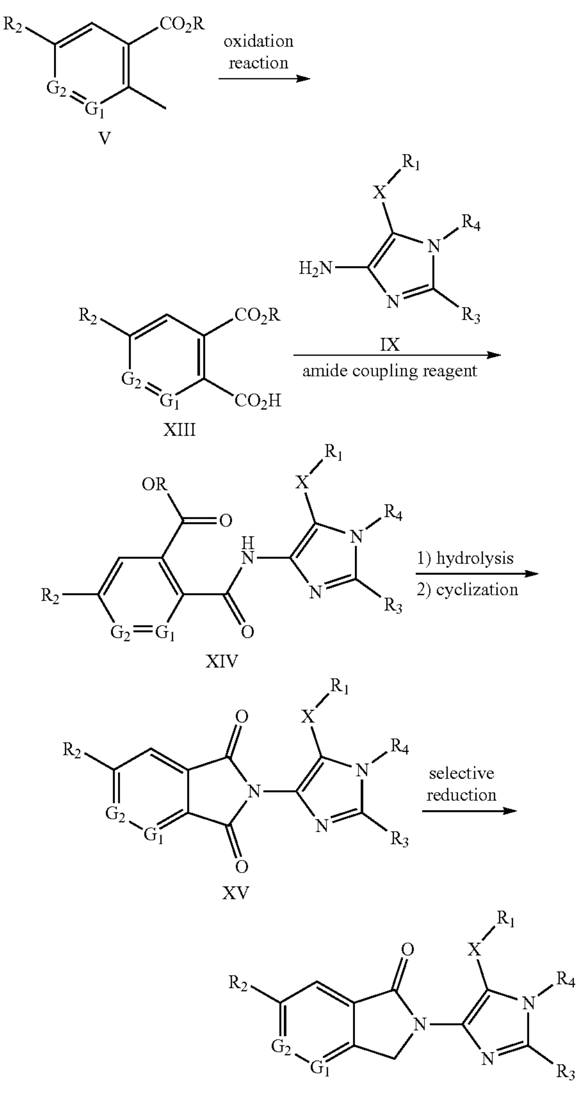

from compounds of formula XV, wherein X, $R_2$, $G_1$, $G_2$, $R_1$, $R_3$, $R_4$, $R_5$, $R_6$, and $R_7$ are defined as under formula I above, via selective reduction of the carbonyl functional group (scheme 6). The reaction can be carried out in the presence of reducing agent, for example $NaBH_4$, $LiAlH_4$, palladium on carbon in the presence of hydrogen, or a combination of two reducing agent for example $NaBH_4$ followed by triethylsilane. Such reactions have been described for example in US20100160303A1.

Compounds of formula XV, wherein X, $R_2$, $G_1$, $G_2$, $R_1$, $R_3$, $R_4$, $R_5$, $R_6$, and $R_7$ are as under formula I above, may be prepared from compounds of formula XIV, wherein X, $R_2$, $G_1$, $G_2$, $R_1$, $R_3$, $R_4$, $R_5$, RB, and $R_7$ are as under formula I Alternatively, compounds of formula I, wherein X, $R_2$, $G_1$, $G_2$, $R_1$, $R_3$, $R_4$, $R_5$, $R_6$, and $R_7$ are as defined in formula I above, may be prepared by a cyclization reaction of compounds of formula XVII, wherein wherein X, $R_2$, $G_1$, $G_2$, $R_1$, $R_3$, $R_4$, $R_5$, $R_6$, and $R_7$ are as defined in formula I above, and R is $C_1$-$C_6$ alkyl, benzyl or phenyl (scheme 7).

Scheme 7

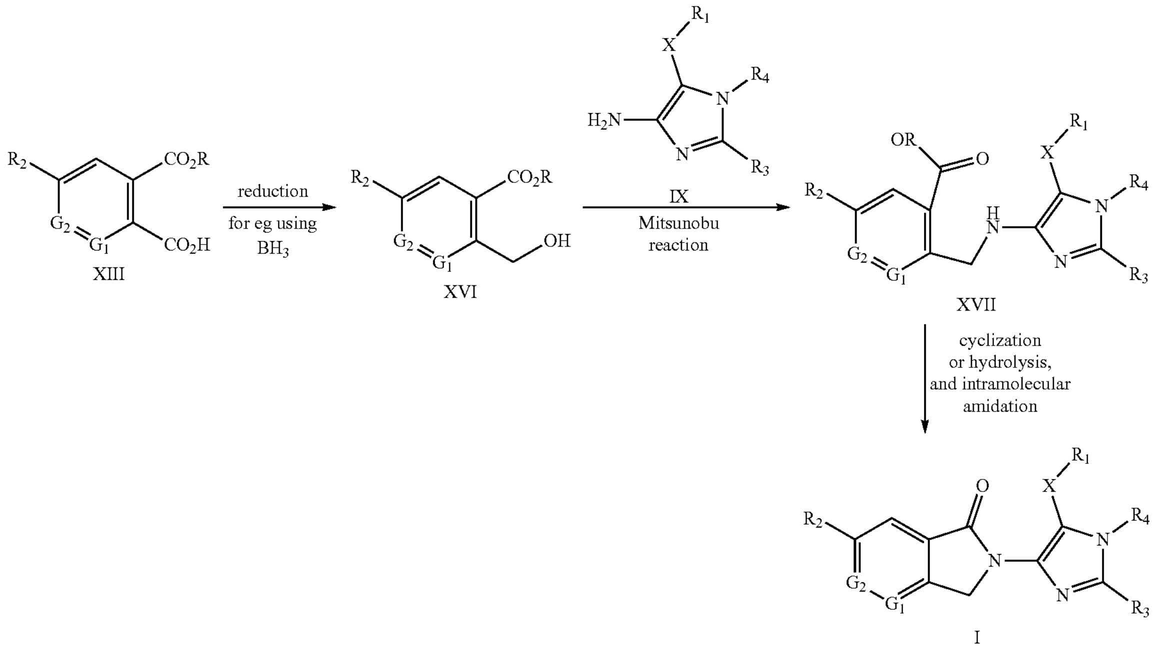

above, and R is $C_1$-$C_6$ alkyl, benzyl or phenyl, by a hydrolysis reaction and subsequent cyclization reaction, as described in scheme 2 for the conversion of compounds of formula X to compounds of formula I.

Compounds of formula XIV, wherein X, $R_2$, $G_1$, $G_2$, $R_1$, $R_3$, $R_4$, $R_5$, $R_6$, and $R_7$ are as under formula I above, and R is $C_1$-$C_6$ alkyl, benzyl or phenyl, may be prepared by reacting compounds of formula XIII, wherein $R_2$, $G_1$, and $G_2$ are as described in formula I above, and R is $C_1$-$C_6$ alkyl, benzyl or phenyl, with compounds of formula IX, wherein $R_1$, X, $R_3$, $R_4$, $R_5$, $R_6$ and $R_7$ are as defined in formula I above, under amidation reaction conditions already described in scheme 3.

Compounds of formula XIII, wherein $R_2$, $G_1$, and $G_2$ are as described in formula I above, and R is $C_1$-$C_6$ alkyl, benzyl or phenyl, may be prepared by benzylic oxidation of compounds of formula V, wherein $R_2$, $G_1$, and $G_2$ are as described in formula I above, and R is $C_1$-$C_6$ alkyl, benzyl or phenyl. The reaction can be carried out in the presence of oxidative reagents, such as $KMNO_4$, $nBu_4MnO_4$, $K_2S_2O_8$, in the presence of oxygen, or under photochemical conditions in the presence of oxygen, and at temperature ranging from 20° C. to the boiling point of the reaction mixture. The reaction is carried out in the presence of an inert solvent such as acetonitrile, ethyl acetate, DMSO, or dichloroethane. Such reactions are known in the literature, for example in *Synthesis*, 2017, 49, 4007-4016, *Synthesis*, 2006, 1757-1759 and IOSR Journal of Applied Chemistry, 2014, 7, 16-27.

Such reactions may be carried out in the presence of a base, such as potassium tert-butoxide, lithium diisopropylamide, or sodium hydride amongst others, and at temperature ranging from −20° C. to the boiling point of the reaction mixture, and in the presence of an inert solvent, such as tetrahydrofuran, dioxane or DMF. Such reactions are reported, for example, in Synlett 2006(4): 591-594.

Compounds of formula XVII, wherein X, $R_2$, $G_1$, $G_2$, $R_1$, $R_3$, $R_4$, $R_5$, $R_6$, and $R_7$ are as defined in formula I above, and R is $C_1$-$C_6$ alkyl, benzyl or phenyl, may be prepared by reacting compounds of formula XVI, wherein $R_2$, $G_1$ and $G_2$ are as defined in formula I above, and R is $C_1$-$C_6$ alkyl, benzyl or phenyl, with compounds of formula IX, wherein $R_1$, X, $R_3$, $R_4$, $R_5$, $R_6$ and $R_7$ are as defined in formula I above, under Mitsunobu conditions. Such reactions are well known to those skilled in the state of art, and can be carried out in the presence of phosphine reagent, such as triphenylphosphine, tributylphosphine, or polymer supported triphenyl phosphine amongst others, and in the presence of an azodicarboxylate reagent, such as diethyl azodicarboxylate or diisopropyl azodicarboxylate, and at temperature ranging from 0° C. and 100° C., and in the presence of an inert solvent such as acetonitrile, dichloromethane, tetrahydrofuran, or toluene. Such reactions are reported for example in Synthesis, 1981(1), 1-28.

Compounds of formula XVI, wherein $R_2$, $G_1$ and $G_2$ are as defined in formula I above, and R is $C_1$-$C_6$ alkyl, benzyl or phenyl, may be prepared by reacting compounds of formula XIII, wherein $R_2$, $G_1$ and $G_2$ are as defined in formula I above, and R is $C_1$-$C_6$ alkyl, benzyl or phenyl, with reducing agents, such as, for example, metal hydrides like as lithium aluminumhydride, DIBAL-H, or boranes (such as diborane, or borane tetrahydrofuran complex amongst others), at temperatures ranging from 0° C. and 150° C., and in the presence of an inert solvent such as tetrahydrofuran, or dioxane. Such reactions have been reported, for example, in Tetrahedron Letters, 1982, 23, 2475-2478.

The compounds of formula XVII-a (XVII-a)

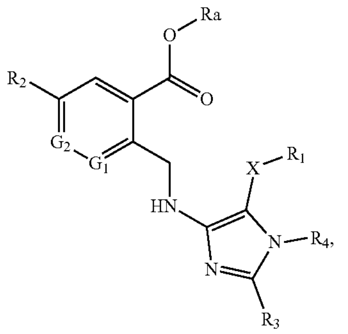

wherein

X, $R_2$, $G_1$, $G_2$, $R_1$, $R_3$, $R_4$, $R_5$, $R_6$, and $R_7$ are as defined under formula I above, and Ra is hydrogen, $C_1$-$C_6$ alkyl, benzyl or phenyl are novel, especially developed for the preparation of the compounds of formula I according to the invention and therefore represent a further object of the invention. The preferences and preferred embodiments of the substituents of the compounds of formula I are also valid for the compounds of formula XVII-a. Preferably, Ra is hydrogen or $C_1$-$C_6$ alkyl; even more preferably, Ra is hydrogen, methyl or ethyl; most preferably Ra is hydrogen.

Compounds of formula IX, wherein $R_1$, X, $R_3$, $R_4$, $R_5$, $R_6$ and $R_7$ are as defined in formula I above, can be prepared by performing a deprotection reaction (BOC group removal) on compounds of formula XIX, wherein $R_1$, X, $R_3$, $R_4$, $R_5$, $R_6$ and $R_7$ are as defined in formula I above (scheme 8).

The reaction can be carried out in the presence of acids such as trifluoroacetic acid, hydrochloric acid or sulfuric acid amongst others, under conditions already described above.

Compounds of formula XIX, wherein $R_1$, X, $R_3$, $R_4$, $R_5$, $R_6$ and $R_7$ are as defined in formula I above, can be prepared by the reaction of compounds of formula XVIII, wherein $R_1$, X, $R_3$, $R_4$, $R_5$, $R_6$ and $R_7$ are as defined in formula I above, with an organo-azide, in the presence of a suitable base and tert-butanol t-BuOH, and in the presence of a coupling agent, optionally in the presence of a Lewis acid, and in the presence of an inert solvent, at temperatures between 50° C. and the boiling point of the reaction mixture. The reaction can be carried out in the presence of a coupling agent such as $T_3P$, or via activation of the carboxylic acid with $SOCl_2$ or oxalyl chloride, or other coupling agents as described in scheme 3 for the conversion of compounds of formula X into compounds of formula Xa. Examples of organo-azide include $TMSN_3$, sodium azide, or tosyl azide, and a suitable solvent may be toluene, xylene, THE or acetonitrile. Example of a suitable Lewis acid may include $Zn(OTf)_2$, $Sc(OTf)_2$, or $Cu(OTf)_2$ amongst others.

Compounds of formula XIX can also be prepared by reacting compounds of formula XVIII with diphenylphosphorylazide, in the presence of an organic base such as triethylamine, or diisopropylethylamine amongst others, in the presence of tert-butanol t-BuOH and an inert solvent, for example a halogenated solvent such as dichloromethane or dichloroethane, or cyclic ethers such as tetrahydrofuran amongst others, at temperatures ranging from 50° C. to the boiling point of the reaction mixture. Such reactions of converting carboxylic acids to BOC protected amines are well known to those skilled in the state of art by the name of Curtius reaction and are reported, for example, in *Org. Lett.*, 2005, 7, 4107-4110; Journal of Medicinal Chemistry, 49(12), 3614-3627; 2006, *J. Am. Chem. Soc.*, 1972, 94 (17), pp 6203-6205.

Compounds of formula IX, wherein $R_1$, X, $R_3$, $R_4$, $R_5$, $R_6$ and $R_7$ are as defined in formula I above, may also be prepared from compounds of formula XX, wherein $R_1$, X, $R_3$, $R_4$, $R_5$, $R_6$ and $R_7$ are as defined in formula I above, by a Hofmann-rearrangement reaction. The reaction can be Scheme 8

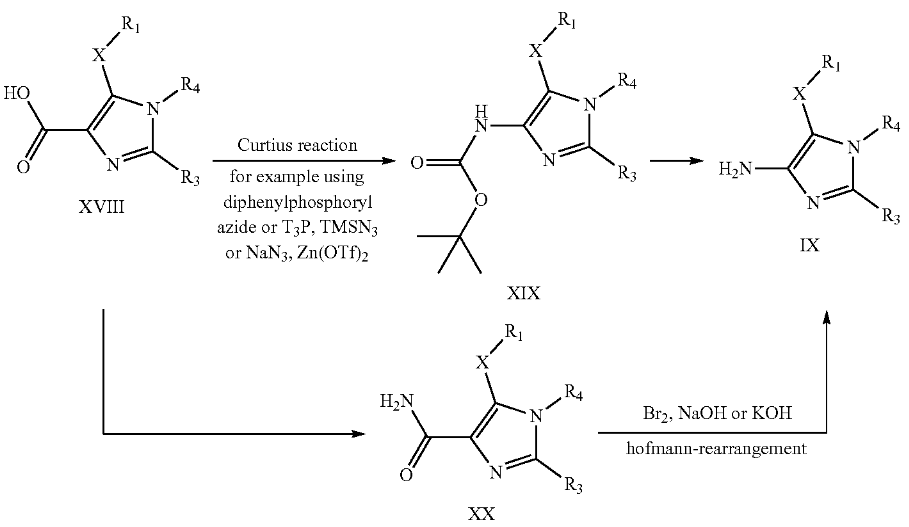

carried out in the presence of a base, for example metal hydroxides, such as aqueous sodium hydroxide or potassium hydroxide, or organic bases such as DBU (1,8-diazabicyclo (5.4.0)undec-7-ene), and in the presence of electrophilic halogenating reagents, such as chlorine, bromine or N-bromo-succinimide, and at temperatures ranging from 20° C. to the boiling point of the reaction mixture. Such reactions are known by the name of Hofmann-rearrangement and are reported in literature for example, for example in Chem. Ber. 1881, 14, 2725.

Compounds of formula XX, wherein $R_1$, X, $R_3$, $R_4$, $R_5$, $R_6$ and $R_7$ are as defined in formula I above, can be prepared by the reaction of compounds of formula XVIII, wherein $R_1$, X, $R_3$, $R_4$, $R_5$, $R_6$ and $R_7$ are as defined in formula I above, with ammonia, for example $NH_4OH$, $NH_3$, or other ammonia surrogates, in the presence of carboxylic acid activating agent as described in scheme 3 above.

Compounds of Formula XIX (XIX)

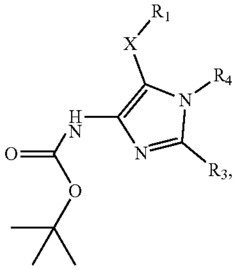

wherein $R_1$, X, $R_3$, $R_4$, $R_5$, $R_6$ and $R_7$ are as defined under formula I above, are novel, especially developed for the preparation of the compounds of formula I according to the invention and therefore represent a further object of the invention. The preferences and preferred embodiments of the substituents of the compounds of formula I are also valid for the compounds of formula XIX. Most preferably X is $SO_2$, $R_1$ is ethyl and $R_3$/$R_4$ are as described in table I. In one embodiment, the compounds for formula (XIX) are as described above with the proviso that the compounds tert-butyl N-(2-cyclopropyl-5-ethylsulfanyl-1-methyl-imidazol-4-yl)carbamate and tert-butyl N-[5-ethylsulfanyl-1-methyl-2-[4-(trifluoromethyl)phenyl]imidazol-4-yl]carbamate are excluded.

Few compounds of formula XVIII, wherein X is S (sulfide), (XVIII)

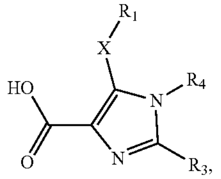

are known in the literature (CAS 2234901-66-5, CAS 2236074-76-1), and are described in WO2018130443 and WO2018130437.

Alternatively compounds of formula I, wherein $R_2$, $G_1$, $G_2$, $R_1$, X, $R_3$, $R_4$, $R_5$, $R_6$, and $R_7$ are as defined in formula I above, can also be prepared following scheme 9.

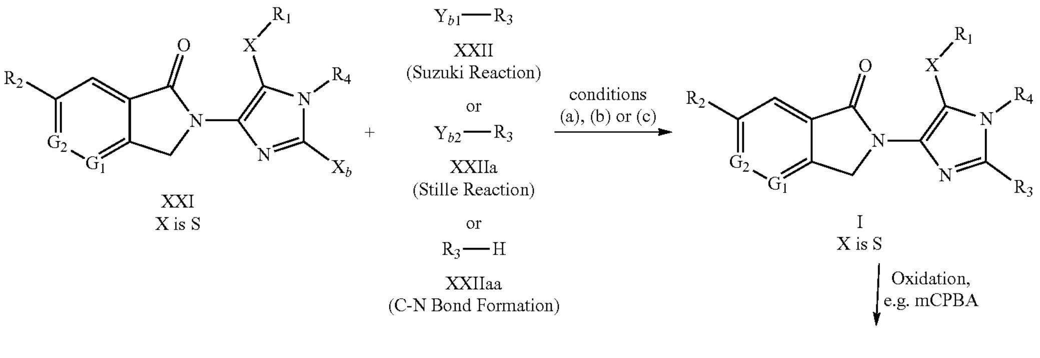

-continued

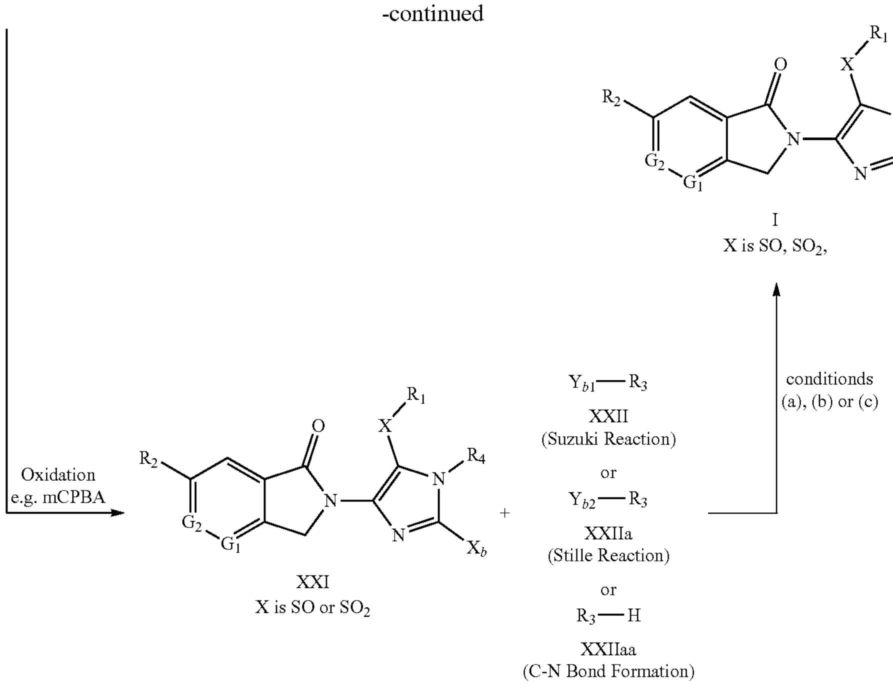

(a) Suzuki reaction: PD cat. (e.g. $Pd(PPh_3)_4$ or $Pd(dppf)Cl_2$), base (e.g. $Na_2CO_3$), solvent (e.g. 1,2-dimethoxyethane/water), 25-180° C.

(b) Stille reaction: Pd cat. (e.g. $Pd(PPh_3)_4$ or $Pd(PPh_3)Cl_2$), solvent (e.g. toluene), 25-180° c.

(c) C-N bond formation: Optional base (e.g. $K_2CO_3$ or $Cs_2CO_3$), optional presence of copper or palladium catalyst, optional additive (such as N,N′-dimethylethylenediamine), optional ligand (such as Xantphos), solvent (e.g. dioxane, pyradine or N,N-dimethylformamide DMF), 25-180° C.

In the particular situation within scheme 9 when $R_3$ is an optionally substituted pyrazole group which is mono- or polysubstituted by substitutent selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl and $C_1$-$C_4$ alkylsulfonyl; $C_3$-$C_6$ cycloalkyl, $C_3$-$C_6$ cycloalkyl monosubstituted by cyano, $C_1$-$C_6$ cyanoalkyl, and is linked via a ring nitrogen atom to the imidazole ring which is connected to the substitutent $R_4$, then compounds of formula I, wherein X is SO or $SO_2$, may be prepared from compounds of formula XXI, wherein $R_2$, $G_1$, $G_2$, $R_1$, and $R_4$, are as defined in formula I above and in which X is SO or $SO_2$, and wherein Xb is a leaving group like, for example, chlorine, bromine or iodine (preferably chlorine or bromine), or an aryl- or (halo)alkylsulfonate such as trifluoromethanesulfonate, by reaction (C—N bond formation) with an optionally substituted pyrazole $R_3$—H (which contains an appropriate NH functionality) (XXIIaa), wherein $R_3$ is an optionally substituted pyrazole group which is mono- or polysubstituted by substitutent selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl and $C_1$-$C_4$ alkylsulfonyl; $C_3$-$C_6$ cycloalkyl, $C_3$-$C_6$ cycloalkyl monosubstituted by cyano, $C_1$-$C_6$ cyanoalkyl, in solvents such as alcohols (eg. methanol, ethanol, isopropanol, or higher boiling linear or branched alcohols), pyridine or acetic acid, optionally in the presence of an additional base, such as potassium carbonate $K_2CO_3$ or cesium carbonate $Cs_2CO_3$, optionally in the presence of a copper catalyst, for example copper(I) iodide, at temperatures between 30-180° C., optionally under microwave irradiation.

In the particular situation within scheme 9 when $R_3$ is —$N(R_5)COR_7$, wherein $R_5$ and $R_7$ are as defined in formula I, then compounds of formula I, wherein X is SO or $SO_2$, may be prepared from compounds of formula XXI, wherein $R_2$, $G_1$, $G_2$, $R_1$, and $R_4$, are as defined in formula I, and in which X is SO or $SO_2$, and wherein Xb is a leaving group like, for example, chlorine, bromine or iodine (preferably chlorine or bromine), or an aryl- or (halo)alkylsulfonate such as trifluoromethanesulfonate, by reaction (C—N bond formation) with a reagent $R_3$—H (XXIIaa) equivalent to $HN(R_5)COR_7$, wherein $R_5$ and $R_7$ are as defined in formula I. Such a reaction is performed in the presence of a base, such as potassium carbonate, cesium carbonate, sodium hydroxide, in an inert solvent, such as toluene, dimethylformamide DMF, N-methyl pyrrolidine NMP, dimethyl sulfoxide DMSO, dioxane, tetrahydrofuran THF, and the like, optionally in the presence of a catalyst, for example palladium(II)acetate, bis(dibenzylideneacetone)palladium(0) (Pd $(dba)_2$) or tris(dibenzylideneacetone)-dipalladium(0) ($Pd_2$ $(dba)_3$, optionally in form of a chloroform adduct), or a palladium pre-catalyst such as for example tert-BuBrettPhos Pd $G_3$ [(2-Di-tert-butylphosphino-3,6-dimethoxy-2',4',6'-triisopropyl-1,1'-biphenyl)-2-(2'-amino-1,1'-biphenyl)]palladium(II) methanesulfonate or BrettPhos Pd $G_3$ [(2-di-cyclohexylphosphino-3,6-dimethoxy-2',4',6'-triisopropyl-1,1'-biphenyl)-2-(2'-amino-1,1'-biphenyl)]palladium(II) methanesulfonate, and optionally in the presence of a ligand, for example SPhos, t-BuBrettPhos or Xantphos, at temperatures between 60-120° C., optionally under microwave irradiation.

Reagents $HN(R_5)COR_7$, wherein $R_5$ and $R_7$ are as defined in formula I, or substituted pyrazole group which is mono- or polysubstituted by substitutent selected from the group consisting of halogen, cyano, $C_1$-$C_4$ alkyl, $C_1$-$C_4$ haloalkyl, $C_1$-$C_4$ alkoxy, $C_1$-$C_4$ haloalkoxy, $C_1$-$C_4$ alkylsulfanyl, $C_1$-$C_4$ alkylsulfinyl and $C_1$-$C_4$ alkylsulfonyl; $C_3$-$C_6$ cycloalkyl, $C_3$-$C_6$ cycloalkyl monosubstituted by cyano, $C_1$-$C_6$ cyano-alkyl, are either known, commercially available or may be prepared by methods known to a person skilled in the art.

Alternatively, compounds of formula I, wherein X is SO or $SO_2$, may be prepared by a Suzuki reaction, which involves for example, reacting compounds of formula XXI, wherein $R_1$, $R_2$, $G_1$, $G_2$ and $R_4$ are as defined in formula I, and in which X is SO or $SO_2$, and wherein Xb is a leaving group like, for example, chlorine, bromine or iodine (preferably chlorine or bromine), or an aryl- or (halo)alkylsulfonate such as trifluoromethanesulfonate, with compounds of formula (XXII), wherein $R_3$ is as defined above and wherein $Y_{b1}$ can be a boron-derived functional group, such as for example $B(OH)_2$ or $B(OR_{b1})_2$ wherein $R_{b1}$ can be a $C_1$-$C_4$ alkyl group or the two groups $OR_{b1}$ can form together with the boron atom a five membered ring, as for example a pinacol boronic ester. The reaction may be catalyzed by a palladium based catalyst, for example tetrakis (triphenyl-phosphine)palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium (II) (XPhos palladacycle), in presence of a base, like sodium carbonate, tripotassium phosphate or cesium fluoride, in a solvent or a solvent mixture, like, for example dioxane, acetonitrile, N,N-dimethylformamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in J. Organomet. Chem. 576, 1999, 147-168.

Alternatively compounds of formula I, wherein X is SO or $SO_2$, may be prepared by a Stille reaction between compounds of formula (XXIIa), wherein $R_3$ is as defined above, and wherein $Y_{b2}$ is a trialkyltin derivative, preferably tri-n-butyl tin or tri-methyl-tin, and compounds of formula XXI, wherein $R_1$, $R_2$, $G_1$, $G_2$ and $R_4$ are as defined in formula I, and in which X is SO or $SO_2$, and wherein Xb is a leaving group like, for example, chlorine, bromine or iodine (preferably chlorine or bromine), or an aryl- or (halo)alkylsulfonate such as trifluoromethanesulfonate. Such Stille reactions are usually carried out in the presence of a palladium catalyst, for example tetrakis(triphenylphosphine)palladium(0), or bis(triphenylphosphine)palladium (II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example J. Org. Chem., 2005, 70, 8601-8604, J. Org. Chem., 2009, 74, 5599-5602, and Angew. Chem. Int. Ed., 2004, 43, 1132-1136.

When $R_3$ is a five-membered aromatic ring system linked via a ring nitrogen atom to the imidazole ring which is connected to the substitutent $R_4$, then compounds of formula I, wherein X is SO or $SO_2$, may be prepared from compounds of formula XXI, wherein $R_1$, $R_2$, $G_1$, $G_2$ and $R_4$ are as defined in formula I, and in which X is SO or $SO_2$, and wherein Xb is a leaving group like, for example, chlorine, bromine or iodine (preferably chlorine or bromine), or an aryl- or (halo)alkylsulfonate such as trifluoromethanesulfonate, by reaction with a heterocycle $R_3$—H (which contains an appropriate NH functionality) (XXIIaa), wherein $R_3$ is as defined above, in the presence of a base, such as potassium carbonate $K_2CO_3$ or cesium carbonate $Cs_2CO_3$, optionally in the presence of a copper catalyst, for example copper(I) iodide, with or without an additive such as L-proline, N,N'-dimethylcyclohexane-1,2-diamine or N,N'-dimethyl-ethylene-diamine, in an inert solvent such as N-methylpyrrolidone NMP or N,N-dimethylformamide DMF at temperatures between 30-150° C., optionally under microwave irradiation.

Oxidation of compounds of formula XXI, wherein $R_1$, $R_2$, $G_1$, $G_2$ and $R_4$ are as defined in formula I, and in which X is S, and wherein Xb is a leaving group like, for example, chlorine, bromine or iodine (preferably chlorine or bromine), or an aryl- or (halo)alkylsulfonate such as trifluoromethanesulfonate, with a suitable oxidizing agent, into compounds of formula XXI, wherein X is SO or $SO_2$ may be achieved under conditions already described above.

A large number of compounds of the formula (XXII), (XXIIa) and (XXIIaa) are commercially available or can be prepared by those skilled in the art.

Alternatively, compounds of formula I, wherein X is SO or $SO_2$, may be prepared from compounds of formula XXI, wherein X is S (sulfide) by involving the same chemistry as described above, but by changing the order of the steps (i.e. by running the sequence XXI (X is S) to I (X is S) via Suzuki, Stille or C—N bond formation, followed by an oxidation step to form I (X is SO or $SO_2$) (scheme 9).

Alternatively, compounds of formula XVIII, in which X is $SO_2$, and wherein $R_1$, $R_3$, $R_4$, $R_5$, $R_8$ and $R_7$ are as defined in formula I above, Scheme 10

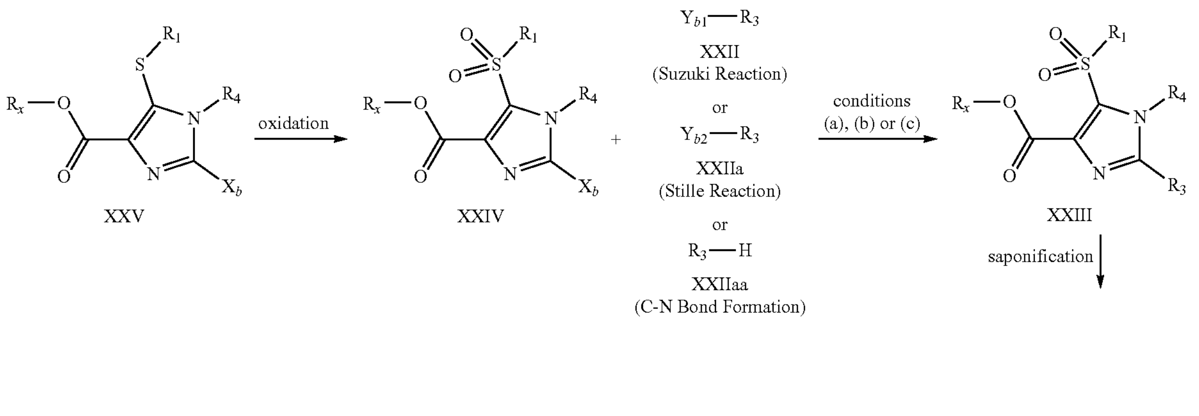

XXV XXIV XXIII

-continued

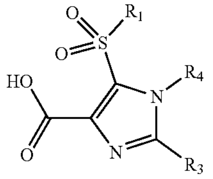

XVIII
X = $SO_2$ (a) Suzuki reaction: PD cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° c.
(c) C-N bond formation: Optional base (e.g. $K_2CO_3$ or $Cs_2CO_3$), optional presence of copper or palladium catalyst, optional additive (such as N,N′-dimethylethylenediamine), optional ligand (such as Xantphos), solvent (e.g. dioxane, pyradine or N,N-dimethylformamide DMF), 25-180° C.

can be prepared (scheme 10) by a saponification reaction of compounds of formula XXIII, wherein $R_1$, $R_3$, $R_4$, $R_5$, $R_6$ and $R_7$ are as defined in formula I above, and Rx is $C_1$-$C_6$ alkyl, benzyl or phenyl, in the presence of a suitable base, for example sodium hydroxide NaOH, lithium hydroxide LiOH or barium hydroxide $Ba(OH)_2$, in the presence of a solvent such as ethanol, methanol, dioxane, tetrahydrofuran or water (or mixtures thereof), under conditions already described above (see discussions on converting (VI) to (X) in scheme 2, and (XVII) into (X) in scheme 2a; alternatively, Krapcho-type conditions as described above may also be used).

Compounds of formula XXIII, wherein $R_1$, $R_3$, $R_4$, $R_5$, $R_6$ and $R_7$ are as defined in formula I above, and Rx is $C_1$-$C_6$ alkyl, benzyl or phenyl, can be prepared from compounds of formula XXIV, wherein $R_1$ and $R_4$ are as defined in formula I above, and Rx is $C_1$-$C_6$ alkyl, benzyl or phenyl, and Xb is a leaving group like, for example, chlorine, bromine or iodine (preferably chlorine or bromine), or an aryl- or (halo)alkylsulfonate such as trifluoromethanesulfonate, via Suzuki, Stille or C—N bond formation, involving reagents of the formula XXII, XXIIa or XXIIaa, wherein $R_3$, $R_5$, $R_6$ and $R_7$ are as defined in formula I above, and $Y_{b1}$ and $Y_{b2}$ are as defined above in scheme 9, under conditions already described above (see discussions on converting (XXI) to (I) in scheme 9).

Compounds of formula XXIV, wherein $R_1$ and $R_4$ are as defined in formula I above, and Rx is $C_1$-$C_6$ alkyl, benzyl or phenyl, and Xb is a leaving group like, for example, chlorine, bromine or iodine (preferably chlorine or bromine), or an aryl- or (halo)alkylsulfonate such as trifluoromethanesulfonate, can be prepared by oxidation of compounds of formula XXV, wherein $R_1$ and $R_4$ are as defined in formula I above, and Rx is $C_1$-$C_6$ alkyl, benzyl or phenyl, and Xb is a leaving group like, for example, chlorine, bromine or iodine (preferably chlorine or bromine), or an aryl- or (halo)alkylsulfonate such as trifluoromethanesulfonate, involving a suitable oxidizing agent, and under conditions already described above.

Compounds of formula XXV, wherein $R_1$ and $R_4$ are as defined in formula I above, and Rx is $C_1$-$C_6$ alkyl, benzyl or phenyl, and Xb is a leaving group like, for example, chlorine, bromine or iodine (preferably chlorine or bromine), or an aryl- or (halo)alkylsulfonate such as trifluoromethanesulfonate, are either known or may be prepared according to procedures found in the literature. For example, the compound of formula XXV, wherein $R_1$ is ethyl, $R_4$ is methyl, Xb is bromo and Rx is ethyl (CAS 2407490-49-5), is described in WO2018130443, WO2018130437 and WO2020002082.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reactions are advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention, and by post modification of compounds of with reactions such as oxidation, alkylation, reduction, acylation and other methods known by those skilled in the art.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.,* 32 (12), 2561-73, 1989 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the following Tables A-1 to A-48, C-1 to C-24, D-1 to D-12, and E-1 to E-12 can be prepared according to the methods described above. The examples which follow are intended to illustrate the invention and show preferred compounds of formula I, in the form of a compound of formula I-1 to I-4.

The tables below illustrate specific compounds of the invention. In the tables, $CH_2cPr$ means $CH_2$-cyclopropyl.

Table A-1 provides 19 compounds A-1.001 to A-1.019 of formula I-1 wherein $G_1$ is N, $G_2$ is N, X is S, $R_1$ is $CH_2CH_3$, $R_4$ is methyl and $R_3$ are as defined in table B.

(I-1)

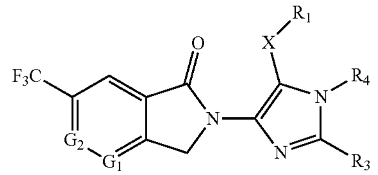

For example, A-1.010 is

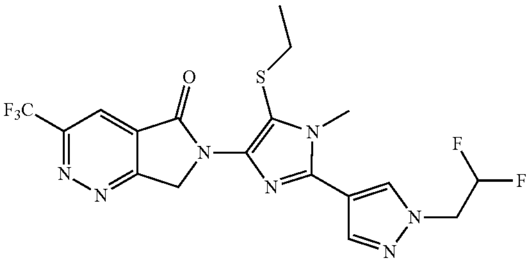 [SMILES: CCSc1c(N2Cc3nnc(C(F)(F)F)cc3C2=O)nc(-c2cnn(CC(F)F)c2)n1C]

TABLE B
| Substituent definitions of $R_3$ | |
|---|---|
| Index | $R_3$ |
| 1 | 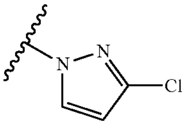 [SMILES: *n1ccc(Cl)n1] |
| 2 | 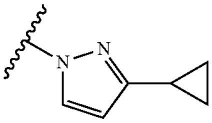 [SMILES: *n1ccc(C2CC2)n1] |
| 3 | 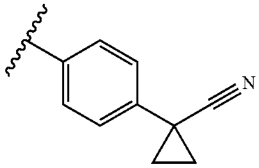 [SMILES: *c1ccc(C2(C#N)CC2)cc1] |
| 4 | 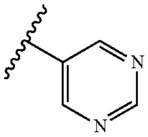 [SMILES: *c1cncnc1] |
| 5 | 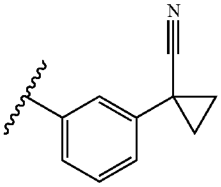 [SMILES: *c1cccc(C2(C#N)CC2)c1] |
| 6 | 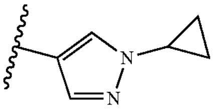 [SMILES: *c1cnn(C2CC2)c1] |
| 7 | 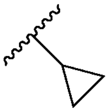 [SMILES: *C1CC1] |
| 8 | 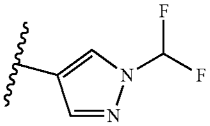 [SMILES: *c1cnn(C(F)F)c1] |
| 9 | 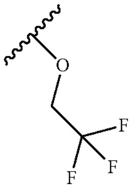 [SMILES: *OCC(F)(F)F] |
| 10 | 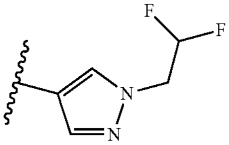 [SMILES: *c1cnn(CC(F)F)c1] |
| 11 | 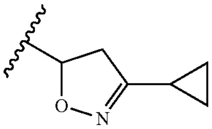 [SMILES: *C1CC(C2CC2)=NO1] |
| 12 | 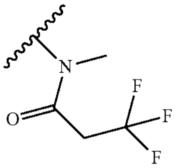 [SMILES: *N(C)C(=O)CC(F)(F)F] |
| 13 | 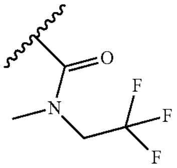 [SMILES: *C(=O)N(C)CC(F)(F)F] |
| 14 | 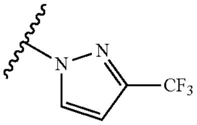 [SMILES: *n1ccc(C(F)(F)F)n1] |
| 15 | 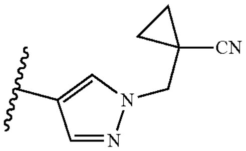 [SMILES: *c1cnn(CC2(C#N)CC2)c1] |
| 16 | 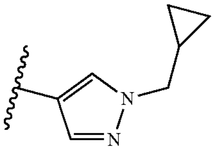 [SMILES: *c1cnn(CC2CC2)c1] |
| 17 | 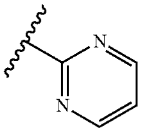 [SMILES: *c1ncccn1] |
| 18 | 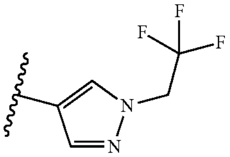 [SMILES: *c1cnn(CC(F)(F)F)c1] |
| 19 | 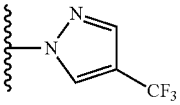 |
Table A-2 provides 19 compounds A-2.001 to A-2.019 of formula I-1 wherein $G_1$ is N, $G_2$ is N, X is S, $R_1$ is $CH_2CH_3$, $R_4$ is ethyl and $R_3$ are as defined in table B.

Table A-3 provides 19 compounds A-3.001 to A-3.019 of formula I-1 wherein $G_1$ is N, $G_2$ is N, X is S, $R_1$ is $CH_2cPr$, $R_4$ is methyl and $R_3$ are as defined in table B.

Table A-4 provides 19 compounds A-4.001 to A-4.019 of formula I-1 wherein $G_1$ is N, $G_2$ is N, X is S, $R_1$ is $CH_2cPr$, $R_4$ is ethyl and $R_3$ are as defined in table B.

Table A-5 provides 19 compounds A-5.001 to A-5.019 of formula I-1 wherein $G_1$ is N, $G_2$ is N, X is SO, $R_1$ is $CH_2CH_3$, $R_4$ is methyl and $R_3$ are as defined in table B.

Table A-6 provides 19 compounds A-6.001 to A-6.019 of formula I-1 wherein $G_1$ is N, $G_2$ is N, X is SO, $R_1$ is $CH_2CH_3$, $R_4$ is ethyl and $R_3$ are as defined in table B.

Table A-7 provides 19 compounds A-7.001 to A-7.019 of formula I-1 wherein $G_1$ is N, $G_2$ is N, X is SO, $R_1$ is $CH_2cPr$, $R_4$ is methyl and $R_3$ are as defined in table B.

Table A-8 provides 19 compounds A-8.001 to A-8.019 of formula I-1 wherein $G_1$ is N, $G_2$ is N, X is SO, $R_1$ is $CH_2cPr$, $R_4$ is ethyl and $R_3$ are as defined in table B.

Table A-9 provides 19 compounds A-9.001 to A-9.019 of formula I-1 wherein $G_1$ is N, $G_2$ is N, X is $SO_2$, $R_1$ is $CH_2CH_3$, $R_4$ is methyl and $R_3$ are as defined in table B.

Table A-10 provides 19 compounds A-10.001 to A-10.019 of formula I-1 wherein $G_1$ is N, $G_2$ is N, X is $SO_2$, $R_1$ is $CH_2CH_3$, $R_4$ is ethyl and $R_3$ are as defined in table B.

Table A-11 provides 19 compounds A-11.001 to A-11.019 of formula I-1 wherein $G_1$ is N, $G_2$ is N, X is $SO_2$, $R_1$ is $CH_2cPr$, $R_4$ is methyl and $R_3$ are as defined in table B.

Table A-12 provides 19 compounds A-12.001 to A-12.019 of formula I-1 wherein $G_1$ is N, $G_2$ is N, X is $SO_2$, $R_1$ is $CH_2cPr$, $R_4$ is ethyl and $R_3$ are as defined in table B.

Table A-13 provides 19 compounds A-13.001 to A-13.019 of formula I-1 wherein $G_1$ is N, $G_2$ is CH, X is S, $R_1$ is $CH_2CH_3$, $R_4$ is methyl and $R_3$ are as defined in table B.

Table A-14 provides 19 compounds A-14.001 to A-14.019 of formula I-1 wherein $G_1$ is N, $G_2$ is CH, X is S, $R_1$ is $CH_2CH_3$, $R_4$ is ethyl and $R_3$ are as defined in table B.

Table A-15 provides 19 compounds A-15.001 to A-15.019 of formula I-1 wherein $G_1$ is N, $G_2$ is CH, X is S, $R_1$ is $CH_2cPr$, $R_4$ is methyl and $R_3$ are as defined in table B.

Table A-16 provides 19 compounds A-16.001 to A-16.019 of formula I-1 wherein $G_1$ is N, $G_2$ is CH, X is S, $R_1$ is $CH_2cPr$, $R_4$ is ethyl and $R_3$ are as defined in table B.

Table A-17 provides 19 compounds A-17.001 to A-17.019 of formula I-1 wherein $G_1$ is N, $G_2$ is CH, X is SO, $R_1$ is $CH_2CH_3$, $R_4$ is methyl and $R_3$ are as defined in table B.

Table A-18 provides 19 compounds A-18.001 to A-18.019 of formula I-1 wherein $G_1$ is N, $G_2$ is CH, X is SO, $R_1$ is $CH_2CH_3$, $R_4$ is ethyl and $R_3$ are as defined in table B.

Table A-19 provides 19 compounds A-19.001 to A-19.019 of formula I-1 wherein $G_1$ is N, $G_2$ is CH, X is SO, $R_1$ is $CH_2cPr$, $R_4$ is methyl and $R_3$ are as defined in table B.

Table A-20 provides 19 compounds A-20.001 to A-20.019 of formula I-1 wherein $G_1$ is N, $G_2$ is CH, X is SO, $R_1$ is $CH_2cPr$, $R_4$ is ethyl and $R_3$ are as defined in table B.

Table A-21 provides 19 compounds A-21.001 to A-21.019 of formula I-1 wherein $G_1$ is N, $G_2$ is CH, X is $SO_2$, $R_1$ is $CH_2CH_3$, $R_4$ is methyl and $R_3$ are as defined in table B.

Table A-22 provides 19 compounds A-22.001 to A-22.019 of formula I-1 wherein $G_1$ is N, $G_2$ is CH, X is $SO_2$, $R_1$ is $CH_2CH_3$, $R_4$ is ethyl and $R_3$ are as defined in table B.

Table A-23 provides 19 compounds A-23.001 to A-23.019 of formula I-1 wherein $G_1$ is N, $G_2$ is CH, X is $SO_2$, $R_1$ is $CH_2cPr$, $R_4$ is methyl and $R_3$ are as defined in table B.

Table A-24 provides 19 compounds A-24.001 to A-24.019 of formula I-1 wherein $G_1$ is N, $G_2$ is CH, X is $SO_2$, $R_1$ is $CH_2cPr$, $R_4$ is ethyl and $R_3$ are as defined in table B.

Table A-25 provides 19 compounds A-25.001 to A-25.019 of formula I-1 wherein $G_1$ is CH, $G_2$ is N, X is S, $R_1$ is $CH_2CH_3$, $R_4$ is methyl and $R_3$ are as defined in table B.

Table A-26 provides 19 compounds A-26.001 to A-26.019 of formula I-1 wherein $G_1$ is CH, $G_2$ is N, X is S, $R_1$ is $CH_2CH_3$, $R_4$ is ethyl and $R_3$ are as defined in table B.

Table A-27 provides 19 compounds A-27.001 to A-27.019 of formula I-1 wherein $G_1$ is CH, $G_2$ is N, X is S, $R_1$ is $CH_2cPr$, $R_4$ is methyl and $R_3$ are as defined in table B.

Table A-28 provides 19 compounds A-28.001 to A-28.019 of formula I-1 wherein $G_1$ is CH, $G_2$ is N, X is S, $R_1$ is $CH_2cPr$, $R_4$ is ethyl and $R_3$ are as defined in table B.

Table A-29 provides 19 compounds A-29.001 to A-29.019 of formula I-1 wherein $G_1$ is CH, $G_2$ is N, X is SO, $R_1$ is $CH_2CH_3$, $R_4$ is methyl and $R_3$ are as defined in table B.

Table A-30 provides 19 compounds A-30.001 to A-30.019 of formula I-1 wherein $G_1$ is CH, $G_2$ is N, X is SO, $R_1$ is $CH_2CH_3$, $R_4$ is ethyl and $R_3$ are as defined in table B.

Table A-31 provides 19 compounds A-31.001 to A-31.019 of formula I-1 wherein $G_1$ is CH, $G_2$ is N, X is SO, $R_1$ is $CH_2cPr$, $R_4$ is methyl and $R_3$ are as defined in table B.

Table A-32 provides 19 compounds A-32.001 to A-32.019 of formula I-1 wherein $G_1$ is CH, $G_2$ is N, X is SO, $R_1$ is $CH_2cPr$, $R_4$ is ethyl and $R_3$ are as defined in table B.

Table A-33 provides 19 compounds A-33.001 to A-33.019 of formula I-1 wherein $G_1$ is CH, $G_2$ is N, X is $SO_2$, $R_1$ is $CH_2CH_3$, $R_4$ is methyl and $R_3$ are as defined in table B.

Table A-34 provides 19 compounds A-34.001 to A-34.019 of formula I-1 wherein $G_1$ is CH, $G_2$ is N, X is $SO_2$, $R_1$ is $CH_2CH_3$, $R_4$ is ethyl and $R_3$ are as defined in table B.

Table A-35 provides 19 compounds A-35.001 to A-35.019 of formula I-1 wherein $G_1$ is CH, $G_2$ is N, X is $SO_2$, $R_1$ is $CH_2cPr$, $R_4$ is methyl and $R_3$ are as defined in table B.

Table A-36 provides 19 compounds A-36.001 to A-36.019 of formula I-1 wherein $G_1$ is CH, $G_2$ is N, X is $SO_2$, $R_1$ is $CH_2cPr$, $R_4$ is ethyl and $R_3$ are as defined in table B.

Table A-37 provides 19 compounds A-37.001 to A-37.019 of formula I-1 wherein $G_1$ is CH, $G_2$ is CH, X is S, $R_1$ is $CH_2CH_3$, $R_4$ is methyl and $R_3$ are as defined in table B.

Table A-38 provides 19 compounds A-38.001 to A-38.019 of formula I-1 wherein $G_1$ is CH, $G_2$ is CH, X is S, $R_1$ is $CH_2CH_3$, $R_4$ is ethyl and $R_3$ are as defined in table B.

Table A-39 provides 19 compounds A-39.001 to A-39.019 of formula I-1 wherein $G_1$ is CH, $G_2$ is CH, X is S, $R_1$ is $CH_2cPr$, $R_4$ is methyl and $R_3$ are as defined in table B.

Table A-40 provides 19 compounds A-40.001 to A-40.019 of formula I-1 wherein $G_1$ is CH, $G_2$ is CH, X is S, $R_1$ is $CH_2cPr$, $R_4$ is ethyl and $R_3$ are as defined in table B.

Table A-41 provides 19 compounds A-41.001 to A-41.019 of formula I-1 wherein $G_1$ is CH, $G_2$ is CH, X is SO, $R_1$ is $CH_2CH_3$, $R_4$ is methyl and $R_3$ are as defined in table B.

Table A-42 provides 19 compounds A-42.001 to A-42.019 of formula I-1 wherein $G_1$ is CH, $G_2$ is CH, X is SO, $R_1$ is $CH_2CH_3$, $R_4$ is ethyl and $R_3$ are as defined in table B.

Table A-43 provides 19 compounds A-43.001 to A-43.019 of formula I-1 wherein $G_1$ is CH, $G_2$ is CH, X is SO, $R_1$ is $CH_2cPr$, $R_4$ is methyl and $R_3$ are as defined in table B.

Table A-44 provides 19 compounds A-44.001 to A-44.019 of formula I-1 wherein $G_1$ is CH, $G_2$ is CH, X is SO, $R_1$ is $CH_2cPr$, $R_4$ is ethyl and $R_3$ are as defined in table B.

Table A-45 provides 19 compounds A-45.001 to A-45.019 of formula I-1 wherein $G_1$ is CH, $G_2$ is CH, X is $SO_2$, $R_1$ is $CH_2CH_3$, $R_4$ is methyl and $R_3$ are as defined in table B.

Table A-46 provides 19 compounds A-46.001 to A-46.019 of formula I-1 wherein $G_1$ is CH, $G_2$ is CH, X is $SO_2$, $R_1$ is $CH_2CH_3$, $R_4$ is ethyl and $R_3$ are as defined in table B.

Table A-47 provides 19 compounds A-47.001 to A-47.019 of formula I-1 wherein $G_1$ is CH, $G_2$ is CH, X is $SO_2$, $R_1$ is $CH_2$cPr, $R_4$ is methyl and $R_3$ are as defined in table B.

Table A-48 provides 19 compounds A-48.001 to A-48.019 of formula I-1 wherein $G_1$ is CH, $G_2$ is CH, X is $SO_2$, $R_1$ is $CH_2$cPr, $R_4$ is ethyl and $R_3$ are as defined in table B.

The tables below further illustrate specific compounds of the invention.

(I-2)

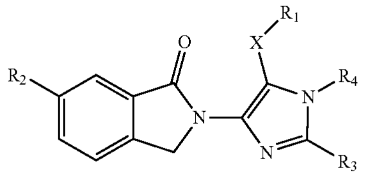

Table C-1 provides 19 compounds C-1.001 to C-1.019 of formula I-2 wherein $R_2$ is $OSO_2CF_3$, X is S, $R_1$ is $CH_2CH_3$, $R_4$ is methyl and $R_3$ are as defined in table B.

Table C-2 provides 19 compounds C-2.001 to C-2.019 of formula I-2 wherein $R_2$ is $OSO_2CF_3$, X is S, $R_1$ is $CH_2$cPr, $R_4$ is methyl and $R_3$ are as defined in table B.

Table C-3 provides 19 compounds C-3.001 to C-3.019 of formula I-2 wherein $R_2$ is $OSO_2CF_3$, X is SO, $R_1$ is $CH_2CH_3$, $R_4$ is methyl and $R_3$ are as defined in table B.

Table C-4 provides 19 compounds C-4.001 to C-4.019 of formula I-2 wherein $R_2$ is $OSO_2CF_3$, X is SO, $R_1$ is $CH_2$cPr, $R_4$ is methyl and $R_3$ are as defined in table B.

Table C-5 provides 19 compounds C-5.001 to C-5.019 of formula I-2 wherein $R_2$ is $OSO_2CF_3$, X is $SO_2$, $R_1$ is $CH_2CH_3$, $R_4$ is methyl and $R_3$ are as defined in table B.

Table C-6 provides 19 compounds C-6.001 to C-6.019 of formula I-2 wherein $R_2$ is $OSO_2CF_3$, X is $SO_2$, $R_1$ is $CH_2$cPr, $R_4$ is methyl and $R_3$ are as defined in table B.

Table C-7 provides 19 compounds C-7.001 to C-7.019 of formula I-2 wherein $R_2$ is $SO_2CF_3$, X is S, $R_1$ is $CH_2CH_3$, $R_4$ is methyl and $R_3$ are as defined in table B.

Table C-8 provides 19 compounds C-8.001 to C-8.019 of formula I-2 wherein $R_2$ is $SO_2CF_3$, X is S, $R_1$ is $CH_2$cPr, $R_4$ is methyl and $R_3$ are as defined in table B.

Table C-9 provides 19 compounds C-9.001 to C-9.019 of formula I-2 wherein $R_2$ is $SO_2CF_3$, X is SO, $R_1$ is $CH_2CH_3$, $R_4$ is methyl and $R_3$ are as defined in table B.

Table C-10 provides 19 compounds C-10.001 to C-10.019 of formula I-2 wherein $R_2$ is $SO_2CF_3$, X is SO, $R_1$ is $CH_2$cPr, $R_4$ is methyl and $R_3$ are as defined in table B.

Table C-11 provides 19 compounds C-11.001 to C-11.019 of formula I-2 wherein $R_2$ is $SO_2CF_3$, X is $SO_2$, $R_1$ is $CH_2CH_3$, $R_4$ is methyl and $R_3$ are as defined in table B.

Table C-12 provides 19 compounds C-12.001 to C-12.019 of formula I-2 wherein $R_2$ is $SO_2CF_3$, X is $SO_2$, $R_1$ is $CH_2$cPr, $R_4$ is methyl and $R_3$ are as defined in table B.

Table C-13 provides 19 compounds C-13.001 to C-13.019 of formula I-2 wherein $R_2$ is $OCF_3$, X is S, $R_1$ is $CH_2CH_3$, $R_4$ is methyl and $R_3$ are as defined in table B.

Table C-14 provides 19 compounds C-14.001 to C-14.019 of formula I-2 wherein $R_2$ is $OCF_3$, X is S, $R_1$ is $CH_2$cPr, $R_4$ is methyl and $R_3$ are as defined in table B.

Table C-15 provides 19 compounds C-15.001 to C-15.019 of formula I-2 wherein $R_2$ is $OCF_3$, X is SO, $R_1$ is $CH_2CH_3$, $R_4$ is methyl and $R_3$ are as defined in table B.

Table C-16 provides 19 compounds C-16.001 to C-16.019 of formula I-2 wherein $R_2$ is $OCF_3$, X is SO, $R_1$ is $CH_2$cPr, $R_4$ is methyl and $R_3$ are as defined in table B.

Table C-17 provides 19 compounds C-17.001 to C-17.019 of formula I-2 wherein $R_2$ is $OCF_3$, X is $SO_2$, $R_1$ is $CH_2CH_3$, $R_4$ is methyl and $R_3$ are as defined in table B.

Table C-18 provides 19 compounds C-18.001 to C-18.019 of formula I-2 wherein $R_2$ is $OCF_3$, X is $SO_2$, $R_1$ is $CH_2$cPr, $R_4$ is methyl and $R_3$ are as defined in table B.

Table C-19 provides 19 compounds C-19.001 to C-19.019 of formula I-2 wherein $R_2$ is $SCF_3$, X is S, $R_1$ is $CH_2CH_3$, $R_4$ is methyl and $R_3$ are as defined in table B.

Table C-20 provides 19 compounds C-20.001 to C-20.019 of formula I-2 wherein $R_2$ is $SCF_3$, X is S, $R_1$ is $CH_2$cPr, $R_4$ is methyl and $R_3$ are as defined in table B.

Table C-21 provides 19 compounds C-21.001 to C-21.019 of formula I-2 wherein $R_2$ is $SCF_3$, X is SO, $R_1$ is $CH_2CH_3$, $R_4$ is methyl and $R_3$ are as defined in table B.

Table C-22 provides 19 compounds C-22.001 to C-22.019 of formula I-2 wherein $R_2$ is $SCF_3$, X is SO, $R_1$ is $CH_2$cPr, $R_4$ is methyl and $R_3$ are as defined in table B.

Table C-23 provides 19 compounds C-23.001 to C-23.019 of formula I-2 wherein $R_2$ is $SCF_3$, X is $SO_2$, $R_1$ is $CH_2CH_3$, $R_4$ is methyl and $R_3$ are as defined in table B.

Table C-24 provides 19 compounds C-24.001 to C-24.019 of formula I-2 wherein $R_2$ is $SCF_3$, X is $SO_2$, $R_1$ is $CH_2$cPr, $R_4$ is methyl and $R_3$ are as defined in table B.

The tables below further illustrate specific compounds of the invention.

(I-3)

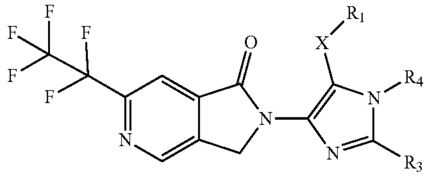

Table D-1 provides 19 compounds D-1.001 to D-1.019 of formula I-3 wherein X is S, $R_1$ is $CH_2CH_3$, $R_4$ is methyl and $R_3$ are as defined in table B.

Table D-2 provides 19 compounds D-2.001 to D-2.019 of formula I-3 wherein X is S, $R_1$ is $CH_2CH_3$, $R_4$ is ethyl and $R_3$ are as defined in table B.

Table D-3 provides 19 compounds D-3.001 to D-3.019 of formula I-3 wherein X is S, $R_1$ is $CH_2$cPr, $R_4$ is methyl and $R_3$ are as defined in table B.

Table D-4 provides 19 compounds D-4.001 to D-4.019 of formula I-3 wherein X is S, $R_1$ is $CH_2$cPr, $R_4$ is ethyl and $R_3$ are as defined in table B.

Table D-5 provides 19 compounds D-5.001 to D-5.019 of formula I-3 wherein X is SO, $R_1$ is $CH_2CH_3$, $R_4$ is methyl and $R_3$ are as defined in table B.

Table D-6 provides 19 compounds D-6.001 to D-6.019 of formula I-3 wherein X is SO, $R_1$ is $CH_2CH_3$, $R_4$ is ethyl and $R_3$ are as defined in table B.

Table D-7 provides 19 compounds D-7.001 to D-7.019 of formula I-3 wherein X is SO, $R_1$ is $CH_2$cPr, $R_4$ is methyl and $R_3$ are as defined in table B.

Table D-8 provides 19 compounds D-8.001 to D-8.019 of formula I-3 wherein X is SO, $R_1$ is $CH_2$cPr, $R_4$ is ethyl and $R_3$ are as defined in table B.

Table D-9 provides 19 compounds D-9.001 to D-9.019 of formula I-3 wherein X is $SO_2$, $R_1$ is $CH_2CH_3$, $R_4$ is methyl and $R_3$ are as defined in table B.

Table D-10 provides 19 compounds D-10.001 to D-10.019 of formula I-3 wherein X is $SO_2$, $R_1$ is $CH_2CH_3$, $R_4$ is ethyl and $R_3$ are as defined in table B.

Table D-11 provides 19 compounds D-11.001 to D-11.019 of formula I-3 wherein X is $SO_2$, $R_1$ is $CH_2cPr$, $R_4$ is methyl and $R_3$ are as defined in table B.

Table D-12 provides 19 compounds D-12.001 to D-12.019 of formula I-3 wherein X is $SO_2$, $R_1$ is $CH_2cPr$, $R_4$ is ethyl and $R_3$ are as defined in table B.

The tables below further illustrate specific compounds of the invention.

(I-4)

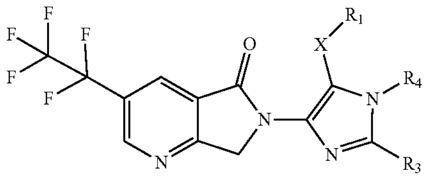

Table E-1 provides 19 compounds E-1.001 to E-1.019 of formula I-4 wherein X is S, $R_1$ is $CH_2CH_3$, $R_4$ is methyl and $R_3$ are as defined in table B.

Table E-2 provides 19 compounds E-2.001 to E-2.019 of formula I-4 wherein X is S, $R_1$ is $CH_2CH_3$, $R_4$ is ethyl and $R_3$ are as defined in table B.

Table E-3 provides 19 compounds E-3.001 to E-3.019 of formula I-4 wherein X is S, $R_1$ is $CH_2cPr$, $R_4$ is methyl and $R_3$ are as defined in table B.

Table E-4 provides 19 compounds E-4.001 to E-4.019 of formula I-4 wherein X is S, $R_1$ is $CH_2cPr$, $R_4$ is ethyl and $R_3$ are as defined in table B.

Table E-5 provides 19 compounds E-5.001 to E-5.019 of formula I-4 wherein X is SO, $R_1$ is $CH_2CH_3$, $R_4$ is methyl and $R_3$ are as defined in table B.

Table E-6 provides 19 compounds E-6.001 to E-6.019 of formula I-4 wherein X is SO, $R_1$ is $CH_2CH_3$, $R_4$ is ethyl and $R_3$ are as defined in table B.

Table E-7 provides 19 compounds E-7.001 to E-7.019 of formula I-4 wherein X is SO, $R_1$ is $CH_2cPr$, $R_4$ is methyl and $R_3$ are as defined in table B.

Table E-8 provides 19 compounds E-8.001 to E-8.019 of formula I-4 wherein X is SO, $R_1$ is $CH_2cPr$, $R_4$ is ethyl and $R_3$ are as defined in table B.

Table E-9 provides 19 compounds E-9.001 to E-9.019 of formula I-4 wherein X is $SO_2$, $R_1$ is $CH_2CH_3$, $R_4$ is methyl and $R_3$ are as defined in table B.

Table E-10 provides 19 compounds E-10.001 to E-10.019 of formula I-4 wherein X is $SO_2$, $R_1$ is $CH_2CH_3$, $R_4$ is ethyl and $R_3$ are as defined in table B.

Table E-11 provides 19 compounds E-11.001 to E-11.019 of formula I-4 wherein X is $SO_2$, $R_1$ is $CH_2cPr$, $R_4$ is methyl and $R_3$ are as defined in table B.

Table E-12 provides 19 compounds E-12.001 to E-12.019 of formula I-4 wherein X is $SO_2$, $R_1$ is $CH_2cPr$, $R_4$ is ethyl and $R_3$ are as defined in table B.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the above-mentioned animal pests are:

from the order Acarina, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Oligonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.; from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtilis, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order *Diptera*, for example,

*Aedes* spp., *Anopheles* spp, *Antherigona soccata, Bactrocera oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gasterophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euschistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., *Vatiga illudens; Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amrasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Solenopsis invicta, Solenopsis* spp. and *Vespa* spp.;

from the order *Isoptera*, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypi-ela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order *Siphonaptera*, for example, *Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; *Citrus* fruit, such as oranges, lemons, grapefruit or tangerines; vegetables, such as spinach, lettuce, *Asparagus*, cabbages, carrots, onions, tomatoes, potatoes or bell peppers; Lauraceae, such as avocado, *Cinnamomum* or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (*e.g. B. elatior, B. semperflorens, B. tubereux*), *Bougainvillea* spp., *Brachycome* spp., *Brassica* spp. (*ornamental*), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena*

*globosa, Heliotropium* spp., *Helianthus* spp., *Hibiscus* spp., *Hortensia* spp., *Hydrangea* spp., *Hypoestes phyllostachya, Impatiens* spp. (*I. walleriana*), *Iresines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (*carnation*), *Canna* spp., *Oxalis* spp., *Bellis* spp., *Pelargonium* spp. (*P. peltatum, P. Zonale*), *Viola* spp. (*pansy*), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (*rose*), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. oleracea, B. pekinensis, B. rapa*), *Capsicum annuum, Cicer arietinum, Cichorium endivia, Cichorium* spp. (*C. intybus, C. endivia*), *Citrullus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosmarinus* spp., *Salvia* spp., *Scorzonera hispanica, Solanum melongena, Spinacea oleracea, Valerianella* spp. (*V. locusta, V. eriocarpa*) and *Vicia faba.*

Preferred ornamental species include African violet, *Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johns wort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo suppressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo suppressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoplolaimus* species; false rootknot nematodes, *Nacobbus* species; Needle nematodes, *Longidorus elongatus* and other *Longidorus* species; *Pin nematodes, Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; *Citrus* nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. nemoralis*); *ochlodina; Deroceras* (*D. agrestis, D. empiricorum, D. laeve, D. reticulatum*); *Discus* (*D. rotundatus*); *Euomphalia; Galba* (*G. truncata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides.*

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus.*

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1 Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (*Diptera*) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, Anthracnose, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF—YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO 2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, |

TABLE B-continued

| Examples of native woodborers of economic importance. | | |
|---|---|---|
| Family | Species | Host or Crop Infested |
| | | Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, Rhododendron, Azalea, Laurel, Poplar, Willow, Mulberry |
| | *Oncideres cingulata* | Hickory, Pecan, Persimmon, Elm, Sourwood, Basswood, Honeylocust, Dogwood, Eucalyptus, Oak, Hackberry, Maple, Fruit trees |
| | *Saperda calcarata* | Poplar |
| | *Strophiona nitens* | Chestnut, Oak, Hickory, Walnut, Beech, Maple |
| Scolytidae | *Corthylus columbianus* | Maple, Oak, Yellow-poplar, Beech, Boxelder, Sycamore, Birch, Basswood, Chestnut, Elm |
| | *Dendroctonus frontalis* | Pine |
| | *Dryocoetes betulae* | Birch, Sweetgum, Wild cherry, Beech, Pear |
| | *Monarthrum fasciatum* | Oak, Maple, Birch, Chestnut, Sweetgum, Blackgum, Poplar, Hickory, Mimosa, Apple, Peach, Pine |
| | *Phloeotribus liminaris* | Peach, Cherry, Plum, Black cherry, Elm, Mulberry, Mountain-ash |
| | *Pseudopityophthorus pruinosus* | Oak, American beech, Black cherry, Chickasaw plum, Chestnut, Maple, Hickory, Hornbeam, Hophornbeam |
| Sesiidae | *Paranthrene simulans* | Oak, American chestnut |
| | *Sannina uroceriformis* | Persimmon |
| | *Synanthedon exitiosa* | Peach, Plum, Nectarine, Cherry, Apricot, Almond, Black cherry |
| | *Synanthedon pictipes* | Peach, Plum, Cherry, Beach, Black Cherry |
| | *Synanthedon rubrofascia* | Tupelo |
| | *Synanthedon scitula* | Dogwood, Pecan, Hickory, Oak, Chestnut, Beech, Birch, Black cherry, Elm, Mountain-ash, Viburnum, Willow, Apple, Loquat, Ninebark, Bayberry |
| | *Vitacea polistiformis* | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *Ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermuda grass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of Such Parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order *Diptera* and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order *Siphonaptera*, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-*stigmata*, for example *Argas* spp., *Ornithodorus* spp., *Otobius* spp., *Ixodes* spp., *Amblyomma* spp., *Boophilus* spp., *Dermacentor* spp., *Haemaphysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Protium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capuchins, Heterobostrychus brunneus, Sinoxylon* spec. and *Dinoderus minutus*, and also hymenopterans such as *Sirexjuvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina.*

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood New Jersey (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $Cl_2$—$C_8$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
- active ingredient: 1 to 95%, preferably 60 to 90%
- surface-active agent: 1 to 30%, preferably 5 to 20%
- liquid carrier: 1 to 80%, preferably 1 to 35%

Dusts:
- active ingredient: 0.1 to 10%, preferably 0.1 to 5%
- solid carrier: 99.9 to 90%, preferably 99.9 to 99%

Suspension Concentrates:
- active ingredient: 5 to 75%, preferably 10 to 50%
- water: 94 to 24%, preferably 88 to 30%
- surface-active agent: 1 to 40%, preferably 2 to 30%

Wettable Powders:
- active ingredient: 0.5 to 90%, preferably 1 to 80%
- surface-active agent: 0.5 to 20%, preferably 1 to 15%
- solid carrier: 5 to 95%, preferably 15 to 90%

Granules:
- active ingredient: 0.1 to 30%, preferably 0.1 to 15%
- solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |

-continued

| Powders for dry seed treatment | a) | b) | c) |
|---|---|---|---|
| highly dispersed silicic acid | 5% | 5% | — |
| Kaolin | 65% | 40% | — |
| Talcum | — | | 20% |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-tor-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$ or $(M-H)^-$.

LCMS Methods:

Method 1:

Spectra were recorded on a Mass Spectrometer from Waters (SQD Single quadrupole mass spectrometer) equipped with an electrospray source (Polarity: positive or negative ions, Full Scan, Capillary: 3.00 kV, Cone range: 41 V, Source Temperature: 150° C., Desolvation Temperature: 500° C., Cone Gas Flow: 50 L/Hr, Desolvation Gas Flow: 1000 L/Hr, Mass range: 110 to 800 Da) and a H-Class UPLC from Waters: quaternary pump, heated column compartment and diode-array detector. Column: Acquity UPLC HSS T3 C18, 1.8 μm, 30×2.1 mm, Temp: 40° C., DAD Wavelength range (nm): 200 to 400, Solvent Gradient: A=water+5% Acetonitrile+0.1% HCOOH, B=Acetonitrile+0.05% HCOOH: gradient: 0 min 10% B; 0-0.2 min 10-50% B; 0.2-0.7 min 50-100% B; 0.7-1.3 min 100% B; 1.3-1.4 min 100-10% B; 1.4-1.6 min 10% B; Flow (mL/min) 0.6.

Method 2:

Spectra were recorded on a Mass Spectrometer from Agilent Technologies (6410 Triple Quadrupole mass spectrometer) equipped with an equipped with an electrospray source (Polarity: positive or negative ions, MS2 Scan, Capillary: 4.00 kV, Fragmentor: 100 V, Desolvation Temperature: 350° C., Gas Flow: 11 L/min, Nebulizer Gas: 45 psi, Mass range: 110 to 1000 Da) and a 1200 Series HPLC from Agilent: quaternary pump, heated column compartment and diode-array detector. Column: KINETEX EVO C18, 2.6 μm, 50×4.6 mm, Temp: 40° C., DAD Wavelength range (nm): 210 to 400, Solvent Gradient: A=water+5% Acetonitrile+0.1% HCOOH, B=Acetonitrile+0.1% HCOOH: gradient: 0 min 10% B, 90% A; 0.9-1.8 min 100% B; 1.8-2.2 min 100-10% B; 2.2-2.5 min 10% B; Flow (mL/min) 1.8.

Example P1: Preparation of 2-[2-(1-cyclopropylpyrazol-4-yl)-5-ethylsulfonyl-1-methyl-imidazol-4-yl]-6-(trifluoromethoxy)isoindolin-1-one (Compound P1)

(P1)

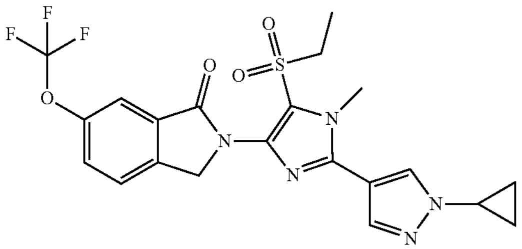

Step A1: Preparation of methyl 2-amino-5-(trifluoromethoxy)benzoate (Intermediate I-1)

(I-1)

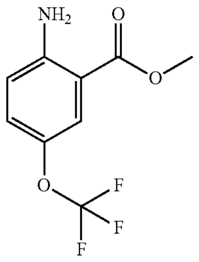

To a solution of 2-amino-5-(trifluoromethoxy)benzoic acid (5.0 g, 23 mmol) in N,N-dimethylformamide (50 mL) were added potassium carbonate (6.3 g, 45 mmol) and iodomethane (1.4 mL, 23 mmol) at room temperature. The reaction mixture was stirred overnight at room temperature. The reaction mass was quenched with water (300 mL) and extracted with ethyl acetate (3×100 mL). The organic layers were dried over sodium sulfate, filtered and concentrated in vacuo. The crude was purified by combiflash (silica gel, 0-10% ethyl acetate in cyclohexane) to afford methyl 2-amino-5-(trifluoromethoxy)benzoate. LCMS (method 2): Rt=1.46 min, m/z=236 $(M+H)^+$. $^1$H NMR (400 MHz, $CDCl_3$) δ ppm: 3.89 (s, 3H), 5.80 (br s, 2H), 6.66 (d, 1H), 7.15 (ddt, 1H), 7.73 (d, 1H).

Step A2: Preparation of methyl 2-bromo-5-(trifluoromethoxy)benzoate (Intermediate I-2)

(I-2)

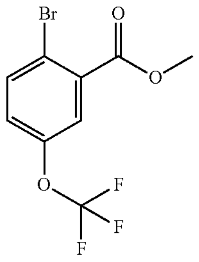

To a 0° C. cooled solution of methyl 2-amino-5-(trifluoromethoxy)benzoate (intermediate I-1 prepared as described above) (7.3 g, 31 mmol) in hydrobromic acid (48% in water, 73 mL) was added dropwise a solution of sodium nitrite (4.3 g, 62 mmol) in water (22 mL). The reaction mixture was stirred at 0° C. for 30 minutes, before copper(I) bromide (8.0 g, 56 mmol) was added. The reaction mixture was stirred for additional 30 minutes at 0° C., and then at room temperature for 5 hours. The reaction mixture was diluted with water (100 mL) and extracted with ethyl acetate (3×200 mL). The combined organic layers were dried over sodium sulfate, filtered and concentrated in vacuo. The crude was purified by combiflash (silica gel, 0-8% ethyl acetate in cyclohexane) to afford methyl 2-bromo-5-(trifluoromethoxy)benzoate. $^1$H NMR (400 MHz, $CDCl_3$) δ ppm: 3.96 (s, 3H), 7.22 (m, 1H), 7.66-7.73 (m, 2H).

Step A3: Preparation of methyl 2-methyl-5-(trifluoromethoxy)benzoate (Intermediate I-3)

(I-3)

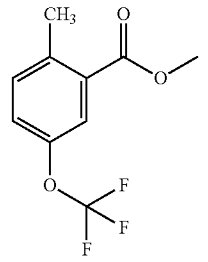

In a flask were charged methyl 2-bromo-5-(trifluoromethoxy)benzoate (intermediate I-2 prepared as described above) (5.3 g, 18 mmol), methylboronic acid (3.3 g, 53 mmol), tripotassium phosphate (11 g, 53 mmol), tricyclohexylphosphane (0.50 g, 1.8 mmol), followed by toluene (64 mL) and water (11 mL). The flask was purged with nitrogen for 10 minutes, before adding palladium(II) acetate (0.20 g, 0.89 mmol) and continuing purging for additional 10 minutes. The reaction mixture was heated up to 100° C. and stirred for 3 hours. The reaction mixture was quenched with water (50 mL) and extracted with ethyl acetate (3×50 mL). The combined organic layers were dried over sodium sulfate, filtered and concentrated in vacuo. The crude was purified by combiflash (silica gel, 100% cyclohexane) to afford methyl 2-methyl-5-(trifluoromethoxy)benzoate. $^1$H NMR (400 MHz, $CDCl_3$) δ ppm: 2.61 (s, 3H), 3.92 (s, 3H), 7.27-7.30 (m, 2H), 7.78 (s, 1H).

Step A4: Preparation of methyl 2-(bromomethyl)-5-(trifluoromethoxy)benzoate (Intermediate I-4)

(I-4)

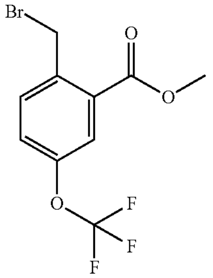

To a solution of methyl 2-methyl-5-(trifluoromethoxy) benzoate (intermediate I-3 prepared as described above) (1.9 g, 8.1 mmol) in tetrachloromethane (65 mL) were added N-bromosuccinimide (2.0 g, 11 mmol) and benzoyl peroxide (0.70 g, 2.0 mmol) at room temperature. The reaction mixture was heated up to 70° C. and stirred for 3 hours. After cooling down to room temperature, the reaction mixture was diluted with ice cold water (100 mL) and extracted with dichloromethane (3×50 mL). The combined organic layers were washed with brine (50 mL), dried over sodium sulfate, filtered and concentrated in vacuo. The crude was purified by combiflash (silica gel, 5-10% ethyl acetate in cyclohexane) to afford methyl 2-(bromomethyl)-5-(trifluoromethoxy)benzoate. $^1$H NMR (400 MHz, $CDCl_3$) δ ppm: 3.97 (s, 3H), 4.95 (s, 2H), 7.50-7.56 (m, 1H), 7.83 (d, 1H), 8.07-8.12 (m, 1H).

Step B1: Preparation of ethyl 1-methylimidazole-4-carboxylate (Intermediate I-5)

(I-5)

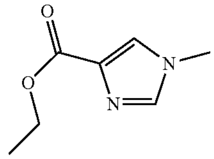

To a solution of 1-methylimidazole-4-carboxylic acid (20.0 g, 159 mmol) in ethanol (200 mL) was added N,N-dimethylformamide (1.23 mL, 15.9 mmol) in one portion via syringe. The mixture was cooled down to 0-5° C. Then, thionyl chloride (34.7 mL, 476 mmol) was added dropwise over a period of 15 minutes at 0-5° C. The cooling was then removed, and the mixture was stirred from 0-5° C. to 24° C. for one hour. The reaction mixture was stirred at 80° C. for 6 hours under nitrogen atmosphere. After completion, reaction mass was concentrated in vacuo, quenched with an aqueous saturated sodium bicarbonate solution (100 mL) and extracted with ethyl acetate (3×200 mL). The combined organic layers were washed with brine, dried over sodium sulfate, filtered and concentrated in vacuo to afford ethyl 1-methylimidazole-4-carboxylate. This material was used as such in the next step. LCMS (method 2): Rt=0.31 min, m/z=155 $(M+H)^+$.

Step B2: Preparation of ethyl 2-bromo-1-methyl-imidazole-4-carboxylate (Intermediate I-6)

(I-6)

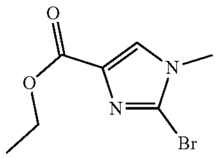

To a solution of ethyl 1-methylimidazole-4-carboxylate (intermediate I-5 prepared as described above) (20.0 g, 130 mmol) in tetrahydrofuran (200 mL) were added N-bromosuccinimide (23.6 g, 130 mmol) and potassium phosphate tribasic (29.0 g, 130 mmol) and the mixture was stirred at room temperature for 16 hours under nitrogen atmosphere. The reaction mixture was diluted with water (100 mL) and extracted with ethyl acetate (3×100 mL). The organic layers were dried over sodium sulfate, filtered and concentrated in vacuo. The crude was purified by combiflash (silica gel, 35% ethyl acetate in cyclohexane) to afford ethyl 2-bromo-1-methyl-imidazole-4-carboxylate as a white solid. LCMS (method 2): Rt=0.85 min, m/z=233 $(M+H)^+$. $^1$H NMR (400 MHz, $CDCl_3$) δ ppm: 1.37 (t, 3H) 3.68 (s, 3H) 4.36 (q, 2H) 7.64 (s, 1H).

Step B3: Preparation of ethyl 2-bromo-5-ethylsulfanyl-1-methyl-imidazole-4-carboxylate (Intermediate I-7)

(I-7)

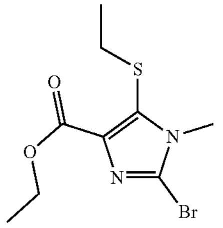

To a solution of N-isopropylpropan-2-amine (2.4 mL, 17 mmol) in tetrahydrofuran (20 mL) was added n-butyllithium (2.0 mol/L in cyclohexane, 10 mL, 20 mmol) at −78° C. under nitrogen atmosphere. The resulting solution was stirred at −78° C. for 30 minutes. Then the solution was warmed to 0° C. and stirred at 0° C. for 30 minutes. Then, this freshly prepared solution of lithium diisopropylamide was added dropwise to a solution of ethyl 2-bromo-1-methyl-imidazole-4-carboxylate (intermediate I-6 prepared as described above) (2.5 g, 11 mmol) and (ethyldisulfanyl) ethane (2.6 g, 21 mmol) in tetrahydrofuran (25 mL) at −78° C. The resulting solution was stirred at −78° C. for 30 minutes. The reaction mixture was quenched with an aqueous saturated ammonium chloride solution and extracted with ethyl acetate (2×100 mL). The organic layers were washed with brine, dried over sodium sulfate, filtered and concentrated in vacuo. The crude was purified by combiflash (silica gel, 20% ethyl acetate in cyclohexane) to afford pure ethyl 2-bromo-5-ethylsulfanyl-1-methyl-imidazole-4-carboxylate as a brown thick oil. LCMS (method 2): Rt=1.36 min, m/z=293 $(M+H)^+$. $^1H$ NMR (400 MHz, $CDCl_3$) δ ppm: 1.21 (t, 3H) 1.40 (t, 3H) 2.92 (q, 2H) 3.71 (s, 3H) 4.40 (q, 2H).

Step B4: Preparation of ethyl 2-bromo-5-ethylsulfonyl-1-methyl-imidazole-4-carboxylate (Intermediate I-8)

(I-8)

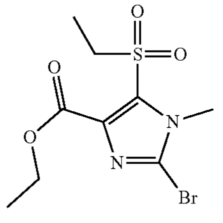

To 0° C. cooled solution of ethyl 2-bromo-5-ethylsulfanyl-1-methyl-imidazole-4-carboxylate (intermediate I-7 prepared as described above) (4.50 g, 15.3 mmol) in acetonitrile (45 mL) was added 3-chlorobenzenecarboperoxoic acid (8.32 g, 33.8 mmol, 70 mass %) at 0° C. The reaction mixture was stirred at room temperature for 4 hours. After completion, the reaction mass was quenched with an aqueous 2N sodium hydroxide (50 mL) and water (50 mL), extracted with ethyl acetate (2×100 mL). The combined organic layers were washed with brine (50 mL), dried over sodium sulfate, filtered and concentrated in vacuo. The crude was purified by combiflash (silica gel, 30% ethyl acetate in cyclohexane) to afford ethyl 2-bromo-5-ethylsulfonyl-1-methyl-imidazole-4-carboxylate as a thick oil. LCMS (Method 2): Rt=1.31 min, m/z=325 $(M+H)^+$. $^1H$ NMR (400 MHz, $CDCl_3$) δ ppm: 1.35-1.44 (m, 6H) 3.67 (q, 2H) 3.97 (s, 3H) 4.43 (q, 2H).

Step B5: Preparation of ethyl 2-(1-cyclopropylpyrazol-4-yl)-5-ethylsulfonyl-1-methyl-imidazole-4-carboxylate (Intermediate I-9)

(I-9)

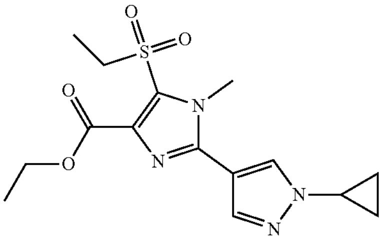

In a microwave vial, a stirred solution of ethyl 2-bromo-5-ethylsulfonyl-1-methyl-imidazole-4-carboxylate (intermediate I-8 prepared as described above) (0.5 g, 2 mmol) in 1,4-dioxane (9 mL) was added cesium carbonate (2.0 g, 5 mmol) and 1-cyclopropyl-4-(4,4,5,5-tetramethyl-1,3,2-dioxaborolan-2-yl)pyrazole (1.0 g, 5 mmol) at room temperature. Reaction mass was degassed with nitrogen for 15 minutes, then tetrakis(triphenylphosphine)palladium (0.2 g, 0.2 mmol) was added under nitrogen atmosphere. The vial was sealed and transferred to microwave, heated at 110° C. for 30 minutes under microwave irradiation. The reaction mixture was quenched with water (50 mL) and extracted with ethyl acetate (2×50 mL). The combined organic layers were dried over dried over sodium sulfate, filtered and concentrated in vacuo. The crude was purified by combiflash (silica gel, 25% ethyl acetate in cyclohexane) to afford ethyl 2-(1-cyclopropylpyrazol-4-yl)-5-ethylsulfonyl-1-methyl-imidazole-4-carboxylate as a thick mass. LCMS (method 2): Rt=1.23 min, m/z=353 $(M+H)^+$. $^1H$ NMR (400 MHz, $CDCl_3$) δ ppm: 1.06-1.22 (m, 4H) 1.41 (dt, 6H) 3.63-3.71 (m, 3H) 4.01 (s, 3H) 4.45 (q, 2H) 7.79 (s, 1H) 7.97 (s, 1H).

Step B6: Preparation of 2-(1-cyclopropylpyrazol-4-yl)-5-ethylsulfonyl-1-methyl-imidazole-4-carboxylic Acid (Intermediate I-10)

(I-10)

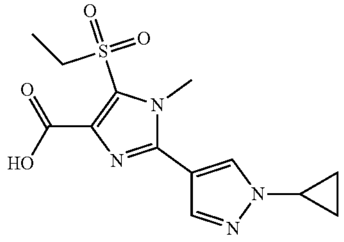

To a solution of ethyl 2-(1-cyclopropylpyrazol-4-yl)-5-ethylsulfonyl-1-methyl-imidazole-4-carboxylate (intermediate I-9 prepared as described above) (1.17 g, 3.32 mmol) in tetrahydrofuran (17 mL) was added a solution of lithium hydroxide monohydrate (0.21 g, 4.98 mmol) in water (5 mL) at room temperature. The reaction mixture was stirred at room temperature for 3 hours. Lithium hydroxide monohydrate (0.21 g, 4.98 mmol) was added again and the mixture was stirred at room temperature for additional 10 hours. After completion, reaction mixture was quenched with water (50 mL), acidified with 2N aqueous hydrochloric acid (20 mL), extracted with ethyl acetate (3x50 mL). The combined organic layers were washed with brine (30 mL), dried over anhydrous sodium sulfate, filtered and concentrated in vacuo to afford 2-(1-cyclopropylpyrazol-4-yl)-5-ethylsulfonyl-1-methyl-imidazole-4-carboxylic acid as a white solid. This material was used as such in the next step. LCMS (method 2): Rt=0.90 min, m/z=325 $(M+H)^+$.

Step B7: Preparation of tert-butyl N-[2-(1-cyclopropylpyrazol-4-yl)-5-ethylsulfonyl-1-methyl-imidazol-4-yl]carbamate (Intermediate I-11)

(I-11)

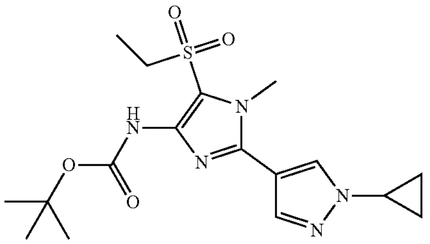

To a solution of 2-(1-cyclopropylpyrazol-4-yl)-5-ethylsulfonyl-1-methyl-imidazole-4-carboxylic acid (intermediate I-10 prepared as described above) (1.10 g, 3.39 mmol) in tert-butanol (22 mL) was added triethylamine (0.56 g, 5.43 mmol) at room temperature. The mixture was heated to 90° C. and stirred for 10 minutes. Diphenylphosphoryl azide (1.19 mL, 5.43 mmol) was added dropwise over a period of 15 minutes and the resulting reaction mixture was stirred at 90° C. for 40 minutes. The reaction mass was allowed to cool to room temperature. The reaction mass was quenched with ice cold water (50 mL), extracted with ethyl acetate (3x200 mL). The combined organic layers were dried over sodium sulfate, filtered and concentrated in vacuo. The crude was purified by combiflash (silica gel, 80% ethyl acetate in cyclohexane) to afford tert-butyl N-[2-(1-cyclopropylpyrazol-4-yl)-5-ethylsulfonyl-1-methyl-imidazol-4-yl]carbamate as a white solid. LCMS (method 2): Rt=1.35 min, m/z=396 $(M+H)^+$. $^1H$ NMR (400 MHz, $CDCl_3$) δ ppm: 1.04-1.21 (m, 4H) 1.36 (t, 3H) 1.51 (s, 9H) 3.20 (q, 2H) 3.65 (dt, 1H) 3.87 (s, 3H) 7.77 (s, 1H) 7.90 (s, 1H) 8.06 (s, 1H).

Step C1: Preparation of methyl 2-[[tert-butoxycarbonyl-[2-(1-cyclopropylpyrazol-4-yl)-5-ethylsulfonyl-1-methyl-imidazol-4-yl]amino]methyl]-5-(trifluoromethoxy)benzoate (Intermediate I-12)

(I-12)

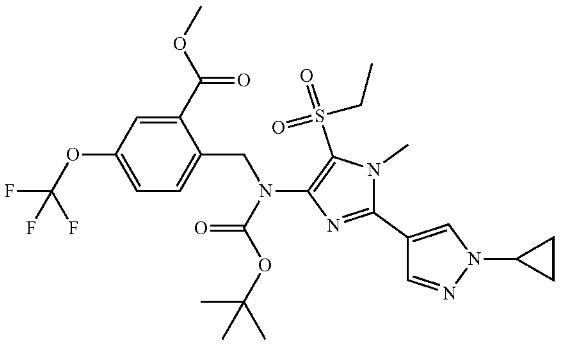

To a stirred solution of tert-butyl N-[2-(1-cyclopropylpyrazol-4-yl)-5-ethylsulfonyl-1-methyl-imidazol-4-yl]carbamate (intermediate I-11 prepared as described above) (0.40 g, 1.01 mmol) in acetonitrile (8 mL) was added methyl 2-(bromomethyl)-5-(trifluoromethoxy)benzoate (intermediate I-4 prepared as described above) (0.41 g, 1.31 mmol) and cesium carbonate (0.50 g, 1.52 mmol) at room temperature. The reaction mixture was stirred at 50° C. for 4 hours, then quenched with ice cold water (50 mL) and extracted with ethyl acetate (3x50 mL). The combined organic layers were dried over sodium sulfate, filtered and concentrated in vacuo. The crude was purified by combiflash (silica gel, 55% ethyl acetate in cyclohexane) to afford methyl 2-[[tert-butoxycarbonyl-[2-(1-cyclopropylpyrazol-4-yl)-5-ethylsulfonyl-1-methyl-imidazol-4-yl]amino]methyl]-5-(trifluoromethoxy)benzoate as a gummy mass. LCMS (method 2): Rt=1.62 min, m/z=628 $(M+H)^+$.

Step $C_2$: Preparation of methyl 2-[[[2-(1-cyclopropylpyrazol-4-yl)-5-ethylsulfonyl-1-methyl-imidazol-4-yl]amino]methyl]-5-(trifluoromethoxy)benzoate (Intermediate I-13)

(I-13)

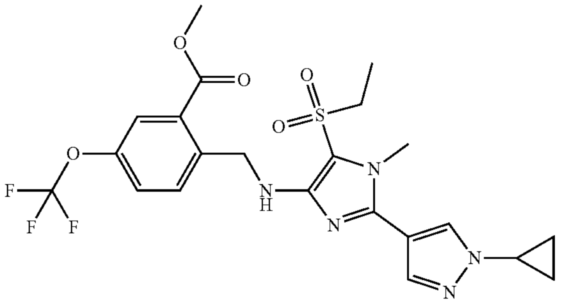

To 0° C. cooled solution of methyl 2-[[tert-butoxycarbonyl-[2-(1-cyclopropylpyrazol-4-yl)-5-ethylsulfonyl-1-methyl-imidazol-4-yl]amino]methyl]-5-(trifluoromethoxy) benzoate (intermediate I-12 prepared as described above) (0.55 g, 0.88 mmol) in trifluoromethylbenzene (11 mL) was added 2,2,2-trifluoroacetic acid (1.0 mL, 13.15 mmol) dropwise. The reaction mixture was stirred at room temperature for 3 hours. Reaction was monitored by TLC. TLC shows formation of desired product along with some starting material. 2,2,2-trifluoroacetic acid (0.67 mL, 8.8 mmol) was added to the reaction mass and the mixture was stirred at room temperature for additional 16 hours. The reaction mass was concentrated in vacuo, quenched with a saturated aqueous sodium bicarbonate solution (20 mL) and water (10 mL). The aqueous layer was extracted with ethyl acetate (3×50 mL), the combined organic layers were washed with brine (50 mL), dried over sodium sulfate, filtered and concentrated in vacuo. The crude was purified by combiflash (silica gel, 55% ethyl acetate in cyclohexane) to afford methyl 2-[[[2-(1-cyclopropylpyrazol-4-yl)-5-ethylsulfonyl-1-methyl-imidazol-4-yl]amino]methyl]-5-(trifluoromethoxy)benzoate as a gummy mass. LCMS (method 2): Rt=1.54 min, m/z=528 $(M+H)^+$.

Step C3: Preparation of 2-[[[2-(1-cyclopropylpyrazol-4-yl)-5-ethylsulfonyl-1-methyl-imidazol-4-yl]amino]methyl]-5-(trifluoromethoxy)benzoic Acid (Intermediate I-14)

(I-14)

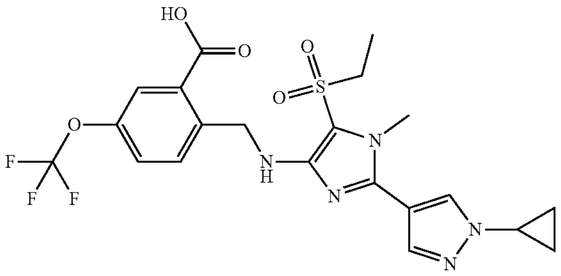

To a solution of methyl 2-[[[2-(1-cyclopropylpyrazol-4-yl)-5-ethylsulfonyl-1-methyl-imidazol-4-yl]amino]methyl]-5-(trifluoromethoxy)benzoate (intermediate I-13 prepared as described above) (0.40 g, 0.76 mmol) in tetrahydrofuran (6 mL) was added a solution of lithium hydroxide monohydrate (0.05 g, 1.14 mmol) in water (1.6 mL) at room temperature. The reaction mixture was stirred at room temperature for 16 hours. Progress of reaction was monitored by TLC and LCMS. LCMS shows desired product formation along with some starting material. Lithium hydroxide monohydrate (0.05 g, 1.14 mmol) was added to the reaction mass and the mixture was stirred at room temperature for additional 6 hours. After completion, reaction mixture was quenched with water (20 mL), acidify with an aqueous 2N hydrochloric acid (10 mL), extracted with ethyl acetate (3×50 mL). The combined organic layers were washed with brine (50 mL), dried over anhydrous sodium sulfate, filtered and concentrated in vacuo to afford 2-[[[2-(1-cyclopropylpyrazol-4-yl)-5-ethylsulfonyl-1-methyl-imidazol-4-yl]amino]methyl]-5-(trifluoromethoxy)benzoic acid as a gummy mass. This material was used as such in the next step. LCMS (method 1): Rt=1.04 min, m/z=512 $(M-H)^-$.

Step C4: Preparation of 2-[2-(1-cyclopropylpyrazol-4-yl)-5-ethylsulfonyl-1-methyl-imidazol-4-yl]-6-(trifluoromethoxy)isoindolin-1-one (P1)

(P1)

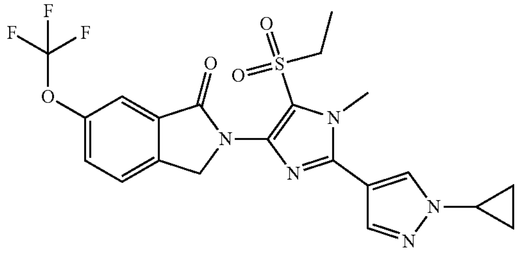

To a 0° C. cooled solution of 2-[[[2-(1-cyclopropylpyrazol-4-yl)-5-ethylsulfonyl-1-methyl-imidazol-4-yl]amino]methyl]-5-(trifluoromethoxy)benzoic acid (0.40 g, 0.78 mmol) in pyridine (4 mL) was added phosphorus oxychloride (0.15 mL, 1.558 mmol) dropwise under nitrogen atmosphere. The reaction mixture was stirred at 0° C. for 45 minutes. The reaction mixture was stirred at 0 to 10° C. for 20 minutes. The reaction mass was quenched with ice cold water (30 mL) and extracted with ethyl acetate (2×50 mL). The combined organic layers were washed with brine (30 mL), dried over anhydrous sodium sulfate, filtered and concentrated in vacuo. The crude was purified by combiflash (silica gel, 80-90% ethyl acetate in cyclohexane) to afford pure compound 2-[2-(1-cyclopropylpyrazol-4-yl)-5-ethylsulfonyl-1-methyl-imidazol-4-yl]-6-(trifluoromethoxy)isoindolin-1-one (compound P1) as a white solid. LCMS (method 2): Rt=1.44 min, m/z=496 $(M+H)^+$. $^1H$ NMR (400 MHz, $CDCl_3$) δ ppm: 1.09-1.27 (m, 4H) 1.49 (t, 3H) 3.60-3.74 (m, 3H) 4.00 (s, 3H) 4.94 (s, 2H) 7.47 (dd, 1H) 7.56 (d, 1H) 7.78 (s, 1H) 7.84 (s, 1H) 7.94 (s, 1H).

Example P3: Preparation of 6-[2-(3-cyclopropyl-4,5-dihydroisoxazol-5-yl)-5-ethylsulfonyl-1-methyl-imidazol-4-yl]-3-(trifluoromethyl)-7H-pyrrolo[3,4-b]pyridin-5-one (Compound P3)

(P3)

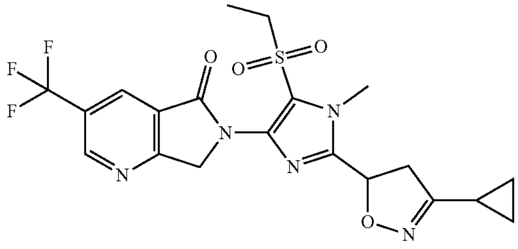

Step A1: Preparation of ethyl 2-chloro-5-(trifluoromethyl)pyridine-3-carboxylate

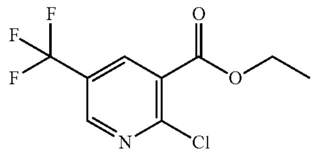 [SMILES: CCOC(=O)c1cc(C(F)(F)F)cnc1Cl]

To a solution of 2-chloro-5-(trifluoromethyl)pyridine-3-carboxylic acid (10 g, 44.3 mmol) in methylsulfinylmethane (100 mL) was added potassium carbonate (12.25 g, 88.7 mmol). The reaction mixture was stirred at room temperature for 5 minutes. Then iodoethane (10.58 g, 66.5 mmol) was added and the reaction mixture was stirred at room temperature for 2 hours. The reaction mass was diluted with iced water and the product extracted with ethyl acetate. The organic layer was washed three times with iced water, then once with brine, dried over sodium sulfate, filtered and concentrated in vacuo to afford ethyl 2-chloro-5-(trifluoromethyl)pyridine-3-carboxylate. This material was used as such in the next step. LCMS (method 1): Rt=1.08 min, m/z=254 (M+H)+. $^1$H NMR (400 MHz, $CDCl_3$) δ ppm 1.44 (t, J=7.15 Hz, 3H) 4.46 (q, J=7.09 Hz, 2H) 8.38 (d, J=2.08 Hz, 1H) 8.77 (dd, J=2.38, 0.67 Hz, 1H).

Step A2: Preparation of ethyl 2-methyl-5-(trifluoromethyl)pyridine-3-carboxylate

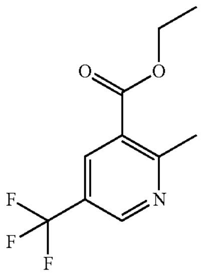 [SMILES: CCOC(=O)c1cc(C(F)(F)F)cnc1C]

In a flask were charged ethyl 2-chloro-5-(trifluoromethyl) pyridine-3-carboxylate (prepared as described above) (11.1 g, 43.8 mmol), methylboronic acid (8.1 g, 131 mmol), tripotassium phosphate (27.9 g, 131 mmol), tricyclohexylphosphane (1.23 g, 4.38 mmol), followed by toluene (111 mL) and water (11 mL). The flask was purged with nitrogen for 10 minutes, before adding palladium(II) acetate (0.49 g, 2.19 mmol) and continuing purging for additional 5 minutes. The reaction mixture was heated to 100° C. and stirred for 8 hours. The reaction mixture was quenched with water (100 mL) and extracted with ethyl acetate (100 mL). The organic layers were dried over sodium sulfate, filtered and concentrated in vacuo. The crude was purified by combiflash (silica gel, 5-10% ethyl acetate in cyclohexane) to afford ethyl 2-methyl-5-(trifluoromethyl)pyridine-3-carboxylate. LCMS (method 1): Rt=1.04 min, m/z=234 (M+H)+. $^1$H NMR (400 MHz, $CDCl_3$) δ ppm 1.45 (t, J=7.15 Hz, 3H) 2.94 (s, 3H) 4.45 (q, J=7.13 Hz, 2H) 8.44 (d, J=2.20 Hz, 1H) 8.86-8.90 (m, 1H).

Step A3: Preparation of ethyl 2-(bromomethyl)-5-(trifluoromethyl)pyridine-3-carboxylate

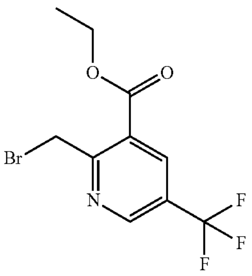 [SMILES: CCOC(=O)c1cc(C(F)(F)F)cnc1CBr]

To a solution of ethyl 2-methyl-5-(trifluoromethyl)pyridine-3-carboxylate (prepared as described above) (6.1 g, 26 mmol) in trifluorobenzene (61 mL) were added N-bromosuccinimide (5.5 g, 30 mmol) and 2,2'-azobis(isobutyronitrile) (0.43 g, 2.6 mmol) at room temperature. The reaction mixture was heated to 90° C. and stirred for 5 hours, then at 80° C. overnight. After cooling to room temperature, the reaction mixture was diluted with water (60 mL) and stirred for 10 minutes. The organic layer was separated. The aqueous layer was extracted with ethyl acetate (150 mL). The combined organic layers were dried over sodium sulfate, filtered and concentrated in vacuo. The crude was purified by combiflash (silica gel, 0-2% ethyl acetate in cyclohexane) to afford ethyl 2-(bromomethyl)-5-(trifluoromethyl)pyridine-3-carboxylate. LCMS (method 1): Rt=1.11 min, m/z=312 (M+H)+. $^1$H NMR (400 MHz, $CDCl_3$) δ ppm: 1.48 (t, J=7.15 Hz, 3H) 4.50 (q, J=7.21 Hz, 2H) 5.08 (s, 2H) 8.52 (d, J=2.08 Hz, 1H) 8.96 (d, J=1.59 Hz, 1H).

Step B1: Preparation of ethyl 5-ethylsulfonyl-1-methyl-2-vinyl-imidazole-4-carboxylate

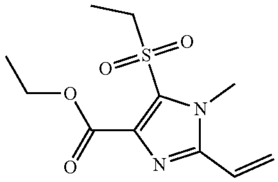 [SMILES: C=Cc1nc(C(=O)OCC)c(S(=O)(=O)CC)n1C]

To a solution of ethyl 2-bromo-5-ethylsulfonyl-1-methyl-imidazole-4-carboxylate (intermediate I-9 prepared as described in example P1 step B4) (1.00 g, 2.92 mmol) in toluene (8 mL) was added tributyl(vinyl)tin (1.08 mL, 3.50 mmol) and the solution was degassed with nitrogen for 10 minutes. Then, [1,1'-bis(diphenylphosphino)ferrocene]dichloropalladium(II) complex (0.0147 g, 0.175 mmol) was added and the reaction mixture was heated in microwave at 130° C. for 1 hour. The reaction mixture was concentrated in vacuo. The residue was dissolved in ethyl acetate, washed twice with water, then once with brine. The organic layer was dried over anhydrous sodium sulfate, filtered and concentrated in vacuo. The crude was purified by combiflash (silica gel, 50% ethyl acetate in cyclohexane) to afford ethyl 5-ethylsulfonyl-1-methyl-2-vinyl-imidazole-4-carboxylate as a brown oil. LCMS (method 2): Rt=0.87 min, m/z=273 $(M+H)^+$. $^1$H NMR (400 MHz, $CDCl_3$) δ ppm: 6.61-6.69 (m, 1H) 6.52-6.48 (m, 1H) 5.79 (dd, J=11.01, 1.25 Hz, 1H) 4.46 (q, 2H) 3.96 (s, 3H) 3.66 (q, 2H) 1.36-1.47 (m, 6H).

Step B2: Preparation of ethyl 2-(3-cyclopropyl-4,5-dihydroisoxazol-5-yl)-5-ethylsulfonyl-1-methyl-imidazole-4-carboxylate

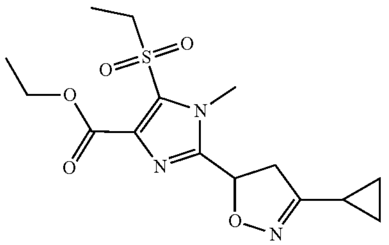 [SMILES: CCOC(=O)c1nc(C2CC(C3CC3)=NO2)n(C)c1S(=O)(=O)CC]

To a solution of ethyl 5-ethylsulfonyl-1-methyl-2-vinyl-imidazole-4-carboxylate (prepared as described above) (0.28 g, 0.925 mmol) in methanol (4.2 mL) under nitrogen was added a drop of trifluoroacetic acid, followed by diacetoxyiodobenzene (0.36 g, 1.11 mmol), cyclopropanecarbaldehyde oxime (0.105 g, 1.11 mmol) and one drop of trifluoroacetic acid. The reaction mixture was stirred at room temperature for 12 hours, then concentrated in vacuo. The crude was purified by combiflash (silica gel, ethyl acetate in cyclohexane) to afford ethyl 2-(3-cyclopropyl-4,5-dihydroisoxazol-5-yl)-5-ethylsulfonyl-1-methyl-imidazole-4-carboxylate. LCMS (method 1): Rt=0.99 min, m/z=356 (M+H)+. $^{1}$H NMR (400 MHz, $CDCl_3$) δ ppm: 5.61 (dd, J=10.67, 7.65 Hz, 1H) 4.43 (qd, J=7.15, 1.63 Hz, 2H) 4.03 (s, 3H) 3.88-3.97 (m, 1H) 3.54-3.69 (m, 2H) 3.16 (dd, J=16.81, 10.79 Hz, 1H) 1.82-1.89 (m, 1H) 1.42 (br t, J=7.15 Hz, 3H) 1.39 (br t, J=7.40 Hz, 3H) 0.84-1.02 (m, 4H).

Step B3: Preparation of 2-(3-cyclopropyl-4,5-dihydroisoxazol-5-yl)-5-ethylsulfonyl-1-methyl-imidazole-4-carboxylic Acid (Intermediate I-15)

(I-15)

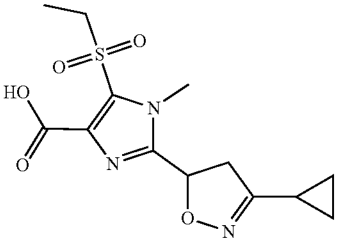

To a solution of ethyl 2-(3-cyclopropyl-4,5-dihydroisoxazol-5-yl)-5-ethylsulfonyl-1-methyl-imidazole-4-carboxylate (prepared as described above) (2.4 g, 6.4 mmol) in tetrahydrofuran (10 mL) was added a solution of lithium hydroxide monohydrate (0.71 g, 16 mmol) in water (2 mL) at 0° C. The reaction mixture was stirred at room temperature for 12 hours. After completion, the reaction mixture was concentrated in vacuo, the residue acidified with a 1N aqueous hydrochloric acid solution and poured into ethyl acetate. The organic layer was separated, washed twice with water, then once with brine, dried over anhydrous sodium sulfate, filtered and concentrated in vacuo to afford 2-(3-cyclopropyl-4,5-dihydroisoxazol-5-yl)-5-ethylsulfonyl-1-methyl-imidazole-4-carboxylic acid. This material was used as such in the next step. LCMS (method 1): Rt=0.15 min, m/z=328 $(M+H)^+$.

Step B4: Preparation of tert-butyl N-[2-(3-cyclopropyl-4,5-dihydroisoxazol-5-yl)-5-ethylsulfonyl-1-methyl-imidazol-4-yl]carbamate (Intermediate I-16)

(I-16)

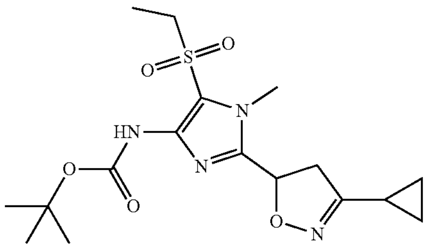

To a solution of 2-(3-cyclopropyl-4,5-dihydroisoxazol-5-yl)-5-ethylsulfonyl-1-methyl-imidazole-4-carboxylic acid (intermediate I-15 prepared as described above) (2.20 g, 6.4 mmol) in tert-butanol (33 mL) was added triethylamine (1.0 g, 10 mmol) at room temperature. The mixture was heated to 90° C. and stirred for 10 minutes. Diphenylphosphoryl azide (1.19 mL, 5.43 mmol) was added dropwise over a period of 10 minutes and the resulting reaction mixture was stirred at 90° C. for 60 minutes. The reaction mass was allowed to cool to room temperature, then quenched with ice cold water (100 mL) and the product extracted with ethyl acetate. The combined organic layers were washed twice with water, once with brine, dried over sodium sulfate, filtered and concentrated in vacuo. The crude was purified by combiflash (silica gel, 20-70% ethyl acetate in cyclohexane) to afford tert-butyl N-[2-(3-cyclopropyl-4,5-dihydroisoxazol-5-yl)-5-ethylsulfonyl-1-methyl-imidazol-4-yl] carbamate. LCMS (method 1): Rt=1.09 min, m/z=343 [M+H−56]*. $^{1}$H NMR (400 MHz, $CDCl_3$) δ ppm: 0.84-1.01 (m, 4H) 1.26-1.40 (m, 3H) 1.52 (s, 9H) 1.80-1.87 (m, 1H) 3.13-3.24 (m, 3H) 3.81-3.87 (m, 1H) 3.88 (s, 2H) 4.14 (d, J=7.09 Hz, 1H) 5.58 (dd, J=10.76, 8.31 Hz, 1H) 7.77 (s, 1H).

Step C1: Preparation of ethyl 2-[[tert-butoxycarbonyl-[2-(3-cyclopropyl-4,5-dihydroisoxazol-5-yl)-5-ethylsulfonyl-1-methyl-imidazol-4-yl]amino] methyl]-5-(trifluoromethyl)pyridine-3-carboxylate

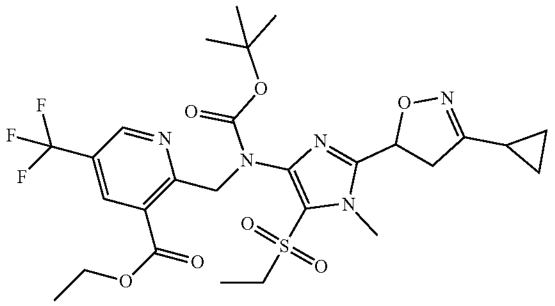 [SMILES: CCOC(=O)c1cc(C(F)(F)F)cnc1CN(C(=O)OC(C)(C)C)c1nc(C2CC(C3CC3)=NO2)n(C)c1S(=O)(=O)CC]

To a stirred solution of tert-butyl N-[2-(3-cyclopropyl-4,5-dihydroisoxazol-5-yl)-5-ethylsulfonyl-1-methyl-imidazol-4-yl]carbamate (intermediate I-16 prepared as described above) (0.80 g, 1.91 mmol) in acetonitrile (20 mL) were added ethyl 2-(bromomethyl)-5-(trifluoromethyl)pyridine-3-carboxylate (intermediate I-4 prepared as described in example P3 step A3) (0.41 g, 1.31 mmol) and cesium carbonate (0.50 g, 1.52 mmol) at room temperature. The reaction mixture was stirred at 50° C. for 4 hours, then quenched with ice cold water (50 mL) and the product extracted with ethyl acetate (3×50 mL). The combined organic layers were dried over sodium sulfate, filtered and concentrated in vacuo. The crude was purified by combiflash (silica gel, 55% ethyl acetate in cyclohexane) to afford methyl 2-[[tert-butoxycarbonyl-[2-(1-cyclopropylpyrazol-4-yl)-5-ethylsulfonyl-1-methyl-imidazol-4-yl]amino]methyl]-5-(trifluoromethoxy)benzoate as a gummy mass. LCMS (method 2): Rt=1.62 min, m/z=328 $(M+H)^+$.

Step C2: Preparation of ethyl 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylate

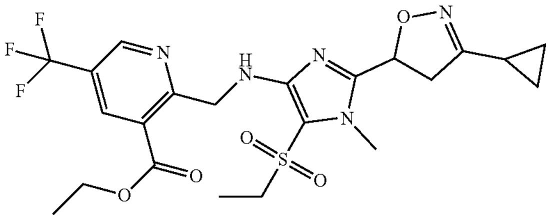 [SMILES: CCOC(=O)c1cc(C(F)(F)F)cnc1CNc1nc(C2CC(C3CC3)=NO2)n(C)c1S(=O)(=O)CC]

A solution of ethyl 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylate (intermediate I-15 prepared as described above) (1.5 g, 1.9 mmol) in trifluoro acetic acid (5 mL) was stirred for 12 hours. Then the reaction mass was neutralized with saturated aqueous sodium bicarbonate solution. The aqueous layer was extracted twice with ethyl acetate. The combined organic layers were dried over sodium sulfate, filtered and concentrated in vacuo to afford ethyl 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylate. This material was used as such in the next step. LCMS (method 1): Rt=1.16 min, m/z=530 $(M+H)^+$.

Step C3: Preparation of 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylic Acid

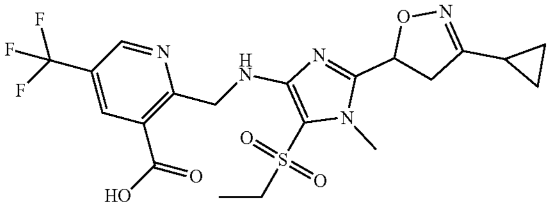 [SMILES: CCS(=O)(=O)c1c(NCc2ncc(C(F)(F)F)cc2C(=O)O)nc(C2CC(C3CC3)=NO2)n1C]

To a solution of ethyl 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylate (prepared as described above) (0.83 g, 1.49 mmol) in tetrahydrofuran (10 mL) was added a solution of lithium hydroxide monohydrate (0.16 g, 3.72 mmol) in water (2 mL) at 0° C. The reaction mixture was stirred at room temperature for 12 hours. After completion, the reaction mixture was concentrated in vacuo, the residue acidified with an aqueous 1N hydrochloric acid solution and the product extracted with ethyl acetate. The organic layers were washed twice with water, once with brine, dried over sodium sulfate, filtered and concentrated in vacuo to afford 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylic acid. This material was used as such in the next step. LCMS (method 1): Rt=1.04 min, m/z=502 $(M+H)^+$.

Step C4: Preparation of 6-[2-(3-cyclopropyl-4,5-dihydroisoxazol-5-yl)-5-ethylsulfonyl-1-methyl-imidazol-4-yl]-3-(trifluoromethyl)-7H-pyrrolo[3,4-b]pyridin-5-one (P3)

(P3)

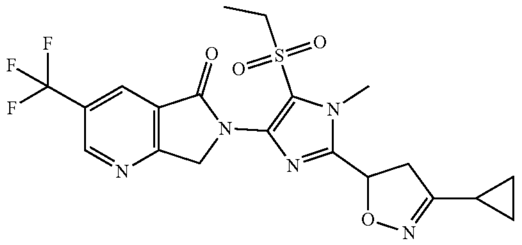

To a 0° C. cooled solution of 2-[[[2-(3-cyclopropyl-4,5-dihydroisoxazol-5-yl)-5-ethylsulfonyl-1-methyl-imidazol-4-yl]amino]methyl]-5-(trifluoromethyl)pyridine-3-carboxylic acid (prepared as described above) (0.78 g, 1.48 mmol) in pyridine (5 mL) was added phosphorus oxychloride (0.28 mL, 2.95 mmol) dropwise under nitrogen. The reaction mixture was allowed to reach room temperature and was stirred for 2 hours. The reaction mass was acidified with an aqueous 1N hydrochloric acid (30 mL) solution and the product extracted with ethyl acetate (2×30 mL). The combined organic layers were dried over sodium sulfate, filtered and concentrated in vacuo. The crude was purified by combiflash (silica gel, 50% ethyl acetate in cyclohexane) to afford pure compound 6-[2-(3-cyclopropyl-4,5-dihydroisoxazol-5-yl)-5-ethylsulfonyl-1-methyl-imidazol-4-yl]-3-(trifluoromethyl)-7H-pyrrolo[3,4-b]pyridin-5-one (compound P3) as a solid. LCMS (method 2): Rt=1.35 min, m/z=484 (M+H)+. $^1H$ NMR (400 MHz, DMSO-d6) δ ppm 9.30 (d, J=1.38 Hz, 1H) 8.67 (d, J=1.63 Hz, 1H) 5.85 (dd, J=10.82, 7.07 Hz, 1H) 5.02 (d, J=4.38 Hz, 2H) 3.91 (s, 3H) 3.49-3.67 (m, 3H) 3.21-3.30 (m, 1H) 1.82-1.89 (m, 1H) 1.27 (t, J=7.38 Hz, 3H) 0.79-0.94 (m, 4H).

Example P6: Preparation of 6-[5-ethylsulfonyl-1-methyl-2-(2,2,2-trifluoroethoxy)imidazol-4-yl]-3-(trifluoromethyl)-7H-pyrrolo[3,4-b]pyridin-5-one (Compound P6)

(P6)

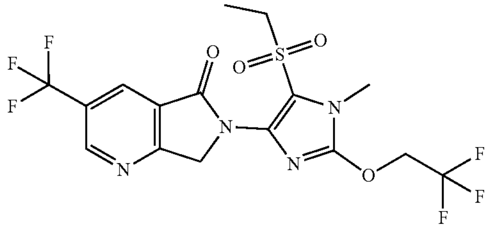

Step A1: Preparation of ethyl 5-ethylsulfonyl-1-methyl-2-(2,2,2-trifluoroethoxy)imidazole-4-carboxylate

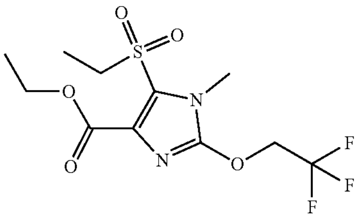 [SMILES: CCOC(=O)c1nc(OCC(F)(F)F)n(C)c1S(=O)(=O)CC]

To a solution of 2,2,2-trifluoroethanol (7.8 g, 77 mmol) and ethyl 2-bromo-5-ethylsulfonyl-1-methyl-imidazole-4-carboxylate (intermediate I-8 prepared as described in example P1 step B4) (5.0 g, 15 mmol) in pyridine (50 mL) were added potassium carbonate (6.4 g, 46 mmol) and cuprous iodide (0.44 g, 2.3 mmol) at 0° C. The reaction mixture was stirred at 16° C. for 16 hours. Then, the reaction mass was poured in ice cold water and stirred for 5 minutes. The aqueous layer was extracted with ethyl acetate (2×100 mL), the combined organic layers washed with water, then with brine, dried over sodium sulfate, filtered and concentrated in vacuo. The residue was triturated with n-pentane, filtered and dried in vacuo to afford ethyl 5-ethylsulfonyl-1-methyl-2-(2,2,2-trifluoroethoxy)imidazole-4-carboxylate. The crude material was used as such in the next step. LCMS (method 1): Rt=1.33 min, m/z=345 (M+H)+.

Step A2: Preparation of 5-ethylsulfonyl-1-methyl-2-(2,2,2-trifluoroethoxy)imidazole-4-carboxylic acid (Intermediate I-21)

(I-21)

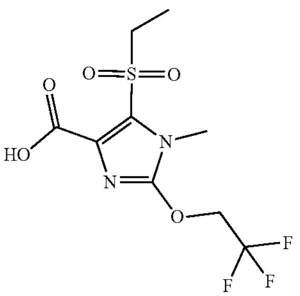

To a solution of ethyl 5-ethylsulfonyl-1-methyl-2-(2,2,2-trifluoroethoxy)imidazole-4-carboxylate (prepared as described above) (2.0 g, 5.8 mmol) in tetrahydrofuran (20 mL) was added a solution of lithium hydroxide monohydrate (0.73 g, 17 mmol) in water (2 mL) at 0° C. The reaction mixture was stirred at room temperature for 3 hours. After completion, the reaction mixture was acidified with a 2N aqueous hydrochloric acid solution and diluted with water. The aqueous layer was extracted three times with ethyl acetate. The combined organic layers were washed with brine, dried over sodium sulfate, filtered and concentrated in vacuo to afford 5-ethylsulfonyl-1-methyl-2-(2,2,2-trifluoroethoxy)imidazole-4-carboxylic acid. This material was used as such in the next step. LCMS (method 1): Rt=0.95 min, m/z=317 $(M+H)^+$.

Step A3: Preparation of tert-butyl N-[5-ethylsulfonyl-1-methyl-2-(2,2,2-trifluoroethoxy)imidazol-4-yl] carbamate (Intermediate I-22)

(I-22)

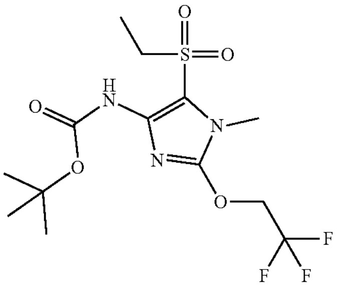

To a solution of 5-ethylsulfonyl-1-methyl-2-(2,2,2-trifluoroethoxy)imidazole-4-carboxylic acid (intermediate I-21 prepared as described above) (0.40 g, 1 mmol) in tert-butanol (8 mL) was added triethylamine (0.2 g, 2 mmol) at room temperature. The mixture was heated to 90° C. and stirred for 10 minutes. Diphenylphosphoryl azide (0.4 mL, 2 mmol) was added dropwise over a period of 15 minutes and the resulting reaction mixture was stirred at 90° C. for 40 minutes. The reaction mass was allowed to cool to room temperature, quenched with ice cold water (100 mL) and brine (40 mL), and the product extracted with ethyl acetate (3×100 mL). The combined organic layers were dried over sodium sulfate, filtered and concentrated in vacuo. The crude was purified by combiflash (silica gel, 40% ethyl acetate in cyclohexane) to afford tert-butyl N-[5-ethylsulfonyl-1-methyl-2-(2,2,2-trifluoroethoxy)imidazol-4-yl]carbamate. LCMS (method 1): Rt=1.10 min, m/z=288 $[M+H-100]^+$. $^1H$ NMR (400 MHz, $CDCl_3$) δ ppm 1.26-1.44 (m, 3H) 1.61 (s, 9H) 3.17 (q, J=7.46 Hz, 2H) 3.59 (s, 3H) 4.89 (q, J=8.07 Hz, 2H) 7.85 (s, 1H).

Step B1: Preparation of ethyl 2-[[tert-butoxycarbonyl-[5-ethylsulfonyl-1-methyl-2-(2,2,2-trifluoroethoxy)imidazol-4-yl]amino]methyl]-5-(trifluoromethyl)pyridine-3-carboxylate

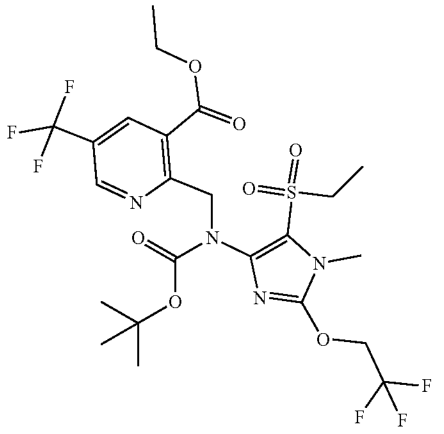 [SMILES: CCOC(=O)c1cc(C(F)(F)F)cnc1CN(C(=O)OC(C)(C)C)c1nc(OCC(F)(F)F)n(C)c1S(=O)(=O)CC]

To a stirred solution of tert-butyl N-[5-ethylsulfonyl-1-methyl-2-(2,2,2-trifluoroethoxy)imidazol-4-yl]carbamate (intermediate I-22 prepared as described above) (0.60 g, 2 mmol) in acetonitrile (10 mL) were added ethyl 2-(bromomethyl)-5-(trifluoromethyl)pyridine-3-carboxylate (intermediate I-4 prepared as described in example P3 step A3) (0.60 g, 2 mmol) and cesium carbonate (0.80 g, 2 mmol) at room temperature. The reaction mixture was stirred at 50° C. for 24 hours, then quenched with ice cold water (30 mL) and the product extracted with ethyl acetate (3×50 mL). The combined organic layers were washed with brine, dried over sodium sulfate, filtered and concentrated in vacuo. The crude was purified by combiflash (silica gel, 30% ethyl acetate in cyclohexane) to afford ethyl 2-[[tert-butoxycarbonyl-[5-ethylsulfonyl-1-methyl-2-(2,2,2-trifluoroethoxy)imidazol-4-yl]amino]methyl]-5-(trifluoromethyl)pyridine-3-carboxylate. LCMS (method 1): Rt=1.24 min, m/z=619 $(M+H)^+$.

Step B2: Preparation of ethyl 2-[[[5-ethylsulfonyl-1-methyl-2-(2,2,2-trifluoroethoxy)imidazol-4-yl]amino]methyl]-5-(trifluoromethyl)pyridine-3-carboxylate

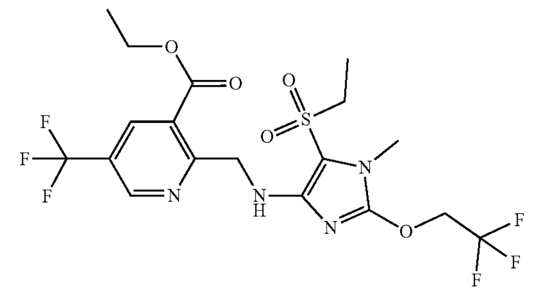 [SMILES: CCOC(=O)c1cc(C(F)(F)F)cnc1CNc1nc(OCC(F)(F)F)n(C)c1S(=O)(=O)CC]

A solution of ethyl 2-[[tert-butoxycarbonyl-[5-ethylsulfonyl-1-methyl-2-(2,2,2-trifluoroethoxy)imidazol-4-yl]amino]methyl]-5-(trifluoromethyl)pyridine-3-carboxylate (prepared as described above) (0.60 g, 1 mmol) in trifluoromethylbenzene (10 mL) was added trifluoro acetic acid (1 mL). The reaction mass was stirred for 12 hours, then concentrated in vacuo. Water (50 mL) was added and the solution was neutralized with a saturated aqueous sodium bicarbonate solution (30 mL). The aqueous layer was extracted with ethyl acetate (2×50 mL). The combined organic layers were dried over sodium sulfate, filtered and concentrated in vacuo to afford ethyl 2-[[[5-ethylsulfonyl-1-methyl-2-(2,2,2-trifluoroethoxy)imidazol-4-yl]amino]methyl]-5-(trifluoromethyl)pyridine-3-carboxylate as a solid. This material was used as such in the next step. LCMS (method 2): Rt=1.55 min, m/z=519 $(M+H)^+$.

Step B3: Preparation of 2-[[[5-ethylsulfonyl-1-methyl-2-(2,2,2-trifluoroethoxy)imidazol-4-yl]amino]methyl]-5-(trifluoromethyl)pyridine-3-carboxylic Acid

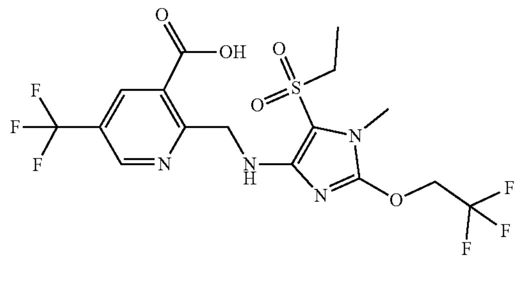 [SMILES: CCS(=O)(=O)c1c(NCc2ncc(C(F)(F)F)cc2C(=O)O)nc(OCC(F)(F)F)n1C]

To a solution of ethyl 2-[[[5-ethylsulfonyl-1-methyl-2-(2,2,2-trifluoroethoxy)imidazol-4-yl]amino]methyl]-5-(trifluoromethyl)pyridine-3-carboxylate (prepared as described above) (0.120 g, 0.231 mmol) in tetrahydrofuran (5 mL) was added a solution of lithium hydroxide monohydrate (0.051 g, 1.16 mmol) in water (0.5 mL) at room temperature. The reaction mixture was stirred at room temperature overnight. After completion, the reaction mixture was concentrated in vacuo, the residue acidified with an aqueous 1N hydrochloric acid solution and the product extracted twice with ethyl acetate (2×50 mL). The combined organic layers were washed with water, then with brine, dried over sodium sulfate, filtered and concentrated in vacuo to afford 2-[[[5-ethylsulfonyl-1-methyl-2-(2,2,2-trifluoroethoxy)imidazol-4-yl]amino]methyl]-5-(trifluoromethyl)pyridine-3-carboxylic acid. This material was used as such in the next step. LCMS (method 1): Rt=1.10 min, m/z=491 $(M+H)^+$.

Step B4: Preparation of 6-[5-ethylsulfonyl-1-methyl-2-(2,2,2-trifluoroethoxy)imidazol-4-yl]-3-(trifluoromethyl)-7H-pyrrolo[3,4-b]pyridin-5-one (P6)

(P6)

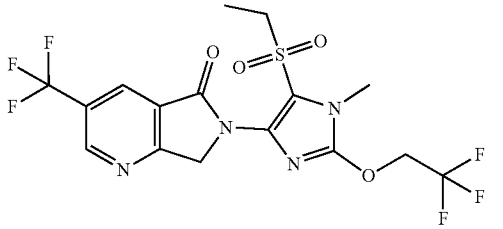

To a 0° C. cooled solution of 2-[[[5-ethylsulfonyl-1-methyl-2-(2,2,2-trifluoroethoxy)imidazol-4-yl]amino]methyl]-5-(trifluoromethyl)pyridine-3-carboxylic acid (prepared as described above) (0.100 g, 0.204 mmol) in pyridine (1 mL) was added phosphorus oxychloride (0.038 mL, 0.408 mmol) dropwise under nitrogen. The reaction mixture was stirred at that temperature for 1 hour. The reaction mass was poured in ice cold water (30 mL), acidified with aqueous 1N hydrochloric acid (30 mL), and the product extracted with ethyl acetate (2×30 mL). The combined organic layers were washed with brine, dried over sodium sulfate, filtered and concentrated in vacuo. The crude was purified by combiflash (silica gel, 30-100% ethyl acetate in cyclohexane) to afford pure compound 6-[5-ethylsulfonyl-1-methyl-2-(2,2,2-trifluoroethoxy)imidazol-4-yl]-3-(trifluoromethyl)-7H-pyrrolo[3,4-b]pyridin-5-one (compound P6) as a tan solid. LCMS (method 2): Rt=1.41 min, m/z=473 (M+H)+. $^1$H NMR (400 MHz, DMSO-d6) δ ppm 1.08-1.50 (m, 3H) 3.52-3.55 (m, 2H) 3.57 (s, 3H) 4.93 (s, 2H) 5.08 (q, J=8.67 Hz, 2H) 8.61 (d, J=1.50 Hz, 1H) 9.23 (s, 1H).

Example P16: Preparation of 6-[2-(3-chloropyrazol-1-yl)-5-ethylsulfonyl-1-methyl-imidazol-4-yl]-3-(trifluoromethyl)-7H-pyrrolo[3,4-b]pyridin-5-one (Compound P16)

(P16)

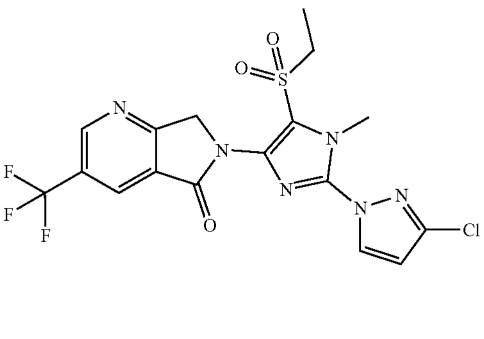

Step A1: Preparation of ethyl 2-(3-chloropyrazol-1-yl)-5-ethylsulfonyl-1-methyl-imidazole-4-carboxylate

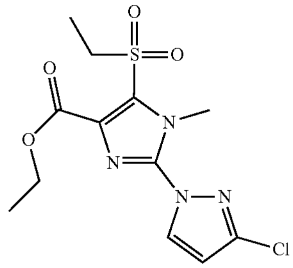 [SMILES: CCOC(=O)c1nc(-n2ccc(Cl)n2)n(C)c1S(=O)(=O)CC]

To a solution of ethyl 2-bromo-5-ethylsulfonyl-1-methyl-imidazole-4-carboxylate (intermediate I-9 prepared as described in example P1 step B4) (10.0 g, 30.8 mmol) and 3-chloro-1H-pyrazole (3.47 g, 33.8 mmol) in N,N-dimethylformamide (100 mL) were added N,N'-dimethylethane-1,2-diamine (0.542 g, 6.15 mmol), potassium carbonate (1.70 g, 12.3 mmol), followed by copper iodide (0.586 g, 3.08 mmol) at room temperature. The reaction mass was stirred at 120° C. for 16 hours. Then, water was added and the aqueous layer was extracted with ethyl acetate (3×100 mL). The combined organic layers were washed with water, dried over sodium sulfated and concentrated in vacuo. The crude was purified by combiflash (silica gel, 0-25% ethyl acetate in cyclohexane) to afford ethyl 2-(3-chloropyrazol-1-yl)-5-ethylsulfonyl-1-methyl-imidazole-4-carboxylate as a yellowish semi-solid. LCMS (method 1): Rt=1.09 min, m/z=347 (M+H)+. $^1$H NMR (400 MHz, $CDCl_3$) δ ppm 1.43 (td, J=7.31, 2.02 Hz, 6H) 3.67 (q, J=7.46 Hz, 2H) 4.11-4.17 (m, 3H) 4.46 (q, J=7.13 Hz, 2H) 6.47 (d, J=2.69 Hz, 1H) 8.12 (d, J=2.69 Hz, 1H).

Step A2: Preparation of 2-(3-chloropyrazol-1-yl)-5-ethylsulfonyl-1-methyl-imidazole-4-carboxylic Acid (Intermediate I-37)

(I-37)

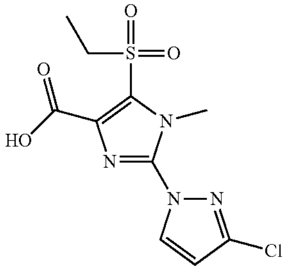

To a solution of ethyl 2-(3-chloropyrazol-1-yl)-5-ethylsulfonyl-1-methyl-imidazole-4-carboxylate (prepared as described above) (4.90 g, 14.1 mmol) in tetrahydrofuran (73.5 mL) was added a solution of lithium hydroxide monohydrate (0.889 g, 21 mmol) in water (19.6 mL) at room temperature. The reaction mixture was stirred at room temperature for 16 hours. After completion, the reaction mixture was quenched with water (100 mL), acidified with 2N aqueous hydrochloric acid (20 mL) and the product extracted with ethyl acetate (3×100 mL). The combined organic layers were washed with brine, dried over sodium sulfate, filtered and concentrated in vacuo. The crude material was washed twice with n-pentane and dried to afford 2-(3-cyclopropyl-4,5-dihydroisoxazol-5-yl)-5-ethylsulfonyl-1-methyl-imidazole-4-carboxylic acid as a white solid. This material was used as such in the next step. LCMS (method 1): Rt=0.92 min, m/z=319 $(M+H)^+$. $^1H$ NMR (400 MHz, DMSO-d6) δ ppm 1.28 (t, J=7.40 Hz, 3H) 3.67 (q, J=7.34 Hz, 2H) 3.83 (s, 3H) 6.80 (d, J=2.69 Hz, 1H) 8.41 (d, J=2.57 Hz, 1H) 13.27-14.12 (m, 1H).

Step A3: Preparation of tert-butyl N-[2-(3-chloropyrazol-1-yl)-5-ethylsulfonyl-1-methyl-imidazol-4-yl]carbamate (Intermediate I-36)

(I-36)

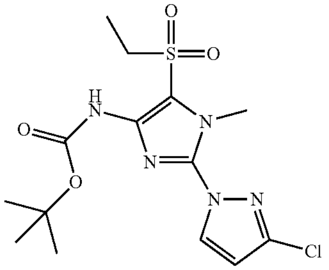

To a solution of 2-(3-chloropyrazol-1-yl)-5-ethylsulfonyl-1-methyl-imidazole-4-carboxylic acid (intermediate I-37 prepared as described above) (4.10 g, 12.9 mmol) in tert-butanol (82 mL) was added triethylamine (2.10 g, 20.6 mmol) at room temperature. The mixture was heated to 90° C. and stirred for 10 minutes. Diphenylphosphoryl azide (4.53 mL, 20.6 mmol) was added dropwise over a period of 15 minutes and the resulting reaction mixture was stirred at 90° C. for 40 minutes. The reaction mass was allowed to cool to room temperature, quenched with ice cold water (100 mL) and brine (40 mL), and the product extracted with ethyl acetate (3×100 mL). The combined organic layers were dried over sodium sulfate, filtered and concentrated in vacuo. The crude was purified by combiflash (silica gel, 40% ethyl acetate in cyclohexane) to afford tert-butyl N-[2-(3-chloropyrazol-1-yl)-5-ethylsulfonyl-1-methyl-imidazol-4-yl]carbamate. LCMS (method 2): Rt=1.37 min, m/z=388 $(M-H)^-$. $^1H$ NMR (400 MHz, $CDCl_3$) δ ppm 1.37 (t, J=7.40 Hz, 3H) 1.56 (s, 9H) 3.22 (d, J=7.46 Hz, 2H) 4.04 (s, 3H) 6.41 (d, J=2.81 Hz, 1H) 8.23 (d, J=2.69 Hz, 1H).

Step B1: Preparation of ethyl 2-[[tert-butoxycarbonyl-[2-(3-chloropyrazol-1-yl)-5-ethylsulfonyl-1-methyl-imidazol-4-yl]amino]methyl]-5-(trifluoromethyl)pyridine-3-carboxylate

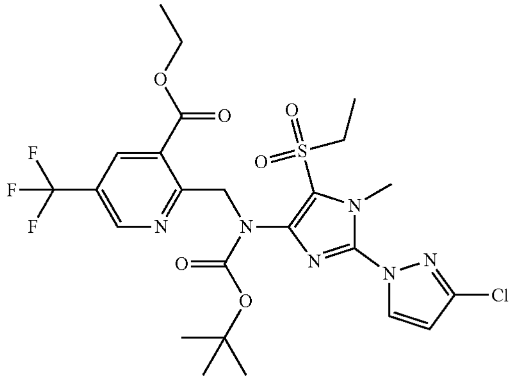 [SMILES: CCOC(=O)c1cc(C(F)(F)F)cnc1CN(C(=O)OC(C)(C)C)c1nc(-n2ccc(Cl)n2)n(C)c1S(=O)(=O)CC]

To a stirred solution of tert-butyl N-[2-(3-chloropyrazol-1-yl)-5-ethylsulfonyl-1-methyl-imidazol-4-yl]carbamate (intermediate I-36 prepared as described above) (1.00 g, 2.56 mmol) in acetonitrile (20 mL) were added ethyl 2-(bromomethyl)-5-(trifluoromethyl)pyridine-3-carboxylate (intermediate I-4 prepared as described in example P3 step A3) (1.04 g, 3.33 mmol) and cesium carbonate (1.25 g, 3.85 mmol) at room temperature. The reaction mixture was stirred at 50° C. for 9 hours, then quenched with ice cold water (30 mL) and the product extracted with ethyl acetate (3×50 mL). The combined organic layers were washed with brine (20 mL), dried over sodium sulfate, filtered and concentrated in vacuo to afford ethyl 2-[[tert-butoxycarbonyl-[2-(3-chloropyrazol-1-yl)-5-ethylsulfonyl-1-methyl-imidazol-4-yl]amino]methyl]-5-(trifluoromethyl)pyridine-3-carboxylate. This material was used as such in the next step.

Step B2: Preparation of ethyl 2-[[[2-(3-chloropyrazol-1-yl)-5-ethylsulfonyl-1-methyl-imidazol-4-yl]amino]methyl]-5-(trifluoromethyl)pyridine-3-carboxylate

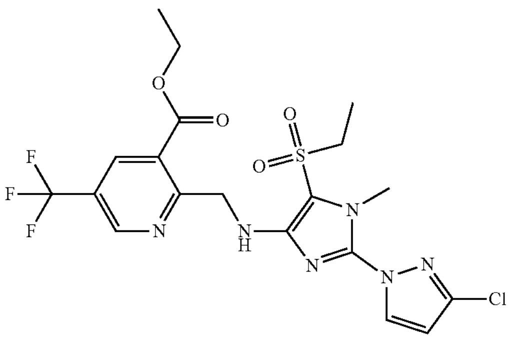 [SMILES: CCOC(=O)c1cc(C(F)(F)F)cnc1CNc1nc(-n2ccc(Cl)n2)n(C)c1S(=O)(=O)CC]

A solution of ethyl 2-[[tert-butoxycarbonyl-[2-(3-chloropyrazol-1-yl)-5-ethylsulfonyl-1-methyl-imidazol-4-yl]amino]methyl]-5-(trifluoromethyl)pyridine-3-carboxylate (prepared as described above) (2.10 g, 3.38 mmol) in trifluoromethylbenzene (42 mL) was added trifluoro acetic acid (3.88 mL, 50.7 mmol) at 0° C. The reaction mass was stirred at room temperature for 3 hours, then trifluoro acetic acid (1.29 mL, 16.9 mmol) was added and the mixture was stirred for 16 hours. After completion, the reaction mixture was concentrated in vacuo. Water (20 mL) was added to the residue and the solution was neutralized with a saturated aqueous sodium bicarbonate solution (30 mL). The aqueous layer was extracted with ethyl acetate (3×50 mL). The combined organic layers were washed with brine (50 mL), dried over sodium sulfate, filtered and concentrated in vacuo. The crude was purified by combiflash (silica gel, 40% ethyl acetate in cyclohexane) to afford ethyl 2-[[[2-(3-chloropyrazol-1-yl)-5-ethylsulfonyl-1-methyl-imidazol-4-yl]amino]methyl]-5-(trifluoromethyl)pyridine-3-carboxylate as a semi-solid. LCMS (method 2): Rt=1.51 min, m/z=521 $(M+H)^+$. $^1$H NMR (400 MHz, $CDCl_3$) δ ppm 1.28-1.39 (m, 3H) 1.46 (t, J=7.15 Hz, 3H) 3.18 (q, J=7.46 Hz, 2H) 3.94 (s, 3H) 4.47 (q, J=7.09 Hz, 2H) 5.11 (s, 2H) 6.40 (d, J=2.69 Hz, 1H) 6.75 (br s, 1H) 8.06 (d, J=2.69 Hz, 1H) 8.47 (d, J=1.96 Hz, 1H) 8.96 (d, J=1.47 Hz, 1H).

Step B3: Preparation of 2-[[[2-(3-chloropyrazol-1-yl)-5-ethylsulfonyl-1-methyl-imidazol-4-yl]amino]methyl]-5-(trifluoromethyl)pyridine-3-carboxylic Acid

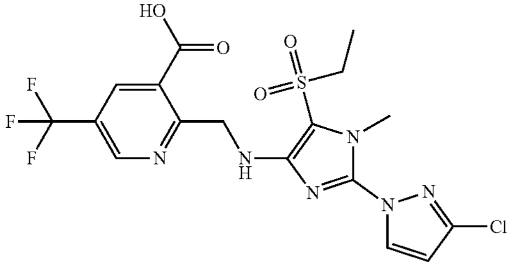 [SMILES: CCS(=O)(=O)c1c(NCc2ncc(C(F)(F)F)cc2C(=O)O)nc(-n2ccc(Cl)n2)n1C]

To a solution of 2-[[[2-(3-chloropyrazol-1-yl)-5-ethylsulfonyl-1-methyl-imidazol-4-yl]amino]methyl]-5-(trifluoromethyl)pyridine-3-carboxylic acid (prepared as described above) (1.00 g, 1.92 mmol) in tetrahydrofuran (15 mL) was added a solution of lithium hydroxide monohydrate (0.16 g, 3.84 mmol) in water (4 mL) at room temperature. The reaction mixture was stirred at room temperature for 5 hours. After completion, the reaction mixture was quenched with water (20 mL), acidified with an aqueous 2N hydrochloric acid (10 mL) solution, and the product extracted with ethyl acetate (3×50 mL). The combined organic layers were washed with brine, dried over sodium sulfate, filtered and concentrated in vacuo to afford 2-[[[2-(3-chloropyrazol-1-yl)-5-ethylsulfonyl-1-methyl-imidazol-4-yl]amino]methyl]-5-(trifluoromethyl)pyridine-3-carboxylic acid as a white solid. This material was used as such in the next step. LCMS (method 1): Rt=1.41 min, m/z=493 $(M+H)^+$. $^1$H NMR (400 MHz, DMSO-d6) δ ppm 1.17 (t, J=7.27 Hz, 3H) 3.24-3.41 (m, 2H) 3.69 (s, 3H) 5.02 (br d, J=5.01 Hz, 2H) 6.65-6.70 (m, 1H) 6.73 (d, J=2.69 Hz, 1H) 8.29 (d, J=2.69 Hz, 1H) 8.49 (d, J=1.96 Hz, 1H) 9.11 (d, J=1.34 Hz, 1H) 13.39-14.75 (m, 1H).

Step B4: Preparation of 6-[2-(3-chloropyrazol-1-yl)-5-ethylsulfonyl-1-methyl-imidazol-4-yl]-3-(trifluoromethyl)-7H-pyrrolo[3,4-b]pyridin-5-one (P16)

(P16)

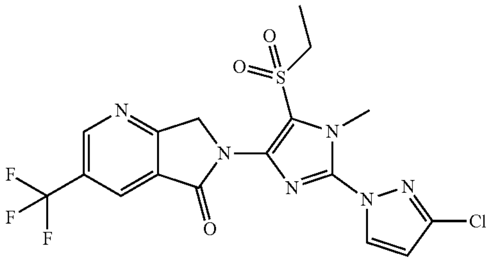

To a 0° C. cooled solution of 2-[[[2-(3-chloropyrazol-1-yl)-5-ethylsulfonyl-1-methyl-imidazol-4-yl]amino]methyl]-5-(trifluoromethyl)pyridine-3-carboxylic acid (prepared as described above) (0.860 g, 0.948 mmol) in pyridine (8.6 mL) was added phosphorus oxychloride (0.328 mL, 3.49 mmol) dropwise under nitrogen. The reaction mixture was stirred at that temperature for 45 minutes, then poured in ice cold water (30 mL) and the product extracted with ethyl acetate (2×50 mL). The combined organic layers were washed with brine (30 mL), dried over sodium sulfate, filtered and concentrated in vacuo. The crude was purified by combiflash (silica gel, 70-80% ethyl acetate in cyclohexane) to afford pure compound 6-[2-(3-chloropyrazol-1-yl)-5-ethylsulfonyl-1-methyl-imidazol-4-yl]-3-(trifluoromethyl)-7H-pyrrolo[3,4-b]pyridin-5-one (compound P16) as a yellow solid. LCMS (method 1): Rt=1.07 min, m/z=475 (M+H)+. $^1$H NMR (400 MHz, $CDCl_3$) δ ppm 1.41-1.58 (m, 3H) 3.62 (q, J=7.46 Hz, 2H) 4.17 (s, 3H) 5.04 (s, 2H) 6.48 (d, J=2.69 Hz, 1H) 8.09 (d, J=2.69 Hz, 1H) 8.44 (s, 1H) 9.10 (s, 1H).

TABLE P

| Examples of compounds of formula (I) | | | | | | |
|---|---|---|---|---|---|---|
| | | | LCMS | | | |
| No. | IUPAC name | Structures | $R_t$ (min) | $[M + H]^+$ (measured) | Method | Mp (° C) |
| P1 | 2-[2-(1-cyclopropylpyrazol-4yl)-5-ethylsulfonyl-1-methyl-imidazol-4-yl]-6-(trifluoromethoxy) isoindolin-1-one- | 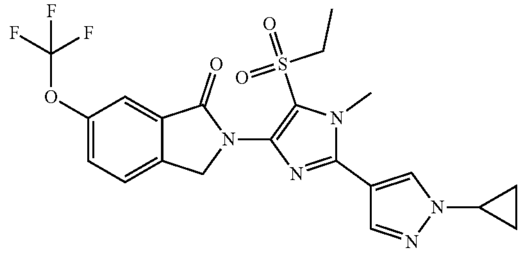 [SMILES: CCS(=O)(=O)c1c(N2Cc3ccc(OC(F)(F)F)cc3C2=O)nc(-c2cnn(C3CC3)c2)n1C] | 1.44 | 496 | 2 | 98-100 |
| P2 | 6-[2-(1-cyclopropylpyrazol-4-yl)-5-ethylsulfonyl-1-methyl-imidazol-4-yl]-3-(trifluoromethyl)-7H-pyrrolo[3,4-b]pyridin-5-one | 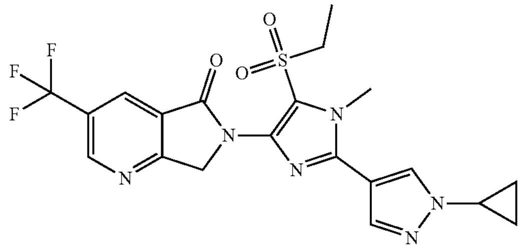 [SMILES: CCS(=O)(=O)c1c(N2Cc3ncc(C(F)(F)F)cc3C2=O)nc(-c2cnn(C3CC3)c2)n1C] | 1.00 | 481 | 1 | 196-198 |
| P3 | 6-[2-(3-cyclopropyl-4,5-dihydroisoxazol-5-yl)-5-ethylsulfonyl-1-methyl-imidazol-4-yl]-3-(trifluoromethyl)-7H-pyrrolo[3,4-b]pyridin-5-one | 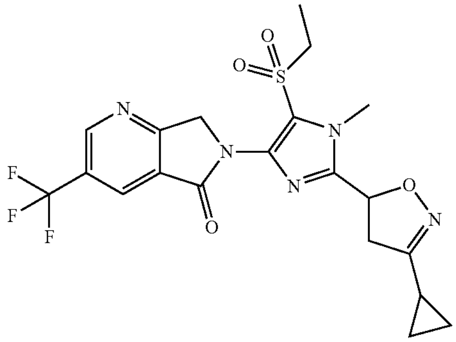 [SMILES: CCS(=O)(=O)c1c(N2Cc3ncc(C(F)(F)F)cc3C2=O)nc(C2CC(C3CC3)=NO2)n1C] | 1.35 | 484 | 2 | 239-243 |
| P4 | 1-[[4-[5-ethylsulfonyl-1-methyl-4-[5-oxo-3-(trifluoromethyl)-7H-pyrrolo[3,4-b]pyridin-6-yl]imidazol-2-yl]pyrazol-1-yl]methyl] cyclopropane-carbonitrile | 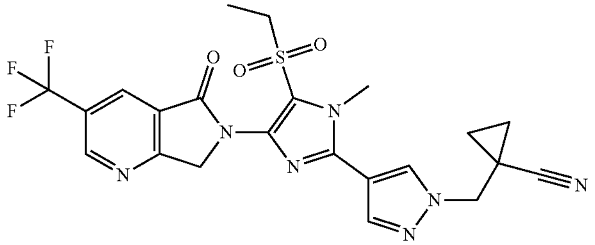 [SMILES: CCS(=O)(=O)c1c(N2Cc3ncc(C(F)(F)F)cc3C2=O)nc(-c2cnn(CC3(C#N)CC3)c2)n1C] | 1.02 | 520 | 1 | 169-171 |
| P5 | 6-[2-[1-(2,2-difluoroethyl)pyrazol-4-yl]-5-ethylsulfonyl-1-methyl-imidazol-4-yl]-3-(trifluoromethyl)-7H-pyrrolo[3,4-b]pyridin-5-one | 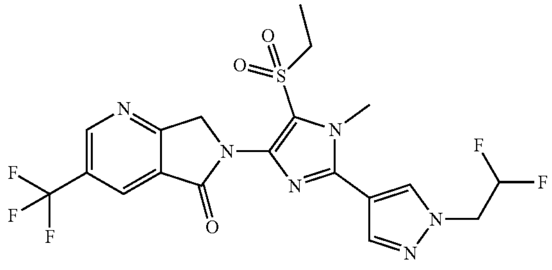 [SMILES: CCS(=O)(=O)c1c(N2Cc3ncc(C(F)(F)F)cc3C2=O)nc(-c2cnn(CC(F)F)c2)n1C] | 1.02 | 505 | 1 | 208-210 |

TABLE P-continued

| Examples of compounds of formula (I) | | | | | | |
|---|---|---|---|---|---|---|
| | | | LCMS | | | |
| No. | IUPAC name | Structures | $R_t$ (min) | [M + H]$^+$ (measured) | Method | Mp (° C) |
| P6 | 6-[5-ethylsulfonyl-1-methyl-2-(2,2,2-trifluoroethoxy) imidazol-4-yl]-3-(trifluoromethyl)-7H-pyrrolo[3,4-b]pyridin-5-one | 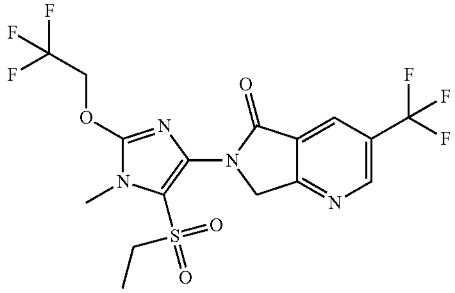 [SMILES: CCS(=O)(=O)c1c(N2Cc3ncc(C(F)(F)F)cc3C2=O)nc(OCC(F)(F)F)n1C] | 1.41 | 473 | 2 | 140-142 |
| P7 | 2-(5-ethylsulfonyl-1-methyl-2-pyrimidin-5-yl-imidazol-4-yl)-6-(trifluoromethoxy) isoindolin-1-one | 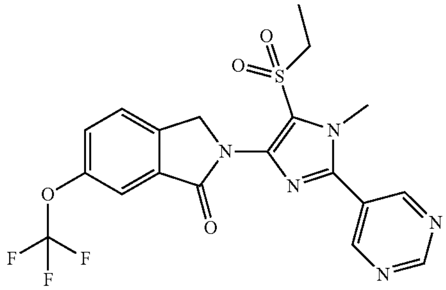 [SMILES: CCS(=O)(=O)c1c(N2Cc3ccc(OC(F)(F)F)cc3C2=O)nc(-c2cncnc2)n1C] | 1.04 | 468 | 1 | 191-193 |
| P8 | 6-(5-ethylsulfonyl-1-methyl-2-pyrimidin-5-yl-imidazol-4-yl)-3-(trifluoromethyl)-7H-pyrrolo[3,4-b]pyridin-5-one | 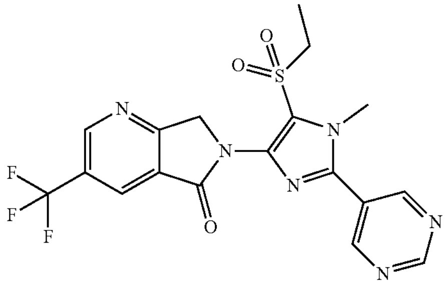 [SMILES: CCS(=O)(=O)c1c(N2Cc3ncc(C(F)(F)F)cc3C2=O)nc(-c2cncnc2)n1C] | 0.97 | 453 | 1 | 256-258 |
| P9 | 6-[2-[1-(cyclopropylmethyl) pyrazol-4-yl]-5-ethylsulfonyl-1-methyl-imidazol-4-yl]-3-(trifluoromethyl)-7H-pyrrolo[3,4-b]pyridin-5-one | 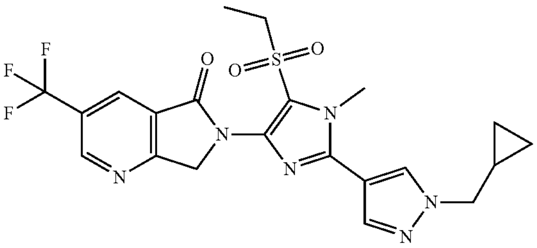 [SMILES: CCS(=O)(=O)c1c(N2Cc3ncc(C(F)(F)F)cc3C2=O)nc(-c2cnn(CC3CC3)c2)n1C] | 1.03 | 495 | 1 | 208-210 |
| P10 | 6-[5-ethylsulfonyl-1-methyl-2-[1-(2,2,2-trifluoroethyl)pyrazol-4-yl]imidazol-4-yl]-3-(trifluoromethyl)-7H-pyrrolo[3,4-b]pyridin-5-one | 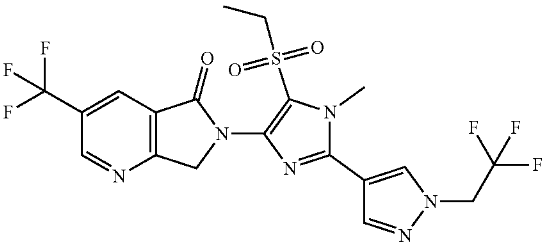 [SMILES: CCS(=O)(=O)c1c(N2Cc3ncc(C(F)(F)F)cc3C2=O)nc(-c2cnn(CC(F)(F)F)c2)n1C] | 1.05 | 523 | 1 | 222-224 |

TABLE P-continued

| Examples of compounds of formula (I) | | | | | | |
|---|---|---|---|---|---|---|
| | | | LCMS | | | |
| No. | IUPAC name | Structures | $R_t$ (min) | $[M + H]^+$ (measured) | Method | Mp (° C) |
| P11 | 2-(5-ethylsulfonyl-1-methyl-2-pyrimidin-2-yl-imidazol-4-yl)-6-(trifluoromethoxy) isoindolin-1-one | 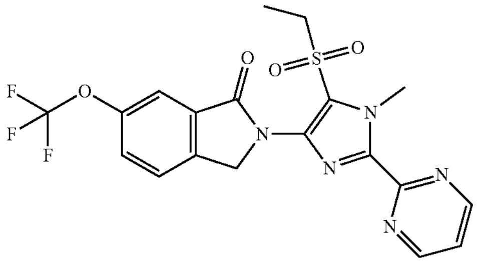 [SMILES: CCS(=O)(=O)c1c(N2Cc3ccc(OC(F)(F)F)cc3C2=O)nc(-c2ncccn2)n1C] | 1.03 | 468 | 1 | 166-168 |
| P12 | 6-(5-ethylsulfonyl-1-methyl-2-pyrimidin-2-yl-imidazol-4-yl)-3-(trifluoromethyl)-7H-pyrrolo[3,4-b]pyridin-5-one | 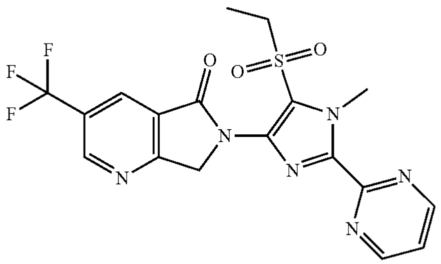 [SMILES: CCS(=O)(=O)c1c(N2Cc3ncc(C(F)(F)F)cc3C2=O)nc(-c2ncccn2)n1C] | 0.98 | 453 | 1 | 230-232 |
| P13 | 6-[2-[1-(difluoromethyl) pyrazol-4-yl]-5-ethylsulfonyl-1-methyl-imidazol-4-yl]-3-(trifluoromethyl)-7H-pyrrolo[3,4-b]pyridin-5-one | 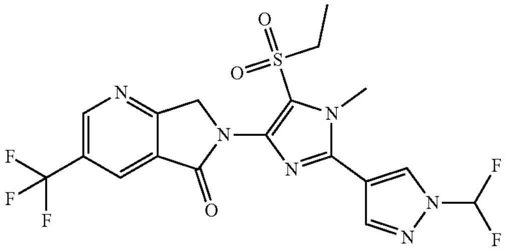 [SMILES: CCS(=O)(=O)c1c(N2Cc3ncc(C(F)(F)F)cc3C2=O)nc(-c2cnn(C(F)F)c2)n1C] | 1.03 | 491 | 1 | 219-221 |
| P14 | 6-[5-ethylsulfonyl-1-methyl-2-[4-(trifluoromethyl) pyrazol-1-yl]imidazol-4-yl]-3-(trifluoromethyl)-7H-pyrrolo[3,4-b]pyridin-5-one | 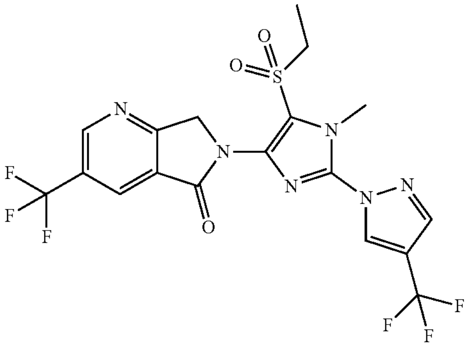 [SMILES: CCS(=O)(=O)c1c(N2Cc3ncc(C(F)(F)F)cc3C2=O)nc(-n2cc(C(F)(F)F)cn2)n1C] | 1.42 | 509 | 2 | 158-160 |
| P15 | 6-[2-(3-cyclopropylpyrazol-1-yl)-5-ethylsulfonyl-1-methyl-imidazol-4-yl]-3-(trifluoromethyl)-7H-pyrrolo[3,4-b]pyridin-5-one | 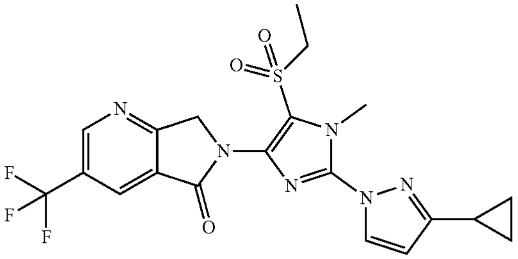 [SMILES: CCS(=O)(=O)c1c(N2Cc3ncc(C(F)(F)F)cc3C2=O)nc(-n2ccc(C3CC3)n2)n1C] | 1.08 | 481 | 1 | 177-179 |

TABLE P-continued

Examples of compounds of formula (I)

| No. | IUPAC name | Structures | LCMS $R_t$ (min) | LCMS $[M + H]^+$ (measured) | Method | Mp (° C) |
|---|---|---|---|---|---|---|
| P16 | 6-[2-(3-chloropyrazol-1-yl)-5-ethylsulfonyl-1-methyl-imidazol-4-yl]-3-(trifluoromethyl)-7H-pyrrolo[3,4-b]pyridin-5-one | 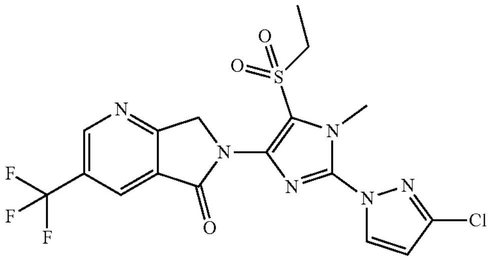 [SMILES: CCS(=O)(=O)c1c(N2Cc3ncc(C(F)(F)F)cc3C2=O)nc(-n2ccc(Cl)n2)n1C] | 1.07 | 475 | 1 | 200-202 |
| P17 | 6-(2-cyclopropyl-5-ethylsulfonyl-1-methyl-imidazol-4-yl)-3-(trifluoromethyl)-7H-pyrrolo[3,4-b]pyridin-5-one | 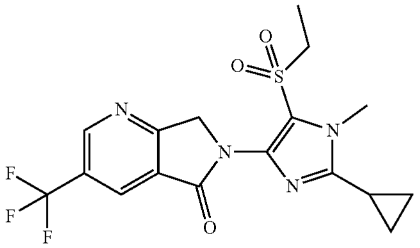 [SMILES: CCS(=O)(=O)c1c(N2Cc3ncc(C(F)(F)F)cc3C2=O)nc(C2CC2)n1C] | 1.00 | 415 | 1 | 190-192 |
| P18 | 1-[4-[5-ethylsulfonyl-1-methyl-4-[5-oxo-3-(trifluoromethyl)-7H-pyrrolo[3,4-b]pyridin-6-yl]imidazol-2-yl]phenyl] cyclopropane-carbonitrile | 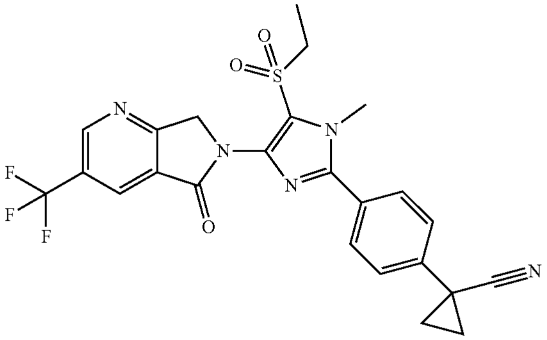 [SMILES: CCS(=O)(=O)c1c(N2Cc3ncc(C(F)(F)F)cc3C2=O)nc(-c2ccc(C3(C#N)CC3)cc2)n1C] | 1.07 | 516 | 1 | 207-209 |

TABLE I

Examples of intermediates

| No. | IUPAC name | Structures | $^1H$ NMR, LCMS, GCMS $R_t$ (min) | $[M]^+$ or $[M + H]^+$ (measured) | Method | Mp (° C) |
|---|---|---|---|---|---|---|
| I-11 | tert-butyl N-[2-(1-cyclopropylpyrazol-4-yl)-5-ethylsulfonyl-1-methyl-imidazol-4-yl]carbamate | 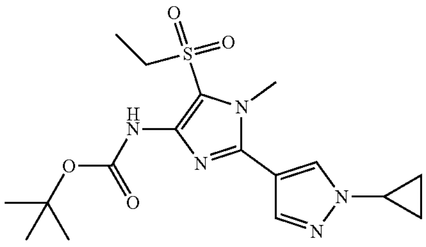 [SMILES: CCS(=O)(=O)c1c(NC(=O)OC(C)(C)C)nc(-c2cnn(C3CC3)c2)n1C] | 1.35 | 396 | 2 | |

TABLE I-continued

Examples of intermediates

| No. | IUPAC name | Structures | $^1$H NMR, LCMS, GCMS: $R_t$ (min) | $[M]^+$ or $[M + H]^+$ (measured) | Method | Mp (° C) |
|---|---|---|---|---|---|---|
| I-10 | 2-(1-cyclopropylpyrazol-4-yl)-5-ethylsulfonyl-1-methyl-imidazole-4-carboxylic acid | 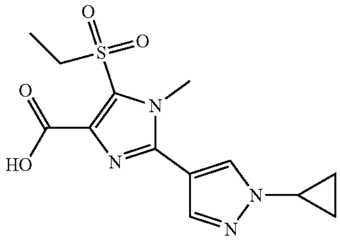 [SMILES: CCS(=O)(=O)c1c(C(=O)O)nc(-c2cnn(C3CC3)c2)n1C] | 0.89 | 325 | 1 | |
| I-15 | 2-(3-cyclopropyl-4,5-dihydroisoxazol-5-yl)-5-ethylsulfonyl-1-methyl-imidazole-4-carboxylic acid | 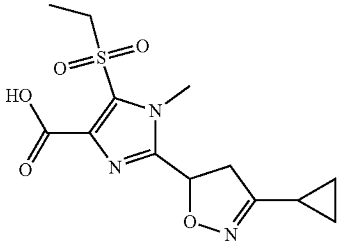 [SMILES: CCS(=O)(=O)c1c(C(=O)O)nc(C2CC(C3CC3)=NO2)n1C] | 1.62 | 328 | 2 | |
| I-16 | tert-butyl N-[2-(3-cyclopropyl-4,5-dihydroisoxazol-5-yl)-5-ethylsulfonyl-1-methyl-imidazol-4-yl]carbamate | 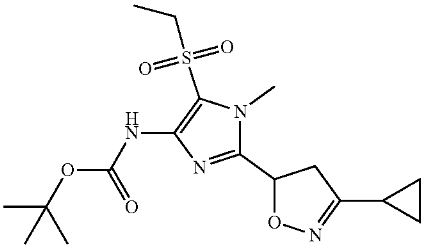 [SMILES: CCS(=O)(=O)c1c(NC(=O)OC(C)(C)C)nc(C2CC(C3CC3)=NO2)n1C] | 1.09 | 343 $[M + H - 56]^+$ | 1 | |
| I-17 | 2-[1-[(1-cyanocyclopropyl)methyl]pyrazol-4-yl]-5-ethylsulfonyl-1-methyl-imidazole-4-carboxylic acid | 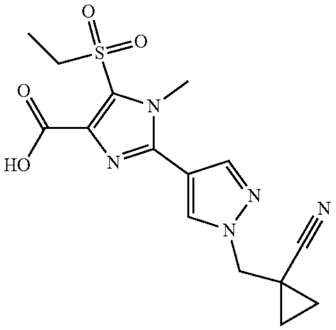 [SMILES: CCS(=O)(=O)c1c(C(=O)O)nc(-c2cnn(CC3(C#N)CC3)c2)n1C] | 0.87 | 364 | 1 | |
| I-18 | tert-butyl N-[2-[1-[(1-cyanocyclopropyl)methyl]pyrazol-4-yl]-5-ethylsulfonyl-1-methyl-imidazol-4-yl]carbamate | 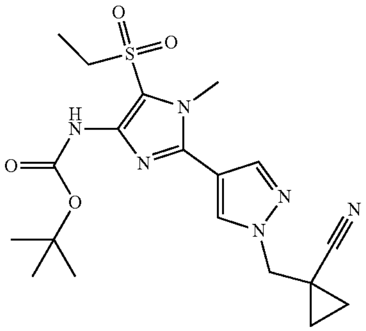 [SMILES: CCS(=O)(=O)c1c(NC(=O)OC(C)(C)C)nc(-c2cnn(CC3(C#N)CC3)c2)n1C] | 1.01 | 433 | 1 | |

TABLE I-continued

Examples of intermediates

| No. | IUPAC name | Structures | $^1$H NMR, LCMS, GCMS R$_t$ (min) | [M]$^+$ or [M + H]$^+$ (measured) | Method | Mp (° C) |
|---|---|---|---|---|---|---|
| I-19 | 2-[1-(2,2-difluoroethyl)pyrazol-4-yl]-5-ethylsulfonyl-1-methyl-imidazole-4-carboxylic acid | 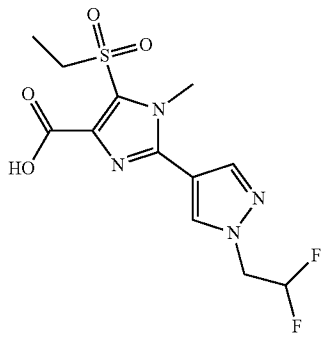 [SMILES: CCS(=O)(=O)c1c(C(=O)O)nc(-c2cnn(CC(F)F)c2)n1C] | 1.00 | 349 | 1 | |
| I-20 | tert-butyl N-[2-[1-(2,2-difluoroethyl)pyrazol-4-yl]-5-ethylsulfonyl-1-methyl-imidazol-4-yl]carbamate | 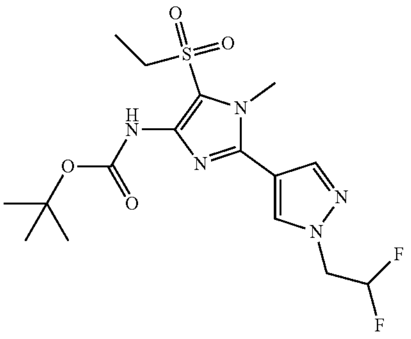 [SMILES: CCS(=O)(=O)c1c(NC(=O)OC(C)(C)C)nc(-c2cnn(CC(F)F)c2)n1C] | 0.99 | 418 | 1 | |
| I-21 | 5-ethylsulfonyl-1-methyl-2-(2,2,2-trifluoroethoxy)imidazole-4-carboxylic acid | 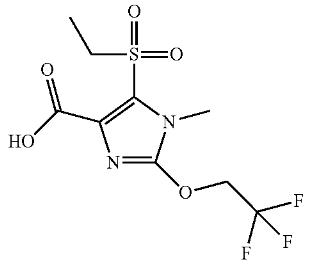 [SMILES: CCS(=O)(=O)c1c(C(=O)O)nc(OCC(F)(F)F)n1C] | 0.95 | 317 | 1 | |
| I-22 | tert-butyl N-[5-ethylsulfonyl-1-methyl-2-(2,2,2-trifluoroethoxy)imidazol-4-yl]carbamate | 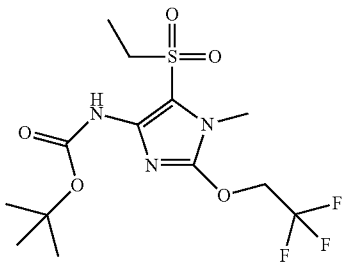 [SMILES: CCS(=O)(=O)c1c(NC(=O)OC(C)(C)C)nc(OCC(F)(F)F)n1C] | 1.10 | 288 [M + H − 100]$^+$ | 1 | |
| I-23 | 5-ethylsulfonyl-1-methyl-2-pyrimidin-5-yl-imidazole-4-carboxylic acid | 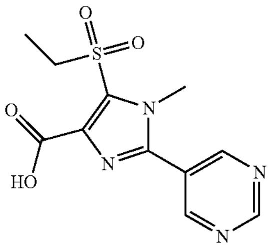 [SMILES: CCS(=O)(=O)c1c(C(=O)O)nc(-c2cncnc2)n1C] | 0.19 | 297 | 1 | |

TABLE I-continued

| Examples of intermediates | | | | | | |
|---|---|---|---|---|---|---|
| | | | $^1$H NMR, LCMS, GCMS | | | |
| No. | IUPAC name | Structures | $R_t$ (min) | $[M]^+$ or $[M + H]^+$ (measured) | Method | Mp (° C) |
| I-24 | tert-butyl N-(5-ethylsulfonyl-1-methyl-2-pyrimidin-5-yl-imidazol-4-yl)carbamate | 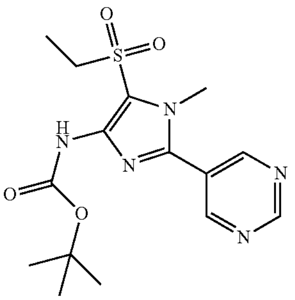 [SMILES: CCS(=O)(=O)c1c(NC(=O)OC(C)(C)C)nc(-c2cncnc2)n1C] | 0.97 | 366 | 1 | |
| I-25 | 2-[1-(cyclopropylmethyl)pyrazol-4-yl]-5-ethylsulfonyl-1-methyl-imidazole-4-carboxylic acid | 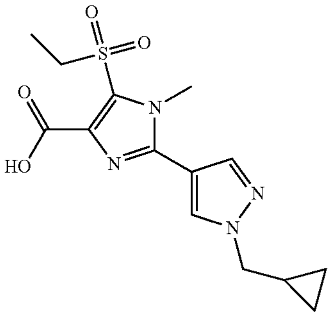 [SMILES: CCS(=O)(=O)c1c(C(=O)O)nc(-c2cnn(CC3CC3)c2)n1C] | 1.05 | 339 | 2 | |
| I-26 | tert-butyl N-[2-[1-(cyclopropylmethyl)pyrazol-4-yl]-5-ethylsulfonyl-1-methyl-imidazol-4-yl]carbamate | 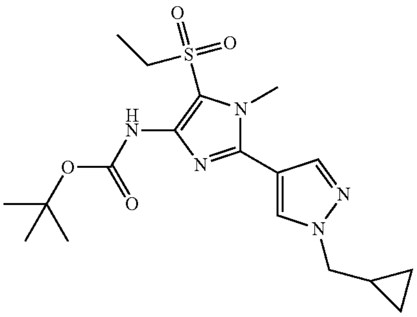 [SMILES: CCS(=O)(=O)c1c(NC(=O)OC(C)(C)C)nc(-c2cnn(CC3CC3)c2)n1C] | 1.36 | 410 | 2 | |
| I-27 | 5-ethylsulfonyl-1-methyl-2-[1-(2,2,2-trifluoroethyl)pyrazol-4-yl]imidazole-4-carboxylic acid | 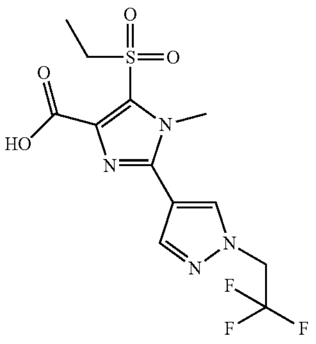 [SMILES: CCS(=O)(=O)c1c(C(=O)O)nc(-c2cnn(CC(F)(F)F)c2)n1C] | 1.00 | 367 | 2 | |

TABLE I-continued

| Examples of intermediates | | | | | | |
|---|---|---|---|---|---|---|
| | | | $^{1}$H NMR, LCMS, GCMS | | | |
| No. | IUPAC name | Structures | $R_t$ (min) | $[M]^+$ or $[M + H]^+$ (measured) | Method | Mp (° C) |
| I-28 | tert-butyl N-[5-ethylsulfonyl-1-methyl-2-[1-(2,2,2-trifluoroethyl)pyrazol-4-yl]imidazol-4-yl]carbamate | 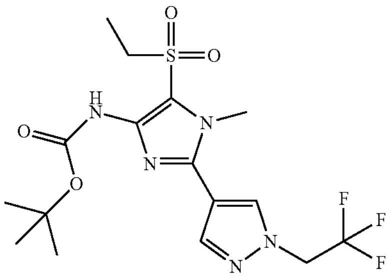 [SMILES: CCS(=O)(=O)c1c(NC(=O)OC(C)(C)C)nc(-c2cnn(CC(F)(F)F)c2)n1C] | 1.09 | 436 | 1 | |
| I-29 | tert-butyl N-(5-ethylsulfonyl-1-methyl-2-pyrimidin-2-yl-imidazol-4-yl)carbamate | 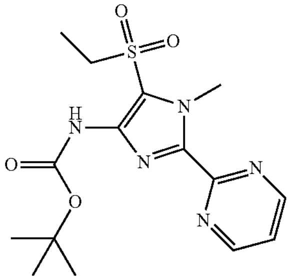 [SMILES: CCS(=O)(=O)c1c(NC(=O)OC(C)(C)C)nc(-c2ncccn2)n1C] | 1.28 | 368 | 2 | |
| I-30 | 5-ethylsulfonyl-1-methyl-2-pyrimidin-2-yl-imidazole-4-carboxylic acid | 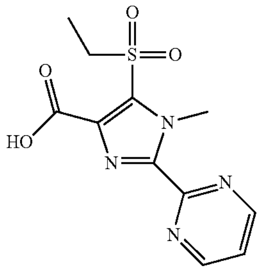 [SMILES: CCS(=O)(=O)c1c(C(=O)O)nc(-c2ncccn2)n1C] | 0.18 | 297 | 1 | |
| I-31 | tert-butyl N-[2-[1-(difluoromethyl)pyrazol-4-yl]-5-ethylsulfonyl-1-methyl-imidazol-4-yl]carbamate | 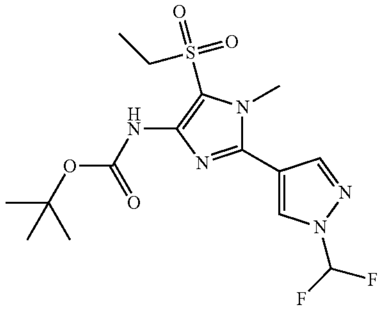 [SMILES: CCS(=O)(=O)c1c(NC(=O)OC(C)(C)C)nc(-c2cnn(C(F)F)c2)n1C] | 1.34 | 406 | 2 | |
| I-32 | 2-[1-(difluoromethyl)pyrazol-4-yl]-5-ethylsulfonyl-1-methyl-imidazole-4-carboxylic acid | 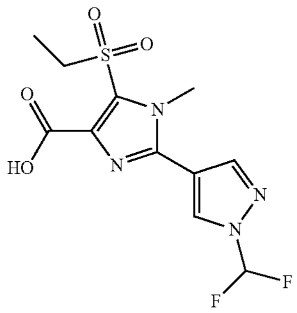 [SMILES: CCS(=O)(=O)c1c(C(=O)O)nc(-c2cnn(C(F)F)c2)n1C] | 0.16 | 335 | 1 | |

TABLE I-continued

| Examples of intermediates | | | | | | | |
|---|---|---|---|---|---|---|---|
| | | | $^1$H NMR, LCMS, GCMS | | | | |
| No. | IUPAC name | Structures | $R_t$ (min) | $[M]^+$ or $[M + H]^+$ (measured) | Method | Mp (° C) |
| I-33 | 5-ethylsulfonyl-1-methyl-2-[4-(trifluoromethyl)pyrazol-1-yl]imidazole-4-carboxylic acid | 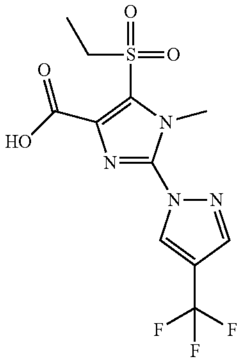 [SMILES: CCS(=O)(=O)c1c(C(=O)O)nc(-n2cc(C(F)(F)F)cn2)n1C] | 1.19 | 353 | 2 | |
| I-34 | tert-butyl N-[5-ethylsulfonyl-1-methyl-2-[4-(trifluoromethyl)pyrazol-1-yl]imidazol-4-yl]carbamate | 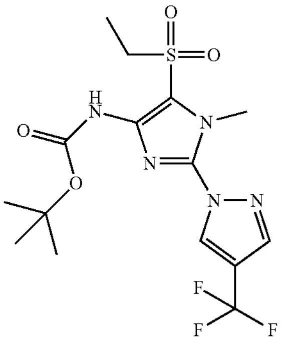 [SMILES: CCS(=O)(=O)c1c(NC(=O)OC(C)(C)C)nc(-n2cc(C(F)(F)F)cn2)n1C] | 1.41 | 423 | 2 | |
| I-35 | 2-(3-chloropyrazol-1-yl)-5-ethylsulfonyl-1-methyl-imidazol-4-amine | 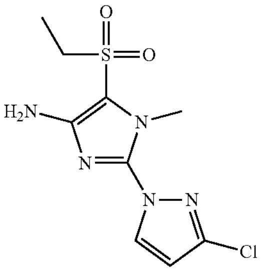 [SMILES: CCS(=O)(=O)c1c(N)nc(-n2ccc(Cl)n2)n1C] | 1.14 | 290 | 2 | |
| I-36 | tert-butyl N-[2-(3-chloropyrazol-1-yl)-5-ethylsulfonyl-1-methyl-imidazol-4-yl]carbamate | 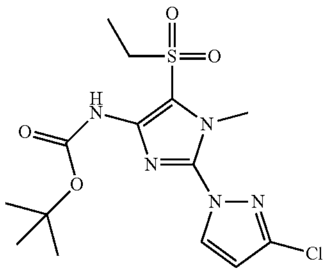 [SMILES: CCS(=O)(=O)c1c(NC(=O)OC(C)(C)C)nc(-n2ccc(Cl)n2)n1C] | 1.37 | 388 | 2 | |

TABLE I-continued

| Examples of intermediates | | | | | | |
|---|---|---|---|---|---|---|
| | | | $^1$H NMR, LCMS, GCMS | | | |
| No. | IUPAC name | Structures | $R_t$ (min) | $[M]^+$ or $[M+H]^+$ (measured) | Method | Mp (° C) |
| I-37 | 2-(3-chloropyrazol-1-yl)-5-ethylsulfonyl-1-methyl-imidazole-4-carboxylic acid | 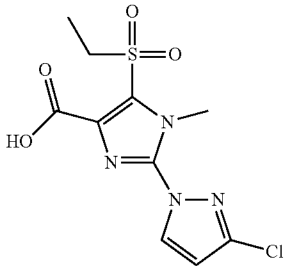 [SMILES: CCS(=O)(=O)c1c(C(=O)O)nc(-n2ccc(Cl)n2)n1C] | 0.92 | 319 | 1 | |
| I-38 | tert-butyl N-[2-[4-(1-cyanocyclopropyl)phenyl]-5-ethylsulfonyl-1-methyl-imidazol-4-yl]carbamate | 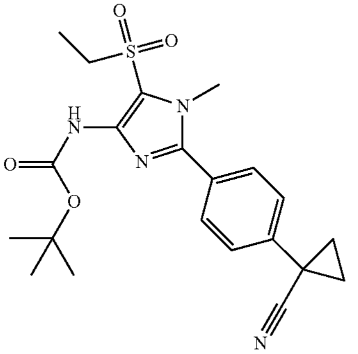 [SMILES: CCS(=O)(=O)c1c(NC(=O)OC(C)(C)C)nc(-c2ccc(C3(C#N)CC3)cc2)n1C] | 1.08 | 431 | 1 | |
| I-39 | 2-[4-(1-cyanocyclopropyl)phenyl]-5-ethylsulfonyl-1-methyl-imidazole-4-carboxylic acid | 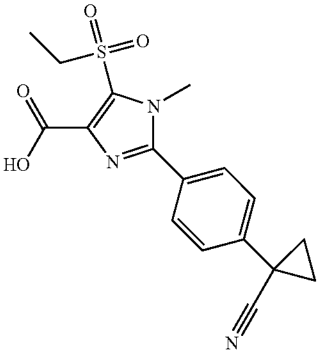 [SMILES: CCS(=O)(=O)c1c(C(=O)O)nc(-c2ccc(C3(C#N)CC3)cc2)n1C] | 0.94 | 360 | 1 | |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables A-1 to A-48, C-1 to C-24, D-1 to D-12, E-1 to E-12 and Table P of the present invention"):

an adjuvant selected from the group of substances consisting of petroleum oils (alternative name) (628)+TX;

an insect control active substance selected from abamectin+TX, acequinocyl+TX, acetamiprid+TX, acetoprole+TX, acrinathrin+TX, acynonapyr+TX, afidopyropen+TX, afoxolaner+TX, alanycarb+TX, allethrin+TX, alpha-cypermethrin+TX, alphamethrin+TX, amidoflumet+TX, aminocarb+TX, azocyclotin+TX, bensultap+TX, benzoximate+TX, benzpyrimoxan+TX, betacyfluthrin+TX, beta-cypermethrin+TX, bifenazate+TX, bifenthrin+TX, binapacryl+TX, bioallethrin+TX, S-bioallethrin+TX, bioresmethrin+TX, bistrifluron+TX, broflanilide+TX, brofluthrinate+TX, bromophos-ethyl+TX, buprofezine+TX, butocarboxim+TX, cadusafos+TX, carbaryl+TX, carbosulfan+TX, cartap+TX, CAS number: 1632218-00-8+TX, CAS number: 1808115-49-2+TX, CAS number: 2032403-97-5+TX, CAS number: 2044701-44-0+TX, CAS number: 2128706-05-6+TX, CAS number: 2095470-94-1+TX, CAS number: 2377084-09-6+TX, CAS number: 1445683-71-5+TX, CAS number: 2408220-94-8+TX, CAS number: 2408220-91-5+TX, CAS number: 1365070-72-9+TX, CAS number: 2171099-09-3+TX, CAS number: 2396747-83-2+TX, CAS number: 2133042-31-4+TX, CAS number: 2133042-44-9+TX, CAS number: 1445684-82-1+TX, CAS number: 1445684-82-1+TX, CAS number: 1922957-45-6+TX, CAS number: 1922957-46-7+TX, CAS number: 1922957-47-8+TX, CAS number: 1922957-48-9+TX, CAS number: 2415706-16-8+TX, CAS number: 1594624-87-9+TX, CAS number: 1594637-65-6+TX, CAS number: 1594626-19-3+TX, CAS number: 1990457-52-7+TX, CAS number: 1990457-55-0+TX, CAS number: 1990457-57-2+TX, CAS number: 1990457-77-6+TX, CAS number: 1990457-66-3+TX, CAS number: 1990457-85-6+TX, CAS number: 2220132-55-6+TX, CAS number: 1255091-74-7+TX, chlorantraniliprole+TX, chlordane+TX, chlorfenapyr+TX, chloroprallethrin+TX, chromafenozide+TX, clenpirin+TX, cloethocarb+TX, clothianidin+TX, 2-chlorophenyl N-methylcarbamate (CPMC)+TX, cyanofenphos+TX, cyantraniliprole+TX, cyclaniliprole+TX, cyclobutrifluram+TX, cycloprothrin+TX, cycloxaprid+TX, cyenopyrafen+TX, cyetpyrafen+TX, cyflumetofen+TX, cyfluthrin+TX, cyhalodiamide+TX, cyhalothrin+TX, cypermethrin+TX, cyphenothrin+TX, cyproflanilide+TX, cyromazine+TX, deltamethrin+TX, diafenthiuron+TX, dialifos+TX, dibrom+TX, dicloromezotiaz+TX, diflovidazine+TX, diflubenzuron+TX, dimpropyridaz+TX, dinactin+TX, dinocap+TX, dinotefuran+TX, dioxabenzofos+TX, emamectin (or emamectin benzoate)+TX, empenthrin+TX, epsilon-momfluorothrin+TX, epsilon-metofluthrin+TX, esfenvalerate+TX, ethion+TX, ethiprole+TX, etofenprox+TX, etoxazole+TX, famphur+TX, fenazaquin+TX, fenfluthrin+TX, fenmezoditiaz+TX, fenitrothion+TX, fenobucarb+TX, fenothiocarb+TX, fenoxycarb+TX, fenpropathrin+TX, fenpyroximate+TX, fensulfothion+TX, fenthion+TX, fentinacetate+TX, fenvalerate+TX, fipronil+TX, flometoquin+TX, flonicamid+TX, fluacrypyrim+TX, fluazaindolizine+TX, fluazuron+TX, flubendiamide+TX, flubenzimine+TX, fluchlordiniliprole+TX, flucitrinate+TX, flucycloxuron+TX, flucythrinate+TX, fluensulfone+TX, flufenerim+TX, flufenprox+TX, flufiprole+TX, fluhexafon+TX, flumethrin+TX, fluopyram+TX, flupentiofenox+TX, flupyradifurone+TX, flupyrimin+TX, fluralaner+TX, fluvalinate+TX, fluxametamide+TX, fosthiazate+TX, gamma-cyhalothrin+TX, Gossyplure™+TX, guadipyr+TX, halofenozide+TX, halfenprox+TX, heptafluthrin+TX, hexythiazox+TX, hydramethylnon+TX, imicyafos+TX, imidacloprid+TX, imiprothrin+TX, indazapyroxamet+TX, indoxacarb+TX, iodomethane+TX, iprodione+TX, isocycloseram+TX, isothioate+TX, ivermectin+TX, kappa-bifenthrin+TX, kappa-tefluthrin+TX, lambda-cyhalothrin+TX, lepimectin+TX, lotilaner+TX, lufenuron+TX, metaflumizone+TX, metaldehyde+TX, metam+TX, methomyl+TX, methoxyfenozide+TX, metofluthrin+TX, metolcarb+TX, mexacarbate+TX, milbemectin+TX, momfluorothrin+TX, niclosamide+TX, nicofluprole+TX; nitenpyram+TX, nithiazine+TX, omethoate+TX, oxamyl+TX, oxazosulfyl+TX, parathion-ethyl+TX, permethrin+TX, phenothrin+TX, phosphocarb+TX, piperonylbutoxide+TX, pirimicarb+TX, pirimiphos-ethyl+TX, pirimiphos-methyl+TX, Polyhedrosis virus+TX, prallethrin+TX, profenofos+TX, profluthrin+TX, propargite+TX, propetamphos+TX, propoxur+TX, prothiophos+TX, protrifenbute+TX, pyflubumide+TX, pymetrozine+TX, pyraclofos+TX, pyrafluprole+TX, pyridaben+TX, pyridalyl+TX, pyrifluquinazon+TX, pyrimidifen+TX, pyriminostrobin+TX, pyriprole+TX, pyriproxyfen+TX, resmethrin+TX, sarolaner+TX, selamectin+TX, silafluofen+TX, spinetoram+TX, spinosad+TX, spirodiclofen+TX, spiromesifen+TX, spiropidion+TX, spirotetramat+TX, spidoxamat+TX, sulfoxaflor+TX, tebufenozide+TX, tebufenpyrad+TX, tebupirimiphos+TX, tefluthrin+TX, temephos+TX, tetrachlorantraniliprole+TX, tetradiphon+TX, tetramethrin+TX, tetramethylfluthrin+TX, tetranactin+TX, tetraniliprole+TX, theta-cypermethrin+TX, thiacloprid+TX, thiamethoxam+TX, thiocyclam+TX, thiodicarb+TX, thiofanox+TX, thiometon+TX, thiosultap+TX, tigolaner+TX, tioxazafen+TX, tolfenpyrad+TX, toxaphene+TX, tralomethrin+TX, transfluthrin+TX, triazamate+TX, triazophos+TX, trichlorfon+TX, trichloronate+TX, trichlorphon+TX, triflumezopyrim+TX, tyclopyrazoflor+TX, zeta-cypermethrin+TX, Extract of seaweed and fermentation product derived from melasse+TX, Extract of seaweed and fermentation product derived from melasse comprising urea+TX, amino acids+TX, potassium and molybdenum and EDTA-chelated manganese+TX, Extract of seaweed and fermented plant products+TX, Extract of seaweed and fermented plant products comprising phytohormones+TX, vitamins+TX, EDTA-chelated copper+TX, zinc+TX, and iron+TX, azadirachtin+TX, *Bacillus aizawai*+TX, *Bacillus chitinosporus* AQ746 (NRRL Accession No B-21 618)+TX, *Bacillus firmus*+TX, *Bacillus kurstaki*+TX, *Bacillus mycoides* AQ726 (NRRL Accession No. B-21664)+TX, *Bacillus pumilus* (NRRL Accession No B-30087)+TX, *Bacillus pumilus* AQ717 (NRRL Accession No. B-21662)+TX, *Bacillus* sp. AQ178 (ATCC Accession No. 53522)+TX, *Bacillus* sp. AQ175 (ATCC Accession No. 55608)+TX, *Bacillus* sp. AQ177 (ATCC Accession No. 55609)+TX, *Bacillus subtilis* unspecified+TX, *Bacillus subtilis* AQ153 (ATCC Accession No. 55614)+TX, *Bacillus subtilis* AQ30002 (NRRL Accession No. B-50421)+TX, *Bacillus subtilis* AQ30004 (NRRL Accession No. B-50455)+TX, *Bacillus subtilis* AQ713 (NRRL Accession No. B-21661)+TX, *Bacillus subtilis* AQ743 (NRRL Accession No. B-21665)+TX, *Bacillus thuringiensis* AQ52 (NRRL Accession No. B-21619)+TX, *Bacillus thuringiensis* BD #32 (NRRL Accession No B-21530)+TX, *Bacillus thuringiensis* subspec. *kurstaki* BMP 123+TX, *Beauveria bassiana*+TX, D-limonene+TX, Granulovirus+TX, Harpin+TX, *Helicoverpa armigera* Nucleopolyhedrovirus+TX, *Helicoverpa zea* Nucleopolyhedrovirus+TX, *Heliothis virescens* Nucleopolyhedrovirus+TX, *Heliothis punctigera* Nucleopolyhedrovirus+TX, *Metarhizium* spp.+TX, *Muscodor albus* 620 (NRRL Accession No. 30547)+TX, *Muscodor roseus* A3-5

(NRRL Accession No. 30548)+TX, Neem tree based products+TX, *Paecilomyces fumosoroseus*+TX, *Paecilomyces lilacinus*+TX, *Pasteuria nishizawae*+TX, *Pasteuria penetrans*+TX, *Pasteuria ramosa*+TX, *Pasteuria thornei*+TX, *Pasteuria usgae*+TX, P-cymene+TX, *Plutella xylostella* Granulosis virus+TX, *Plutella xylostella* Nucleopolyhedrovirus+TX, Polyhedrosis virus+TX, *Pyrethrum*+TX, QRD 420 (a terpenoid blend)+TX, QRD 452 (a terpenoid blend)+TX, QRD 460 (a terpenoid blend)+TX, *Quillaja saponaria*+TX, *Rhodococcus globerulus* AQ719 (NRRL Accession No B-21663)+TX, *Spodoptera frugiperda* Nucleopolyhedrovirus+TX, *Streptomyces galbus* (NRRL Accession No. 30232)+TX, *Streptomyces* sp. (NRRL Accession No. B-30145)+TX, Terpenoid blend+TX, and *Verticillium* spp.;

an algaecide selected from the group of substances consisting of bethoxazine [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX;

an anthelmintic selected from the group of substances consisting of abamectin (1)+TX, crufomate (1011)+TX, cyclobutrifluram+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX;

an avicide selected from the group of substances consisting of chloralose (127)+TX, endrin (1122)+TX, fenthion (346)+TX, pyridin-4-amine (IUPAC name) (23) and strychnine (745)+TX; a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX;

a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX;

a soil sterilant selected from the group of substances consisting of iodomethane (IUPAC name) (542) and methyl bromide (537)+TX;

a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX;

an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)- tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX;

an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX;

a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX; a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cyclobutrifluram+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium* verrucaria composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, fluopyram+TX;

a nitrification inhibitor selected from the group of substances consisting of potassium ethylxanthate [CCN] and nitrapyrin (580)+TX;

a plant activator selected from the group of substances consisting of acibenzolar (6)+TX, acibenzolar-S-methyl (6)+TX, probenazole (658) and *Reynoutria sachalinensis* extract (alternative name) (720)+TX;

a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (including alpha-bromadiolone)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX; a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX;

an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX;

a virucide selected from the group of substances consisting of imanin (alternative name) [CCN] and ribavirin (alternative name) [CCN]+TX;

a wound protectant selected from the group of substances consisting of mercuric oxide (512)+TX, octhilinone (590) and thiophanate-methyl (802)+TX;

a biologically active substance selected from 1,1-bis(4-chloro-phenyl)-2-ethoxyethanol+TX, 2,4-dichlorophenyl benzenesulfonate+TX, 2-fluoro-N-methyl-N-1-naphthylacetamide+TX, 4-chlorophenyl phenyl sulfone+TX, acetoprole+TX, aldoxycarb+TX, amidithion+TX, amidothioate+TX, amiton+TX, amiton hydrogen oxalate+TX, amitraz+TX, aramite+TX, arsenous oxide+TX, azobenzene+TX, azothoate+TX, benomyl+TX, benoxa-fos+TX, benzyl benzoate+TX, bixafen+TX, brofenvalerate+TX, bromo-cyclen+TX, bromophos+TX, bromopropylate+TX, buprofezin+TX, butocarboxim+TX, butoxycarboxim+TX, butylpyridaben+TX, calcium polysulfide+TX, camphechlor+TX, carbanolate+TX, carbophenothion+TX, cymiazole+TX, chino-methionat+TX, chlorbenside+TX, chlordimeform+TX, chlordimeform hydrochloride+TX, chlorfenethol+TX, chlorfenson+TX, chlorfensulfide+TX, chlorobenzilate+TX, chloromebuform+TX, chloromethiuron+TX, chloropropylate+TX, chlorthiophos+TX, cinerin I+TX, cinerin II+TX, cinerins+TX, closantel+TX, coumaphos+TX, crotamiton+TX, crotoxyphos+TX, cufraneb+TX, cyanthoate+TX, DCPM+TX, DDT+TX, demephion+TX, demephion-O+TX, demephion-S+TX, demeton-methyl+TX, demeton-O+TX, demeton-O-methyl+TX, demeton-S+TX, demeton-S-methyl+TX, demeton-S-methylsulfon+TX, dichlofluanid+TX, dichlorvos+TX, dicliphos+TX, dienochlor+TX, dimefox+TX, dinex+TX, dinex-diclexine+TX, dinocap-4+TX, dinocap-6+TX, dinocton+TX, dino-penton+TX, dinosulfon+TX, dinoterbon+TX, dioxathion+TX, diphenyl sulfone+TX, disulfiram+TX, DNOC+TX, dofenapyn+TX, doramectin+TX, endothion+TX, eprinomectin+TX, ethoate-methyl+TX, etrimfos+TX, fenazaflor+TX, fenbutatin oxide+TX, fenothiocarb+TX, fenpyrad+TX, fen-pyroximate+TX, fenpyrazamine+TX, fenson+TX, fentrifanil+TX, flubenzimine+TX, flucycloxuron+TX, fluenetil+TX, fluorbenside+TX, FMC 1137+TX, formetanate+TX, formetanate hydrochloride+TX, formparanate+TX, gamma-HCH+TX, glyodin+TX, halfenprox+TX, hexadecyl cyclopropanecarboxylate+TX, isocarbophos+TX, jasmolin I+TX, jasmolin II+TX, jodfenphos+TX, lindane+TX, malonoben+TX, mecarbam+TX, mephosfolan+TX, mesulfen+TX, methacrifos+TX, methyl bromide+TX, metolcarb+TX, mexacarbate+TX, milbemycin oxime+TX, mipafox+TX, monocrotophos+TX, morphothion+TX, moxidectin+TX, naled+TX, 4-chloro-2-(2-chloro-2-methyl-propyl)-5-[(6-iodo-3-pyridyl)methoxy]pyridazin-3-one+TX, nifluridide+TX, nikkomycins+TX, nitrilacarb+TX, nitrilacarb 1:1 zinc chloride complex+TX, omethoate+TX, oxydeprofos+TX, oxydisulfoton+TX, pp'-DDT+TX, parathion+TX, permethrin+TX, phenkapton+TX, phosalone+TX, phosfolan+TX, phosphamidon+TX, polychloroterpenes+TX, polynactins+TX, proclonol+TX, promacyl+TX, propoxur+TX, prothidathion+TX, prothoate+TX, pyrethrin I+TX, pyrethrin II+TX, pyrethrins+TX, pyridaphenthion+TX, pyrimitate+TX, quinalphos+TX, quintiofos+TX, R-1492+TX, phosglycin+TX, rotenone+TX, schradan+TX, sebufos+TX, selamectin+TX, sophamide+TX, SSI-121+TX, sulfiram+TX, sulfluramid+TX, sulfotep+TX, sulfur+TX, diflovidazin+TX, tau-fluvalinate+TX, TEPP+TX, terbam+TX, tetradifon+TX, tetrasul+TX, thiafenox+TX, thiocarboxime+TX, thiofanox+TX, thiometon+TX, thioquinox+TX, thuringiensin+TX, triamiphos+TX, triarathene+TX, triazophos+TX, triazuron+TX, trifenofos+TX, trinactin+TX, vamidothion+TX, vaniliprole+TX, bethoxazin+TX, copper dioctanoate+TX, copper sulfate+TX, cybutryne+TX, dichlone+TX, dichlorophen+TX, endothal+TX, fentin+TX, hydrated lime+TX, nabam+TX, quinoclamine+TX, quinonamid+TX, simazine+TX, triphenyltin acetate+TX, triphenyltin hydroxide+TX, crufomate+TX, piperazine+TX, thiophanate+TX, chloralose+TX, fenthion+TX, pyridin-4-amine+TX, strychnine+TX, 1-hydroxy-1H-pyridine-2-thione+TX, 4-(quinoxalin-2-ylamino)benzenesulfonamide+TX, 8-hydroxyquinoline sulfate+TX, bronopol+TX, copper hydroxide+TX, cresol+TX, dipyrithione+TX, dodicin+TX, fenaminosulf+TX, formaldehyde+TX, hydrargaphen+TX, kasugamycin+TX, kasugamycin hydrochloride hydrate+TX, nickel bis (dimethyldithiocarbamate)+TX, nitrapyrin+TX, octhilinone+TX, oxolinic acid+TX, oxytetracycline+TX, potassium hydroxyquinoline sulfate+TX, probenazole+TX, streptomycin+TX, streptomycin sesquisulfate+TX, tecloftalam+TX, thiomersal+TX, *Adoxophyes orana* GV+TX, *Agrobacterium radiobacter*+TX, *Amblyseius* spp.+TX, *Anagrapha falcifera* NPV+TX, *Anagrus atomus*+TX, *Aphelinus abdominalis*+TX, *Aphidius colemani*+TX, *Aphidoletes aphidimyza*+TX, *Autographa californica* NPV+TX, *Bacillus sphaericus* Neide+TX, *Beauveria brongniartii*+TX, *Chrysoperla carnea*+TX, *Cryptolaemus montrouzieri*+TX, *Cydia pomonella* GV+TX, *Dacnusa sibirica*+TX, *Diglyphus isaea*+TX, *Encarsia formosa*+TX, *Eretmocerus eremicus*+TX, *Heterorhabditis bacteriophora* and *H. megidis*+TX, *Hippodamia convergens*+TX, *Leptomastix dactylopii*+TX, *Macrolophus caliginosus*+TX, *Mamestra brassicae* NPV+TX, *Metaphycus helvolus*+TX, *Metarhizium anisopliae* var. *acridum*+TX, *Metarhizium anisopliae* var. *anisopliae*+TX, *Neodiprion sertifer* NPV and *N. lecontei* NPV+TX, *Orius* spp.+TX, *Paecilomyces fumosoroseus*+TX, *Phytoseiulus persimilis*+TX, *Steinernema bibionis*+TX, *Steinernema carpocapsae*+TX, *Steinernema feltiae*+TX, *Steinernema glaseri*+TX, *Steinernema riobrave*+TX, *Steinernema riobravis*+TX, *Steinernema scapterisci*+TX, *Steinernema* spp.+TX, *Trichogramma* spp.+TX, *Typhlodromus occidentalis*+TX, *Verticillium lecanii*+TX, apholate+TX, bisazir+TX, busulfan+TX, dimatif+TX, hemel+TX, hempa+TX, metepa+TX, methiotepa+TX, methyl apholate+TX, morzid+TX, penfluron+TX, tepa+TX, thiohempa+TX, thiotepa+TX, tretamine+TX, uredepa+TX, (E)-dec-5-en-1-yl acetate with (E)-dec-5-en-1-ol+TX, (E)-tridec-4-en-1-yl acetate+TX, (E)-6-methylhept-2-en-4-ol+TX, (E,Z)-tetradeca-4,10-dien-1-yl acetate+TX, (Z)-dodec-7-en-1-yl acetate+TX, (Z)-hexadec-11-enal+TX, (Z)-hexadec-11-en-1-yl acetate+TX, (Z)-hexadec-13-en-11-yn-1-yl acetate+TX, (Z)-icos-13-en-10-one+TX, (Z)-tetradec-7-en-1-al+TX, (Z)-tetradec-9-en-1-ol+TX, (Z)-tetradec-9-en-1-yl acetate+TX, (7E,9Z)-dodeca-7,9-dien-1-yl acetate+TX, (9Z,11E)-tetradeca-9,11-dien-1-yl acetate+TX, (9Z,12E)-tetradeca-9,12-dien-1-yl acetate+TX, 14-methyloctadec-1-ene+TX, 4-methylnonan-5-ol with 4-methylnonan-5-one+TX, alpha-multistriatin+TX, brevicomin+TX, codlelure+TX, codlemone+TX, cuelure+TX, disparlure+TX, dodec-8-en-1-yl acetate+TX, dodec-9-en-1-yl acetate+TX, dodeca-8+TX, 10-dien-1-yl acetate+TX, dominicalure+TX, ethyl 4-methyloctanoate+TX, eugenol+TX, frontalin+TX, grandlure+TX, grandlure I+TX, grandlure II+TX, grandlure III+TX, grandlure IV+TX, hexalure+TX, ipsdienol+TX, ipsenol+TX, japonilure+TX, lineatin+TX, litlure+TX, looplure+TX, medlure+TX, megatomoic acid+TX, methyl eugenol+TX, muscalure+TX, octadeca-2,13-dien-1-yl acetate+TX, octadeca-3,13-dien-1-yl acetate+TX, orfralure+TX, oryctalure+TX, ostramone+TX, siglure+TX, sordidin+TX, sulcatol+TX, tetradec-11-en-1-yl acetate+TX, trimedlure+TX, trimedlure A+TX, trimedlure $B_1$+TX, trimedlure $B_2$+TX, trimedlure C+TX, trunc-call+TX, 2-(octylthio)-ethanol+TX, butopyronoxyl+TX, butoxy(polypropylene glycol)+TX, dibutyl adipate+TX, dibutyl phthalate+TX, dibutyl succinate+TX, diethyltoluamide+TX, dimethyl carbate+TX, dimethyl phthalate+TX, ethyl hexanediol+TX, hexamide+TX, methoquin-butyl+TX, methylneodecanamide+TX, oxamate+TX, picaridin+TX, 1-dichloro-1-nitroethane+TX, 1,1-dichloro-2,2-bis(4-ethylphenyl)-ethane+TX, 1,2-dichloropropane with 1,3-dichloropropene+TX, 1-bromo-2-chloroethane+TX, 2,2,2-trichloro-1-(3,4-dichlorophenyl)ethyl acetate+TX, 2,2-dichlorovinyl 2-ethylsulfinylethyl methyl phosphate+TX, 2-(1,3-dithiolan-2-yl)phenyl dimethylcarbamate+TX, 2-(2-butoxyethoxy)ethyl thiocyanate+TX, 2-(4,5-dimethyl-1,3-dioxolan-2-yl)phenyl methylcarbamate+TX, 2-(4-chloro-3,5-xylyloxy)ethanol+TX, 2-chlorovinyl diethyl phosphate+TX, 2-imidazolidone+TX, 2-isovalerylindan-1,3-dione+TX, 2-methyl(prop-2-ynyl)aminophenyl methylcarbamate+TX, 2-thiocyanatoethyl laurate+TX, 3-bromo-1-chloroprop-1-ene+TX, 3-methyl-1-phenylpyrazol-5-yl dimethyl-carbamate+TX, 4-methyl(prop-2-ynyl)amino-3,5-xylyl methylcarbamate+TX, 5,5-dimethyl-3-oxocyclohex-1-enyl dimethylcarbamate+TX, acethion+TX, acrylonitrile+TX, aldrin+TX, allosamidin+TX, allyxycarb+TX, alpha-ecdysone+TX, aluminium phosphide+TX, aminocarb+TX, anabasine+TX, athidathion+TX, azamethiphos+TX, *Bacillus thuringiensis* delta endotoxins+TX, barium hexafluorosilicate+TX, barium polysulfide+TX, barthrin+TX, Bayer 22/190+TX, Bayer 22408+TX, beta-cyfluthrin+TX, beta-cypermethrin+TX, bioethanomethrin+TX, biopermethrin+TX, bis(2-chloroethyl) ether+TX, borax+TX, bromfenvinfos+TX, bromo-DDT+TX, bufencarb+TX, butacarb+TX, butathiofos+TX, butonate+TX, calcium arsenate+TX, calcium cyanide+TX, carbon disulfide+TX, carbon tetrachloride+TX, cartap hydrochloride+TX, cevadine+TX, chlorbicyclen+TX, chlordane+TX, chlordecone+TX, chloroform+TX, chloropicrin+TX, chlorphoxim+TX, chlorprazophos+TX, cis-resmethrin+TX, cismethrin+TX, clocythrin+TX, copper acetoarsenite+TX, copper arsenate+TX, copper oleate+TX, coumithoate+TX, cryolite+TX, CS 708+TX, cyanofenphos+TX, cyanophos+TX, cyclethrin+TX, cythioate+TX, d-tetramethrin+TX, DAEP+TX, dazomet+TX, decarbofuran+TX, diamidafos+TX, dicapthon+TX, dichlofenthion+TX, dicresyl+TX, dicyclanil+TX, dieldrin+TX, diethyl 5-methylpyrazol-3-yl phosphate+TX, dilor+TX, dimefluthrin+TX, dimetan+TX, dimethrin+TX, dimethylvinphos+TX, dimetilan+TX, dinoprop+TX, dinosam+TX, dinoseb+TX, diofenolan+TX, dioxabenzofos+TX, dithicrofos+TX, DSP+TX, ecdysterone+TX, El 1642+TX, EMPC+TX, EPBP+TX, etaphos+TX, ethiofencarb+TX, ethyl formate+TX, ethylene dibromide+TX, ethylene dichloride+TX, ethylene oxide+TX, EXD+TX, fenchlorphos+TX, fenethacarb+TX, fenitrothion+TX, fenoxacrim+TX, fenpirithrin+TX, fensulfothion+TX, fenthion-ethyl+TX, flucofuron+TX, fosmethilan+TX, fospirate+TX, fosthietan+TX, furathiocarb+TX, furethrin+TX, guazatine+TX, guazatine acetates+TX, sodium tetrathiocarbonate+TX, halfenprox+TX, HCH+TX, HEOD+TX, heptachlor+TX, heterophos+TX, HHDN+TX, hydrogen cyanide+TX, hyquincarb+TX, IPSP+TX, isazofos+TX, isobenzan+TX, isodrin+TX, isofenphos+TX, isolane+TX, isoprothiolane+TX, isoxathion+TX, juvenile hormone I+TX, juvenile hormone II+TX, juvenile hormone III+TX, kelevan+TX, kinoprene+TX, lead arsenate+TX, leptophos+TX, lirimfos+TX, lythidathion+TX, m-cumenyl methylcarbamate+TX, magnesium phosphide+TX, mazidox+TX, mecarphon+TX, menazon+TX, mercurous chloride+TX, mesulfenfos+TX, metam+TX, metam-potassium+TX, metam-sodium+TX, methanesulfonyl fluoride+TX, methocrotophos+TX, methoprene+TX, methothrin+TX, methoxychlor+TX, methyl isothiocyanate+TX, methylchloroform+TX, methylene chloride+TX, metoxadiazone+TX, mirex+TX, naftalofos+TX, naphthalene+TX, NC-170+TX, nicotine+TX, nicotine sulfate+TX, nithiazine+TX, nornicotine+TX, O-5-dichloro-4-iodophenyl O-ethyl ethylphosphonothioate+TX, O,O-diethyl O-4-methyl-2-oxo-2H-chromen-7-yl phosphorothioate+TX, O,O-diethyl O-6-methyl-2-propylpyrimidin-4-yl phosphorothioate+TX, O,O,O',O'-tetrapropyl dithiopyrophosphate+TX, oleic acid+TX, para-dichlorobenzene+TX, parathion-methyl+TX, pentachlorophenol+TX, pentachlorophenyl laurate+TX, PH 60-38+TX, phenkapton+TX, phosnichlor+TX, phosphine+TX, phoxim-methyl+TX, pirimetaphos+TX, polychlorodicyclopentadiene isomers+TX, potassium arsenite+TX, potassium thiocyanate+TX, precocene I+TX, precocene II+TX, precocene III+TX, primidophos+TX, profluthrin+TX, promecarb+TX, prothiofos+TX, pyrazophos+TX, pyresmethrin+TX, quassia+TX, quinalphos-methyl+TX, quinothion+TX, rafoxanide+TX, resmethrin+TX, rotenone+TX, kadethrin+TX, ryania+TX, ryanodine+TX, sabadilla+TX, schradan+TX, sebufos+TX, SI-0009+TX, thiapronil+TX, sodium arsenite+TX, sodium cyanide+TX, sodium fluoride+TX, sodium hexafluorosilicate+TX, sodium pentachlorophenoxide+TX, sodium selenate+TX, sodium thiocyanate+TX, sulcofuron+TX, sulcofuron-sodium+TX, sulfuryl fluoride+TX, sulprofos+TX, tar oils+TX, tazimcarb+TX, TDE+TX, tebupirimfos+TX, temephos+TX, terallethrin+TX, tetrachloroethane+TX, thicrofos+TX, thiocyclam+TX, thiocyclam hydrogen oxalate+TX, thionazin+TX, thiosultap+TX, thiosultap-sodium+TX, tralomethrin+TX, transpermethrin+TX, triazamate+TX, trichlormetaphos-3+TX, trichloronat+TX, trimethacarb+TX, tolprocarb+TX, triclopyricarb+TX, triprene+TX, veratridine+TX, veratrine+TX, XMC+TX, zetamethrin+TX, zinc phosphide+TX, zolaprofos+TX, meperfluthrin+TX, tetramethylfluthrin+TX, bis(tributyltin) oxide+TX, bromoacetamide+TX, ferric phosphate+TX, niclosamide-olamine+TX, tributyltin oxide+TX, pyrimorph+TX, trifenmorph+TX, 1,2-dibromo-3-chloropropane+TX, 1,3-dichloropropene+TX, 3,4-dichlorotetrahydrothio-phene 1,1-dioxide+TX, 3-(4-chlorophenyl)-5-methylrhodanine+TX, 5-methyl-6-thioxo-1,3,5-thiadiazinan-3-ylacetic acid+TX, 6-isopentenylaminopurine+TX, anisiflupurin+TX, benclothiaz+TX, cytokinins+TX, DCIP+TX, furfural+TX, isamidofos+TX, kinetin+TX, *Myrothecium verrucaria* composition+TX, tetrachlorothiophene+TX, xylenols+TX, zeatin+TX, potassium ethylxanthate+TX, acibenzolar+TX, acibenzolar-S-methyl+TX, *Reynoutria sachalinensis* extract+TX, alpha-chlorohydrin+TX, antu+TX, barium carbonate+TX, bisthiosemi+TX, brodifacoum+TX, bromadiolone+TX, bromethalin+TX, chlorophacinone+TX, cholecalciferol+TX, coumachlor+TX, coumafuryl+TX, coumatetralyl+TX, crimidine+TX, difenacoum+TX, difethialone+TX, diphacinone+TX, ergocalciferol+TX, flocoumafen+TX, fluoroacetamide+TX, flupropadine+TX, flupropadine hydrochloride+TX, norbormide+TX, phosacetim+TX, phosphorus+TX, pindone+TX, pyrinuron+TX, scilliroside+TX, -sodium fluoroacetate+TX, thallium sulfate+TX, warfarin+TX, –2-(2-butoxyethoxy)ethyl piperonylate+TX, 5-(1,3-benzodioxol-5-yl)-3-hexylcyclohex-2-enone+TX, farnesol with nerolidol+TX, verbutin+TX, MGK 264+TX, piperonyl butoxide+TX, piprotal+TX, propyl isomer+TX, S421+TX, sesamex+TX, sesasmolin+TX, sulfoxide+TX, anthraquinone+TX, copper naphthenate+TX, copper oxychloride+TX, dicyclopentadiene+TX, thiram+TX, zinc naphthenate+TX, ziram+TX, imanin+TX, ribavirin+TX, chloroinconazide+TX, mercuric oxide+TX, thiophanate-methyl+TX, azaconazole+TX, bitertanol+TX, bromuconazole+TX, cyproconazole+TX, difenoconazole+TX, diniconazole—+TX, epoxiconazole+TX, fenbuconazole+TX, fluquinconazole+TX, flusilazole+TX, flutriafol+TX, furametpyr+TX, hexaconazole+TX, imazalil—+TX, imiben-conazole+TX, ipconazole+TX, metconazole+TX, myclobutanil+TX, paclobutrazole+TX, pefurazoate+TX, penconazole+TX, prothioconazole+TX, pyrifenox+TX, prochloraz+TX, propiconazole+TX, pyrisoxazole+TX, -simeconazole+TX, tebucon-azole+TX, tetraconazole+TX, triadimefon+TX, triadimenol+TX, triflumizole+TX, triticonazole+TX, ancymidol+TX, fenarimol+TX, nuarimol+TX, bupirimate+TX, dimethirimol+TX, ethirimol+TX, dodemorph+TX, fenpropidin+TX, fenpropimorph+TX, spiroxamine+TX, tridemorph+TX, cyprodinil+TX, mepanipyrim+TX, pyrimethanil+TX, fenpiclonil+TX, fludioxonil+TX, benalaxyl+TX, furalaxyl+TX, —metalaxyl—+TX, Rmetalaxyl+TX, ofurace+TX, oxadixyl+TX, carbendazim+TX, debacarb+TX, fuberidazole—+TX, thiabendazole+TX, chlozolinate+TX, dichlozoline+TX, myclozoline—+TX, procymidone+TX, vinclozoline+TX, boscalid+TX, carboxin+TX, fenfuram+TX, flutolanil+TX, mepronil+TX, oxycarboxin+TX, penthiopyrad+TX, thifluzamide+TX, dodine+TX, iminoctadine+TX, azoxystrobin+TX, dimoxystrobin+TX, enestroburin+TX, fenaminstrobin+TX, flufenoxystrobin+TX, fluoxastrobin+TX, kresoxim—methyl+TX, metominostrobin+TX, trifloxystrobin+TX, orysastrobin+TX, picoxystrobin+TX, pyraclostrobin+TX, pyrametostrobin+TX, pyraoxystrobin+TX, ferbam+TX, mancozeb+TX, maneb+TX, metiram+TX, propineb+TX, zineb+TX, captafol+TX, captan+TX, fluoroimide+TX, folpet+TX, tolylfluanid+TX, bordeaux mixture+TX, copper oxide+TX, mancopper+TX, oxine-copper+TX, nitrothal-isopropyl+TX, edifenphos+TX, iprobenphos+TX, phosdiphen+TX, tolclofos-methyl+TX, anilazine+TX, benthiavalicarb+TX, blasticidin-S+TX, chloroneb—+TX, chloro-thalonil+TX, cyflufenamid+TX, cymoxanil+TX, cyclobutrifluram+TX, diclocymet+TX, diclomezine—+TX, dicloran+TX, diethofencarb+TX, dimethomorph—+TX, flumorph+TX, dithianon+TX, ethaboxam+TX, etridiazole+TX, famoxadone+TX, fenamidone+TX, fenoxanil+TX, ferimzone+TX, fluazinam+TX, flumetylsulforim+TX, fluopicolide+TX, fluoxytioconazole+TX, flusulfamide+TX, fluxapyroxad+TX, —fenhexamid+TX, fosetyl-aluminium—+TX, hymexazol+TX, iprovalicarb+TX, cyazofamid+TX, methasulfocarb+TX, metrafenone+TX, pencycuron+TX, phthalide+TX, polyoxins+TX, propamocarb+TX, pyribencarb+TX, proquinazid+TX, pyroquilon+TX, pyriofenone+TX, quinoxyfen+TX, quintozene+TX, tiadinil+TX, triazoxide+TX, tricyclazole+TX, triforine+TX, validamycin+TX, valifenalate+TX, zoxamide+TX, mandipropamid+TX, flubeneteram+TX, isopyrazam+TX, sedaxane+TX, benzovindiflupyr+TX, pydiflumetofen+TX, 3-difluoromethyl-1-methyl-1H-pyrazole-4-carboxylic acid (3',4',5'-trifluoro-biphenyl-2-yl)-amide+TX, isoflucypram+TX, isotianil+TX, dipymetitrone+TX, 6-ethyl-5,7-dioxo-pyrrolo[4,5][1,4]dithiino[1,2-c]isothiazole-3-carbonitrile+TX, 2-(difluoromethyl)-N-[3-ethyl-1,1-dimethyl-indan-4-yl]pyridine-3-carboxamide+TX, 4-(2,6-difluorophenyl)-6-methyl-5-phenyl-pyridazine-3-carbonitrile+TX, (R)-3-(difluoromethyl)-1-methyl-N-[1,1,3-trimethylindan-4-yl]pyrazole-4-carboxamide+TX, 4-(2-bromo-4-fluoro-phenyl)-N-(2-chloro-6-fluoro-phenyl)-2,5-dimethyl-pyrazol-3-amine+TX, 4-(2-bromo-4-fluorophenyl)-N-(2-chloro-6-fluorophenyl)-1,3-dimethyl-1H-pyrazol-5-amine+TX, fluindapyr+TX, coumethoxystrobin (jiaxiangjunzhi)+TX, Ivbenmixianan+TX, dichlobentiazox+TX, mandestrobin+TX, 3-(4,4-difluoro-3,4-dihydro-3,3-dimethylisoquinolin-1-yl)quinolone+TX, 2-[2-fluoro-6-[(8-fluoro-2-methyl-3-quinolyl)oxy]phenyl]propan-2-ol+TX, oxathiapiprolin+TX, tert-butyl N-[6-[[[(1-methyltetrazol-5-yl)-phenyl-methylene]amino]oxymethyl]-2-pyridyl]carbamate+TX, pyraziflumid+TX, inpyrfluxam+TX, trolprocarb+TX, mefentrifluconazole+TX, ipfentrifluconazole+TX, 2-(difluoromethyl)-N-[(3R)-3-ethyl-1,1-dimethyl-indan-4-yl]pyridine-3-carboxamide+TX, N'-(2,5-dimethyl-4-phenoxy-phenyl)-N-ethyl-N-methyl-formamidine+TX, N'-[4-(4,5-dichlorothiazol-2-yl)oxy-2,5-dimethyl-phenyl]-N-ethyl-N-methyl-formamidine+TX, [2-[3-[2-[1-[2-[3,5-bis(difluoromethyl)pyrazol-1-yl]acetyl]-4-piperidyl]thiazol-4-yl]-4,5-dihydroisoxazol-5-yl]-3-chloro-phenyl] methanesulfonate+TX, but-3-ynyl N-[6-[[(Z)-[(1-methyltetrazol-5-yl)-phenyl-methylene]amino]oxymethyl]-2-pyridyl]carbamate+TX, methyl N-[[5-[4-(2,4-dimethylphenyl)triazol-2-yl]-2-methyl-phenyl]methyl]carbamate+TX, 3-chloro-6-methyl-5-phenyl-4-(2,4,6-trifluorophenyl)pyridazine+TX, pyridachlometyl+TX, 3-(difluoromethyl)-1-methyl-N-[1,1,3-trimethylindan-4-yl]pyrazole-4-carboxamide+TX, 1-[2-[[1-(4-chlorophenyl)pyrazol-3-yl]oxymethyl]-3-methyl-phenyl]-4-methyl-tetrazol-5-one+TX, 1-methyl-4-[3-methyl-2-[[2-methyl-4-(3,4,5-trimethylpyrazol-1-yl)phenoxy]methyl]phenyl]tetrazol-5-one+TX, aminopyrifen+TX, ametoctradin+TX, amisulbrom+TX, penflufen+TX, (Z,2E)-5-[1-(4-chlorophenyl)pyrazol-3-yl]oxy-2-methoxyimino-N,3-dimethyl-pent-3-enamide+TX, florylpicoxamid+TX, fenpicoxamid+TX, metarylpicoxamid+TX, tebufloquin+TX, ipflufenoquin+TX, quinofumelin+TX, isofetamid+TX, N-[2-[2,4-dichloro-phenoxy]phenyl]-3-(difluoromethyl)-1-methyl-pyrazole-4-carboxamide+TX, N-[2-[2-chloro-4-(trifluoromethyl)phenoxy]phenyl]-3-(difluoromethyl)-1-methyl-pyrazole-4-carboxamide+TX, benzothiostrobin+TX, phenamacril+TX, 5-amino-1,3,4-thiadiazole-2-thiol zinc salt (2:1)+TX, fluopyram+TX, flufenoxadiazam+TX, flutianil+TX, fluopimomide+TX, pyrapropoyne+TX, picarbutrazox+TX, 2-(difluoromethyl)-N-(3-ethyl-1,1-dimethyl-indan-4-yl)pyridine-3-carboxamide+TX, 2-(difluoromethyl)-N-((3R)-1,1,3-trimethylindan-4-yl)pyridine-3-carboxamide+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, metyltetraprole+TX, 2-(difluoromethyl)-N-((3R)-1,1,3-trimethylindan-4-yl)pyridine-3-carboxamide+TX, α-(1,1-dimethylethyl)-α-[4'-(trifluoromethoxy) [1,1'-biphenyl]-4-yl]-5-pyrimidinemethanol+TX, fluoxapiprolin+TX, enoxastrobin+TX, 4-[[6-[2-(2,4-difluorophenyl)-1,1-difluoro-2-hydroxy-3-(1,2,4-triazol-1-yl)propyl]-3-pyridyl]oxy]benzonitrile+TX, 4-[[6-[2-(2,4-difluorophenyl)-1,1-difluoro-2-hydroxy-3-(5-sulfanyl-1,2,4-triazol-1-yl)propyl]-3-pyridyl]oxy]benzonitrile+TX, 4-[[6-[2-(2,4-difluorophenyl)-1,1-difluoro-2-hydroxy-3-(5-thioxo-4H-1,2,4-triazol-1-yl)propyl]-3-pyridyl]oxy]benzonitrile+TX, trinexapac+TX, coumoxystrobin+TX, zhongshengmycin+TX, thiodiazole copper+TX, zinc thiazole+TX, amectotractin+TX, iprodione+TX, seboctylamine+TX; N'-[5-bromo-2-methyl-6-[(1S)-1-methyl-2-propoxy-ethoxy]-3-pyridyl]-N-ethyl-N-methyl-formamidine+TX, N'-[5-bromo-2-methyl-6-[(1R)-1-methyl-2-propoxy-ethoxy]-3-pyridyl]-N-ethyl-N-methyl-formamidine+TX, N'-[5-bromo-2-methyl-6-(1-methyl-2-propoxy-ethoxy)-3-pyridyl]-N-ethyl-N-methyl-formamidine+TX, N'-[5-chloro-2-methyl-6-(1-methyl-2-propoxy-ethoxy)-3-pyridyl]-N-ethyl-N-methyl-formamidine+TX, N'-[5-bromo-2-methyl-6-(1-methyl-2-propoxy-ethoxy)-3-pyridyl]-N-isopropyl-N-methyl-formamidine+TX (these compounds may be prepared from the methods described in WO2015/155075); N'-[5-bromo-2-methyl-6-(2-propoxypropoxy)-3-pyridyl]-N-ethyl-N-methyl-formamidine+TX (this compound may be prepared from the methods described in IPCOM000249876D); N-isopropyl-N'-[5-methoxy-2-methyl-4-(2,2,2-trifluoro-1-hydroxy-1-phenyl-ethyl)phenyl]-N-methyl-formamidine+TX, N'-[4-(1-cyclopropyl-2,2,2-trifluoro-1-hydroxy-ethyl)-5-methoxy-2-methyl-phenyl]-N-isopropyl-N-methyl-formamidine+TX (these compounds may be prepared from the methods described in WO2018/228896); N-ethyl-N'-[5-methoxy-2-methyl-4-[(2-trifluoromethyl)oxetan-2-yl]phenyl]-N-methyl-formamidine+TX, N-ethyl-N'-[5-methoxy-2-methyl-4-[(2-trifluoromethyl)tetrahydrofuran-2-yl]phenyl]-N-methyl-formamidine+TX (these compounds may be prepared from the methods described in WO2019/110427); N-[(1R)-1-benzyl-3-chloro-1-methyl-but-3-enyl]-8-fluoro-quinoline-3-carboxamide+TX, N-[(1S)-1-benzyl-3-chloro-1-methyl-but-3-enyl]-8-fluoro-quinoline-3-carboxamide+TX, N-[(1R)-1-benzyl-3,3,3-trifluoro-1-methyl-propyl]-8-fluoro-quinoline-3-carboxamide+TX, N-[(1S)-1-benzyl-3,3,3-trifluoro-1-methyl-propyl]-8-fluoro-quinoline-3-carboxamide+TX, N-[(1R)-1-benzyl-1,3-dimethyl-butyl]-7,8-difluoro-quinoline-3-carboxamide+TX, N-[(1S)-1-benzyl-1,3-dimethyl-butyl]-7,8-difluoro-quinoline-3-carboxamide+TX, 8-fluoro-N-[(1R)-1-[(3-fluorophenyl)methyl]-1,3-dimethyl-butyl]quinoline-3-carboxamide+TX, 8-fluoro-N-[(1S)-1-[(3-fluorophenyl)methyl]-1,3-dimethyl-butyl]quinoline-3-carboxamide+TX, N-[(1R)-1-benzyl-1,3-dimethyl-butyl]-8-fluoro-quinoline-3-carboxamide+TX, N-[(1S)-1-benzyl-1,3-dimethyl-butyl]-8-fluoro-quinoline-3-carboxamide+TX, N-((1R)-1-benzyl-3-chloro-1-methyl-but-3-enyl)-8-fluoro-quinoline-3-carboxamide+TX, N-((1S)-1-benzyl-3-chloro-1-methyl-but-3-enyl)-8-fluoro-quinoline-3-carboxamide+TX (these compounds may be prepared from the methods described in WO2017/153380); 1-(6,7-dimethylpyrazolo[1,5-a]pyridin-3-yl)-4,4,5-trifluoro-3,3-dimethyl-isoquinoline+TX, 1-(6,7-dimethylpyrazolo[1,5-a]pyridin-3-yl)-4,4,6-trifluoro-3,3-dimethyl-isoquinoline+TX, 4,4-difluoro-3,3-dimethyl-1-(6-methylpyrazolo[1,5-a]pyridin-3-yl)isoquinoline+TX, 4,4-difluoro-3,3-dimethyl-1-(7-methylpyrazolo[1,5-a]pyridin-3-yl)isoquinoline+TX, 1-(6-chloro-7-methyl-pyrazolo[1,5-a]pyridin-3-yl)-4,4-difluoro-3,3-dimethyl-isoquinoline+TX (these compounds may be prepared from the methods described in WO2017/025510); 1-(4,5-dimethylbenzimidazol-1-yl)-4,4,5-trifluoro-3,3-dimethyl-isoquinoline+TX, 1-(4,5-dimethylbenzimidazol-1-yl)-4,4-difluoro-3,3-dimethyl-isoquinoline+TX, 6-chloro-4,4-difluoro-3,3-dimethyl-1-(4-methylbenzimidazol-1-yl)isoquinoline+TX, 4,4-difluoro-1-(5-fluoro-4-methyl-benzimidazol-1-yl)-3,3-dimethyl-isoquinoline+TX, 3-(4,4-difluoro-3,3-dimethyl-1-isoquinolyl)-7,8-dihydro-6H-cyclopenta[e]benzimidazole+TX (these compounds may be prepared from the methods described in WO2016/156085); N-methoxy-N-[[4-[5-(trifluoromethyl)-1,2,4-oxadiazol-3-yl]phenyl]methyl]cyclopropanecarboxamide+TX, N,2-dimethoxy-N-[[4-[5-(trifluoromethyl)-1,2,4-oxadiazol-3-yl]phenyl]methyl]propanamide+TX, N-ethyl-2-methyl-N-[[4-[5-(trifluoromethyl)-1,2,4-oxadiazol-3-yl]phenyl]methyl]propanamide+TX, 1-methoxy-3-methyl-1-[[4-[5-(trifluoromethyl)-1,2,4-oxadiazol-3-yl]phenyl]methyl]urea+TX, 1,3-dimethoxy-1-[[4-[5-(trifluoromethyl)-1,2,4-oxadiazol-3-yl]phenyl]methyl]urea+TX, 3-ethyl-1-methoxy-1-[[4-[5-(trifluoromethyl)-1,2,4-oxadiazol-3-yl]phenyl]methyl]urea+TX, N-[[4-[5-(trifluoromethyl)-1,2,4-oxadiazol-3-yl]phenyl]methyl]propanamide+TX, 4,4-dimethyl-2-[[4-[5-(trifluoromethyl)-1,2,4-oxadiazol-3-yl]phenyl]methyl]isoxazolidin-3-one+TX, 5,5-dimethyl-2-[[4-[5-(trifluoromethyl)-1,2,4-oxadiazol-3-yl]phenyl]methyl]isoxazolidin-3-one+TX, ethyl 1-[[4-[5-(trifluoromethyl)-1,2,4-oxadiazol-3-yl]phenyl]methyl]pyrazole-4-carboxylate+TX, N,N-dimethyl-1-[[4-[5-(trifluoromethyl)-1,2,4-oxadiazol-3-yl]phenyl]methyl]-1,2,4-triazol-3-amine+TX. The compounds in this paragraph may be prepared from the methods described in WO 2017/055473, WO 2017/055469, WO 2017/093348 and WO 2017/118689; 2-[6-(4-chlorophenoxy)-2-(trifluoromethyl)-3-pyridyl]-1-(1,2,4-triazol-1-yl)propan-2-ol+TX (this compound may be prepared from the methods described in WO 2017/029179); 2-[6-(4-bromophenoxy)-2-(trifluoromethyl)-3-pyridyl]-1-(1,2,4-triazol-1-yl)propan-2-ol+TX (this compound may be prepared from the methods described in WO 2017/029179); 3-[2-(1-chlorocyclopropyl)-3-(2-fluorophenyl)-2-hydroxy-propyl]imidazole-4-carbonitrile+TX (this compound may be prepared from the methods described in WO 2016/156290); 3-[2-(1-chlorocyclopropyl)-3-(3-chloro-2-fluoro-phenyl)-2-hydroxy-propyl]imidazole-4-carbonitrile+TX (this compound may be prepared from the methods described in WO 2016/156290); (4-phenoxyphenyl)methyl 2-amino-6-methyl-pyridine-3-carboxylate+TX (this compound may be prepared from the methods described in WO 2014/006945); 2,6-Dimethyl-1H,5H-[1,4]dithiino[2,3-c:5,6-c']dipyrrole-1,3,5,7(2H,6H)-tetrone+TX (this compound may be prepared from the methods described in WO 2011/138281); N-methyl-4-[5-(trifluoromethyl)-1,2,4-oxadiazol-3-yl]benzenecarbothioamide+TX; N-methyl-4-[5-(trifluoromethyl)-1,2,4-oxadiazol-3-yl]benzamide+TX; (Z,2E)-5-[1-(2,4-dichlorophenyl)pyrazol-3-yl]oxy-2-methoxyimino-N,3-dimethyl-pent-3-enamide+TX (this compound may be prepared from the methods described in WO 2018/153707); N'-(2-chloro-5-methyl-4-phenoxy-phenyl)-N-ethyl-N-methyl-formamidine+TX; N'-[2-chloro-4-(2-fluorophenoxy)-5-methyl-phenyl]-N-ethyl-N-methyl-formamidine+TX (this compound may be prepared from the methods described in WO 2016/202742); 2-(difluoromethyl)-N-[(3S)-3-ethyl-1,1-dimethyl-indan-4-yl]pyridine-3-carboxamide+TX (this compound may be prepared from the methods described in WO 2014/095675); (5-methyl-2-pyridyl)-[4-[5-(trifluoromethyl)-1,2,4-oxadiazol-3-yl]phenyl]methanone+TX, (3-methylisoxazol-5-yl)-[4-[5-(trifluoromethyl)-1,2,4-oxadiazol-3-yl]phenyl]methanone+TX (these compounds may be prepared from the methods described in WO 2017/220485); 2-oxo-N-propyl-2-[4-[5-(trifluoromethyl)-1,2,4-oxadiazol-3-yl]phenyl]acetamide+TX (this compound may be prepared from the methods described in WO 2018/065414); ethyl 1-[[5-[5-(trifluoromethyl)-1,2,4-oxadiazol-3-yl]-2-thienyl]methyl]pyrazole-4-carboxylate+TX (this compound may be prepared from the methods described in WO 2018/158365); 2,2-difluoro-N-methyl-2-[4-[5-(trifluoromethyl)-1,2,4-oxadiazol-3-yl]phenyl]acetamide+TX, N-[(E)-methoxyiminomethyl]-4-[5-(trifluoromethyl)-1,2,4-oxadiazol-3-yl]benzamide+TX, N-[(Z)-methoxyiminomethyl]-4-[5-(trifluoromethyl)-1,2,4-oxadiazol-3-yl]benzamide+TX, N-[N-methoxy-C-methyl-carbonimidoyl]-4-[5-(trifluoromethyl)-1,2,4-oxadiazol-3-yl]benzamide+TX (these compounds may be prepared from the methods described in WO 2018/202428);

microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana* granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus* papillae (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST2808 (Sonata®+TX, Ballad Plus®)+TX, *Bacillus sphaericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST713

(CEASE®+TX, Serenade®+TX, Rhapsody®)+TX, *Bacillus subtilis* strain QST714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry2Ae+TX, *Bacillus thuringiensis* Cry1 Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavibacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer *Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, Cedecea dravisae+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta* granulovirus (Cryptex®)+TX, *Cupriavidus campinensis*+TX, *Cydia pomonella* granulovirus (CYD-X®)+TX, *Cydia pomonella* granulovirus (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, Granulovirus (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, Mycorrhizae spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium* bilaii (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis* gigantean (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofaciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomonas fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rahnella aquatilis*+TX, *Rahnella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+

TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HCO+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus;*

Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near ambrosioides (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, *Glycine* betaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®);

pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX, 8+TX, 11 Tetradecatrienyl acetate+TX, (Z+TX,Z+TX,E)-7+TX, 11+TX, 13-Hexadecatrienal+TX, (E+TX,Z)-7+TX, 9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+

TX, *Dacnusa sibirica* (DacDigline®+TX, Minex®)+TX, *Diversinervus* spp.+TX, *Encarsia citrina*+TX, *Encarsia formosa* (*Encarsia* Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmocerus siphonini*+TX, *Eretmocerus californicus*+TX, *Eretmocerus eremicus* (Ercal®+TX, Eretline E®)+TX, *Eretmocerus eremicus* (Bemimix®)+TX, *Eretmocerus hayati*+TX, *Eretmocerus mundus* (Bemipar®+TX, Eretline M®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wireless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline Hm®+TX, Larvanem-M®)+TX, *Hippodamia convergens*+TX, *Hypoaspis aculeifer* (*aculeifer*-System®+TX, Entomite-A®)+TX, *Hypoaspis miles* (Hypoline M®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline C®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline I®)+TX, *Orius laevigatus* (Thripor-L®+TX, Oriline I®)+TX, *Orius majusculus* (Oriline M®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline P®)+TX, *Podisus maculiventris* (*Podisus*®)+TX, *Pseudacteon curvatus*+TX, *Pseudacteon obtusus*+TX, *Pseudacteon* tricuspis+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae+TX, Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-Rid®+TX, Entonem®)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus*®)+TX, *Tamarixia radiate*+TX, *Tetrastichus setifer*+TX, *Thripobius semiluteus*+TX, *Torymus sinensis*+TX, *Trichogramma brassicae* (Tricholine B®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator,* other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline D®)+TX, *Erwinia amylovora* (Harpin) (ProAct®+TX, Ni-HIBIT Gold CST®)+TX, Ferri-phosphate (Ferramol®)+TX, Funnel traps (Trapline Y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline F®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassium thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+B®)+TX; and a safener, such as benoxacor+TX, cloquintocet (including cloquintocet-mexyl)+TX, cyprosulfamide+TX, dichlormid+TX, fenchlorazole (including fenchlorazole-ethyl)+TX, fenclorim+TX, fluxofenim+TX, furilazole+TX, isoxadifen (including isoxadifen-ethyl)+TX, mefenpyr (including mefenpyr-diethyl)+TX, metcamifen+TX and oxabetrinil+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables Tables A-1 to A-48, C-1 to C-24, D-1 to D-12, and E-1 to E-12 and Table P with active ingredients described above comprises a compound selected from Tables A-1 to A-48, C-1 to C-24, D-1 to D-12, and E-1 to E-12 and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables A-1 to A-48, C-1 to C-24, D-1 to D-12, and E-1 to E-12 and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables A-1 to A-48, C-1 to C-24, D-1 to D-12, and E-1 to E-12 and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

The Examples which follow serve to illustrate the invention. Certain compounds of the invention can be distinguished from known compounds by virtue of greater efficacy at low application rates, which can be verified by the person skilled in the art using the experimental procedures outlined in the Examples, using lower application rates if necessary, for example 50 ppm, 24 ppm, 12.5 ppm, 6 ppm, 3 ppm, 1.5 ppm, 0.8 ppm or 0.2 ppm.

Example B1: Activity Against *Diabrotica* Balteata (Corn Root Worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P2, P6, P9, P10, P11, P12, P13, P14, P15, P16, P17, P18.

Example B2: Activity Against *Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P2, P4, P5, P9, P10, P11, P12, P13, P14, P15, P16.

Example B3: Activity Against *Frankliniella occidentalis* (Western Flower *Thrips*) Feeding/Contact Activity Sunflower leaf discs were placed on agar in 24-well microtiter plates and sprayed with aqueous test solutions prepared from 10,000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P1.

Example B4: Activity Against *Myzus persicae* (Green Peach Aphid) Feeding/Contact Activity Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P1, P2, P4, P5, P6, P9, P10, P11, P12, P13, P14, P15, P16, P17, P18.

Example B5: Activity Against *Plutella xylostella* (Diamond Back Moth)

24-well microtiter plates with artificial diet were treated with aqueous test solutions prepared from 10,000 ppm DMSO stock solutions by pipetting. After drying, *Plutella* eggs were pipetted through a plastic stencil onto a gel blotting paper and the plate was closed with it. The samples were assessed for mortality and growth inhibition in comparison to untreated samples 8 days after infestation.

The following compounds gave an effect of at least 80% in at least one of the two categories (mortality or growth inhibition) at an application rate of 200 ppm: P1, P2, P4, P5, P6, P7, P9, P10, P11, P12, P13, P14, P15, P16, P17, P18.

Example B6: Activity Against *Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P1, P2, P5, P6, P7, P9, P10, P13, P14, P15, P16, P17, P18.

Example B7: Activity Against *Bemisia tabaci* (Cotton White Fly) Feeding/Contact Activity Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compounds resulted in at least 80% mortality at an application rate of 200 ppm: P17.

Example B8: Activity Against *Chilo suppressalis* (Striped Rice Stemborer)

24-well microtiter plates with artificial diet were treated with aqueous test solutions prepared from 10,000 ppm DMSO stock solutions by pipetting. After drying, the plates were infested with L2 larvae (6-8 per well). The samples were assessed for mortality, anti-feeding effect, and growth inhibition in comparison to untreated samples 6 days after infestation. Control of *Chilo suppressalis* by a test sample is given when at least one of the categories mortality, anti-feedant effect, and growth inhibition is higher than the untreated sample.

The following compounds resulted in at least 80% control at an application rate of 200 ppm: P1, P2, P3, P4, P5, P6, P7, P9, P10, P11, P12, P13, P14, P16, P17, P18.

Example B9: Activity Against *Myzus persicae* (Green Peach Aphid). Systemic Activity Roots of pea seedlings infested with an aphid population of mixed ages were placed directly into aqueous test solutions prepared from 10,000 DMSO stock solutions. The samples were assessed for mortality 6 days after placing seedlings into test solutions.

The following compounds resulted in at least 80% mortality at a test rate of 24 ppm: P2, P4, P5, P6, P8, P9, P10, P11, P12, P13, P17.

The invention claimed is:

1. A compound of formula (I)

(I)

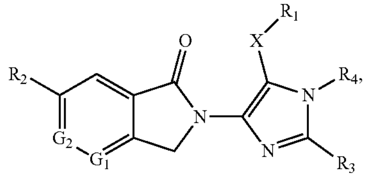

wherein $G_1$ and $G_2$ are, independently from each other, CH or N;

$R_2$ is $C_1$-$C_6$haloalkyl, $C_1$-$C_4$haloalkylsulfanyl, $C_1$-$C_4$haloalkylsulfinyl, $C_1$-$C_4$haloalkylsulfonyl, $C_1$-$C_6$haloalkoxy or $C_1$-$C_4$haloalkylsulfonyloxy;

X is S, SO, or $SO_2$;

$R_1$ is $C_1$-$C_4$alkyl, or $C_3$-$C_6$cycloalkyl-$C_1$-$C_4$alkyl;

$R_4$ is $C_1$-$C_4$alkyl;

$R_3$ is hydrogen, halogen, $C_1$-$C_4$alkyl, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$alkoxy, $C_1$-$C_6$haloalkoxy, —CO($NR_5R_6$), —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl; or $R_3$ is a five- to six-membered saturated, partially saturated, aromatic or heteroaromatic ring system, linked via a ring carbon atom to the imidazole ring which is connected to the substituent $R_4$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl, $C_1$-$C_4$alkylsulfonyl, $C_3$-$C_6$cycloalkyl, $C_3$-$C_6$cycloalkyl monosubstituted by cyano, $C_1$-$C_6$cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom; or $R_3$ is a five-membered heteroaromatic ring system linked via a ring nitrogen atom to the imidazole ring which is connected to the substituent $R_4$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl, $C_1$-$C_4$alkylsulfonyl, $C_3$-$C_6$cycloalkyl, $C_3$-$C_6$cycloalkyl monosubstituted by cyano, $C_1$-$C_6$cyanoalkyl, ($C_3$-$C_8$)cycloalkyl-($C_1$-$C_6$)alkyl-, ($C_3$-$C_8$)cycloalkyl monosubstituted by cyano-($C_1$-$C_6$)alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom;

$R_5$ and $R_6$ are independently H, $C_1$-$C_6$alkyl, $C_1$-$C_6$haloalkyl or $C_3$-$C_6$cycloalkyl; and $R_7$ is $C_1$-$C_6$alkyl, $C_1$-$C_6$haloalkyl or $C_3$-$C_6$cycloalkyl; or an agrochemically acceptable salt, stereoisomer, enantiomer, tautomer or N-oxide of a compound of formula I.

2. A compound of formula I according to claim 1, represented by a compound of formula I-A1:

I-A1

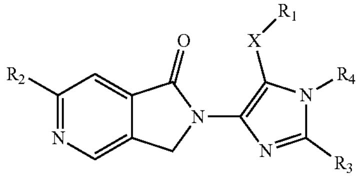

wherein $R_1$, $R_2$, $R_3$, X, and $R_4$ are as defined under formula I in claim 1, or an agrochemically acceptable salt, stereoisomer, enantiomer, tautomer or N-oxide thereof.

3. A compound of formula I according to claim 1, represented by a compound of formula I-B1:

I-B1

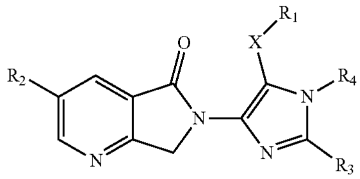

wherein $R_1$, $R_2$, $R_3$, X, and $R_4$ are as defined under formula I in claim 1, or an agrochemically acceptable salt, stereoisomer, enantiomer, tautomer or N-oxide of a compound of formula I-B1.

4. A compound of formula I according to claim 1, represented by a compound of formula I-C1:

I-C1

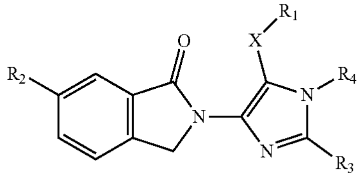

wherein $R_1$, $R_2$, $R_3$, X, and $R_4$ are as defined under formula I in claim 1; or an agrochemically acceptable salt, stereoisomer, enantiomer, tautomer or N-oxide of a compound of formula I-$C_1$.

5. A compound of formula I according to claim 1, represented by a compound of formula I-D1:

I-D1

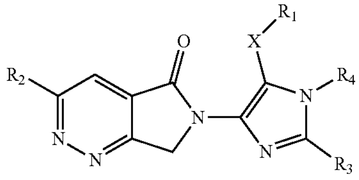

wherein $R_1$, $R_2$, $R_3$, X, and $R_4$ are as defined under formula I in claim 1; or an agrochemically acceptable salt, stereoisomer, enantiomer, tautomer or N-oxide of a compound of formula I-D1.

6. A compound of formula I according to claim 1, represented by a compound of formula I-E:

(I-E)

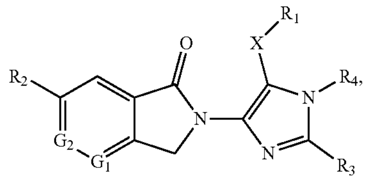

wherein $G_1$ and $G_2$ are, independently from each other, CH or N;

$R_1$ is $C_1$-$C_4$alkyl or cyclopropyl-$C_1$-$C_4$alkyl;

$R_2$ is $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;

and wherein

X is S, SO, or $SO_2$;

$R_4$ is $C_1$-$C_4$alkyl;

$R_3$ is hydrogen, halogen, $C_1$-$C_4$alkyl, $C_1$-$C_6$haloalkyl, $C_3$-$C_6$cycloalkyl, $C_3$-$C_6$cycloalkyl monosubstituted by cyano, $C_1$-$C_6$cyanoalkyl, $C_1$-$C_6$alkoxy, $C_1$-$C_6$haloalkoxy, —CO($NR_5R_6$), —$NR_5COR_7$, ($C_3$-$C_8$)cycloalkyl-($C_1$-$C_6$)alkyl- or ($C_3$-$C_8$)cycloalkyl monosubstituted by cyano-($C_1$-$C_6$)alkyl-; or $R_3$ is a five- to six-membered saturated, partially saturated, aromatic ring or heteroaromatic ring system, linked via a ring carbon atom to the imidazole ring which is connected to the substituent $R_4$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl, $C_1$-$C_4$alkylsulfonyl, $C_3$-$C_6$cycloalkyl, $C_3$-$C_6$cycloalkyl monosubstituted by cyano, $C_1$-$C_6$cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system can contain 1, 2 or 3 ring heteroatoms selected from the group consisting of nitrogen, oxygen and sulfur, where said ring system may not contain more than one ring oxygen atom and may not contain more than one ring sulfur atom; or $R_3$ is a five-membered aromatic ring system linked via a ring nitrogen atom to the imidazole ring which is connected to the substituent $R_4$, said ring system is unsubstituted or is mono- or polysubstituted by substituents selected from the group consisting of halogen, cyano, $C_1$-$C_4$alkyl, $C_1$-$C_4$haloalkyl, $C_1$-$C_4$alkoxy, $C_1$-$C_4$haloalkoxy, $C_1$-$C_4$alkylsulfanyl, $C_1$-$C_4$alkylsulfinyl, $C_1$-$C_4$alkylsulfonyl, $C_3$-$C_6$cycloalkyl, $C_3$-$C_6$cycloalkyl monosubstituted by cyano, $C_1$-$C_6$cyanoalkyl, ($C_3$-$C_8$)cycloalkyl-($C_1$-$C_6$)alkyl- and ($C_3$-$C_8$)cycloalkyl monosubstituted by cyano-($C_1$-$C_6$)alkyl-; and said ring system contains 1, 2 or 3 ring heteroatoms selected from the group consisting of nitrogen, oxygen and sulfur, where said ring system contains at least one ring nitrogen atom and may not contain more than one ring oxygen atom and may not contain more than one ring sulfur atom;

$R_5$ and $R_6$ are independently H, $C_1$-$C_6$alkyl, $C_1$-$C_6$haloalkyl or $C_3$-$C_6$cycloalkyl; and $R_7$ is $C_1$-$C_6$alkyl, $C_1$-$C_6$haloalkyl or $C_3$-$C_6$cycloalkyl; or an agrochemically acceptable salt, stereoisomer, enantiomer, tautomer or N-oxide of a compound of formula I-E.

7. A compound according to claim 1, wherein: X is S or $SO_2$.

8. A compound according to claim 1, wherein: $R_1$ is ethyl.

9. A compound according to claim 1, wherein: $R_2$ is $OCF_3$, —$CF_2CF_3$ or —$CF_3$.

10. A compound according to claim 1, wherein: $R_3$ is selected from the group consisting of hydrogen; halogen; cyclopropyl; cyanocyclopropyl; trifluoroethoxy; —$CONCH_3(CH_2CF_3)$; —$N(CH_3)COCH_2CF_3$; N-linked pyrazolyl which can be mono-substituted by chloro, cyclopropyl or trifluoromethyl; C-linked pyrimidinyl; C-linked pyrazolyl which can be mono-substituted by cyclopropyl, —$CHF_2$, —$CH_2CHF_2$, —$CH_2CF_3$, —($CH_2$)-cyclopropyl, —($CH_2$)-1-cyanocyclopropyl or trifluoromethyl; C-linked dihydroisoxazole which can be mono-substituted by chloro, trifluoromethyl or cyclopropyl; and phenyl which can be mono-substituted by chloro or fluoro, cylopropyl, cylopropyl substituted with cyano.

11. A compound according to claim 1, wherein: $R_4$ is methyl or ethyl.

12. A compound of formula I according to claim 1, represented by a compound of formula I-F:

(I-F)

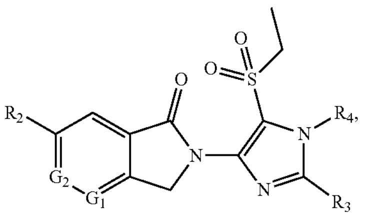

wherein $G_1$ is N and $G_2$ is CH; or both $G_1$ and $G_2$ are CH;

$R_2$ is $C_1$-$C_6$haloalkyl or $C_1$-$C_6$haloalkoxy;

$R_4$ is $C_1$-$C_4$alkyl; and $R_3$ is is selected from the group consisting of cyclopropyl; $C_1$-$C_6$haloalkoxy; phenyl which can be mono-substituted by cyanocylopropyl; C-linked pyrimidinyl; N-linked pyrazolyl which can be mono-substituted by chloro, cyclopropyl or trifluoromethyl; C-linked pyrazolyl which is N-substituted by cyclopropyl, —$CHF_2$, —$CH_2CHF_2$, —$CH_2CF_3$, —($CH_2$)-cyclopropyl, or —($CH_2$—)-cyanocyclopropyl; and C-linked dihydroisoxazole which can be mono-substituted by cyclopropyl.

13. A compound of formula I according to claim 1, selected from the group consisting of:

2-[2-(1-cyclopropylpyrazol-4-yl)-5-ethylsulfonyl-1-methyl-imidazol-4-yl]-6-(trifluoromethoxy)isoindolin-1-one (compound P1);

6-[2-(1-cyclopropylpyrazol-4-yl)-5-ethylsulfonyl-1-methyl-imidazol-4-yl]-3-(trifluoromethyl)-7H-pyrrolo[3,4-b]pyridin-5-one (compound P2);

6-[2-(3-cyclopropyl-4,5-dihydroisoxazol-5-yl)-5-ethylsulfonyl-1-methyl-imidazol-4-yl]-3-(trifluoromethyl)-7H-pyrrolo[3,4-b]pyridin-5-one (compound P3);

1-[[4-[5-ethylsulfonyl-1-methyl-4-[5-oxo-3-(trifluoromethyl)-7H-pyrrolo[3,4-b]pyridin-6-yl]imidazol-2-yl]pyrazol-1-yl]methyl]cyclopropanecarbonitrile (compound P4);

6-[2-[1-(2,2-difluoroethyl)pyrazol-4-yl]-5-ethylsulfonyl-1-methyl-imidazol-4-yl]-3-(trifluoromethyl)-7H-pyrrolo[3,4-b]pyridin-5-one (compound P5);

6-[5-ethylsulfonyl-1-methyl-2-(2,2,2-trifluoroethoxy)imidazol-4-yl]-3-(trifluoromethyl)-7H-pyrrolo[3,4-b]pyridin-5-one (compound P6);

2-(5-ethylsulfonyl-1-methyl-2-pyrimidin-5-yl-imidazol-4-yl)-6-(trifluoromethoxy)isoindolin-1-one (compound P7);

6-(5-ethylsulfonyl-1-methyl-2-pyrimidin-5-yl-imidazol-4-yl)-3-(trifluoromethyl)-7H-pyrrolo[3,4-b]pyridin-5-one (compound P8);

6-[2-[1-(cyclopropylmethyl)pyrazol-4-yl]-5-ethylsulfonyl-1-methyl-imidazol-4-yl]-3-(trifluoromethyl)-7H-pyrrolo[3,4-b]pyridin-5-one (compound P9);

6-[5-ethylsulfonyl-1-methyl-2-[1-(2,2,2-trifluoroethyl)pyrazol-4-yl]imidazol-4-yl]-3-(trifluoromethyl)-7H-pyrrolo[3,4-b]pyridin-5-one (compound P10);

2-(5-ethylsulfonyl-1-methyl-2-pyrimidin-2-yl-imidazol-4-yl)-6-(trifluoromethoxy)isoindolin-1-one (compound P11);

6-(5-ethylsulfonyl-1-methyl-2-pyrimidin-2-yl-imidazol-4-yl)-3-(trifluoromethyl)-7H-pyrrolo[3,4-b]pyridin-5-one (compound P12);

6-[2-[1-(difluoromethyl)pyrazol-4-yl]-5-ethylsulfonyl-1-methyl-imidazol-4-yl]-3-(trifluoromethyl)-7H-pyrrolo[3,4-b]pyridin-5-one (compound P13);

6-[5-ethylsulfonyl-1-methyl-2-[4-(trifluoromethyl)pyrazol-1-yl]imidazol-4-yl]-3-(trifluoromethyl)-7H-pyrrolo[3,4-b]pyridin-5-one (compound P14);

6-[2-(3-cyclopropylpyrazol-1-yl)-5-ethylsulfonyl-1-methyl-imidazol-4-yl]-3-(trifluoromethyl)-7H-pyrrolo[3,4-b]pyridin-5-one (compound P15);

6-[2-(3-chloropyrazol-1-yl)-5-ethylsulfonyl-1-methyl-imidazol-4-yl]-3-(trifluoromethyl)-7H-pyrrolo[3,4-b]pyridin-5-one (compound P16);

6-(2-cyclopropyl-5-ethylsulfonyl-1-methyl-imidazol-4-yl)-3-(trifluoromethyl)-7H-pyrrolo[3,4-b]pyridin-5-one (compound P17); and 1-[4-[5-ethylsulfonyl-1-methyl-4-[5-oxo-3-(trifluoromethyl)-7H-pyrrolo[3,4-b]pyridin-6-yl]imidazol-2-yl]phenyl]cyclopropanecarbonitrile (compound P18).

14. A composition comprising an insecticidally effective amount of a compound of formula (I), or an agrochemically acceptable salt, stereoisomer, enantiomer, tautomer or N-oxide thereof, as defined in claim 1 and, an auxiliary or diluent.

15. A method of combating and controlling insects which comprises applying to a pest, to a locus of a pest, or to a plant susceptible to attack by a pest an insecticidally effective amount of a compound of formula (I), or an agrochemically acceptable salt, stereoisomer, enantiomer, tautomer or N-oxide thereof, as defined in claim 1.

16. A method for the protection of plant propagation material from the attack by insects, which comprises treating the propagation material or the site, where the propagation material is planted, with a composition according to claim 14.

17. A compound of formula XVII-a (XVII-a)

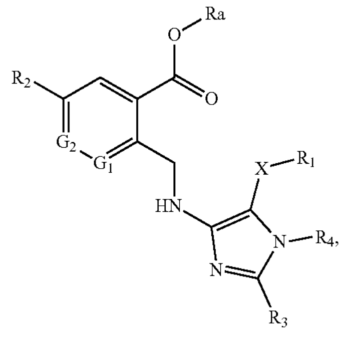

wherein

X, $R_2$, $G_1$, $G_2$, $R_1$, $R_3$, $R_4$, $R_5$, $R_6$, and $R_7$ are as defined under formula I according to claim 1; and Ra is hydrogen, $C_1$-$C_6$alkyl, benzyl or phenyl.

18. A compound of formula XIX (XIX)

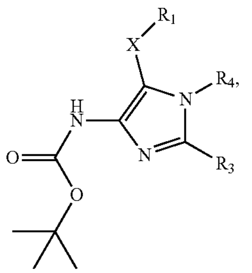

wherein $R_1$, X, $R_3$, $R_4$, $R_5$, $R_6$ and $R_7$ are as defined under formula I according to claim 1; with the proviso that the compounds tert-butyl N-(2-cyclopropyl-5-ethylsulfanyl-1-methyl-imidazol-4-yl)carbamate and tert-butyl N-[5-ethylsulfanyl-1-methyl-2-[4-(trifluoromethyl)phenyl]imidazol-4-yl]carbamate are excluded.

19. A compound of formula I according to claim 12, wherein $R_2$ is $CF_3$, $CF_2CF_3$ or $OCF_3$;

$R_4$ is methyl or ethyl; and $R_3$ is selected from the group consisting of cyclopropyl; trifluoroethoxy; phenyl which can be mono-substituted by cyanocylopropyl; C-linked pyrimidinyl; N-linked pyrazolyl which can be mono-substituted by chloro, cyclopropyl or trifluoromethyl; C-linked pyrazolyl which is N-substituted by cyclopropyl, $-CHF_2$, $-CH_2CHF_2$, $-CH_2CF_3$, $-(CH_2)$-cyclopropyl, or $-(CH_2)$-cyanocyclopropyl; and C-linked dihydroisoxazole which is mono-substituted by cyclopropyl.

20. A compound according to claim 1, wherein X is $SO_2$.

21. A compound of formula XIX according to claim 18, selected from the group consisting of:

tert-butyl N-[2-(1-cyclopropylpyrazol-4-yl)-5-ethylsulfonyl-1-methyl-imidazol-4-yl]carbamate (compound I-11);

tert-butyl N-[2-(3-cyclopropyl-4,5-dihydroisoxazol-5-yl)-5-ethylsulfonyl-1-methyl-imidazol-4-yl]carbamate (compound I-16);

tert-butyl N-[2-[1-[(1-cyanocyclopropyl)methyl]pyrazol-4-yl]-5-ethylsulfonyl-1-methyl-imidazol-4-yl]carbamate (compound I-18);

tert-butyl N-[2-[1-(2,2-difluoroethyl)pyrazol-4-yl]-5-ethylsulfonyl-1-methyl-imidazol-4-yl]carbamate (compound I-20);

tert-butyl N-[5-ethylsulfonyl-1-methyl-2-(2,2,2-trifluoroethoxy)imidazol-4-yl]carbamate (compound I-22);

tert-butyl N-(5-ethylsulfonyl-1-methyl-2-pyrimidin-5-yl-imidazol-4-yl)carbamate (compound I-24);

tert-butyl N-[2-[1-(cyclopropylmethyl)pyrazol-4-yl]-5-ethylsulfonyl-1-methyl-imidazol-4-yl]carbamate (compound I-26);

tert-butyl N-[5-ethylsulfonyl-1-methyl-2-[1-(2,2,2-trifluoroethyl)pyrazol-4-yl]imidazol-4-yl]carbamate (compound I-28);

tert-butyl N-(5-ethylsulfonyl-1-methyl-2-pyrimidin-2-yl-imidazol-4-yl)carbamate (compound I-29);

tert-butyl N-[2-[1-(difluoromethyl)pyrazol-4-yl]-5-ethylsulfonyl-1-methyl-imidazol-4-yl]carbamate (compound I-31);

tert-butyl N-[5-ethylsulfonyl-1-methyl-2-[4-(trifluoromethyl)pyrazol-1-yl]imidazol-4-yl]carbamate (compound I-34);

tert-butyl N-[2-(3-chloropyrazol-1-yl)-5-ethylsulfonyl-1-methyl-imidazol-4-yl]carbamate (compound I-36); and tert-butyl N-[2-[4-(1-cyanocyclopropyl)phenyl]-5-ethylsulfonyl-1-methyl-imidazol-4-yl]carbamate (compound I-38).

* * * * *